(12) United States Patent
Matak et al.

(10) Patent No.: US 10,610,761 B1
(45) Date of Patent: *Apr. 7, 2020

(54) SYSTEMS, METHODS, AND APPARATUS FOR MEASURING ATHLETIC PERFORMANCE CHARACTERISTICS

(71) Applicant: MAYFONK ATHLETIC LLC, Plantation, FL (US)

(72) Inventors: Martin Matak, Plantation, FL (US); Jonathan Mitts, Ft. Lauderdale, FL (US)

(73) Assignee: Mayfonk Athletic LLC, Ft. Lauderdale, FL (US)

( * ) Notice: Subject to any disclaimer, the term of this patent is extended or adjusted under 35 U.S.C. 154(b) by 116 days.

This patent is subject to a terminal disclaimer.

(21) Appl. No.: 15/859,138

(22) Filed: Dec. 29, 2017

Related U.S. Application Data

(60) Continuation of application No. 14/103,445, filed on Dec. 11, 2013, now Pat. No. 9,855,484, which is a continuation-in-part of application No. 13/591,895, filed on Aug. 22, 2012, now Pat. No. 8,860,584, which is a division of application No. 12/429,246, filed on Apr. 24, 2009, now Pat. No. 8,253,586.

(51) Int. Cl.
 *A63B 71/06* (2006.01)
(52) U.S. Cl.
 CPC .................................. *A63B 71/06* (2013.01)
(58) Field of Classification Search
 CPC .................................................. G04B 47/00
 USPC .................................................... 340/870.07
 See application file for complete search history.

(56) References Cited

U.S. PATENT DOCUMENTS

| | | | |
|---|---|---|---|
| 4,089,057 A | 5/1978 | Eriksson | |
| 4,371,945 A | 2/1983 | Karr et al. | |
| 4,703,445 A | 10/1987 | Dassler | |
| 4,722,222 A | 2/1988 | Purdy et al. | |
| 4,736,312 A | 4/1988 | Dassler et al. | |
| 5,206,652 A | 4/1993 | Hoyt et al. | |
| 5,452,269 A | 9/1995 | Cherdak | |
| 5,720,200 A | 2/1998 | Anderson et al. | |
| 5,724,265 A | 3/1998 | Hutchings | |

(Continued)

FOREIGN PATENT DOCUMENTS

JP 202004121267 4/2004

*Primary Examiner* — Dharti H Patel
(74) *Attorney, Agent, or Firm* — Duane Morris LLP

(57) ABSTRACT

An athletic performance measuring unit can measure numerous athletic performance parameters for an athlete either during practice or during competition. The measured parameters may be used by the athlete to evaluate the improvement in their performance as well as compare their level of performance against peers. The athletic performance measuring unit can also be configure to transmit the sensed sensor data to a personal processing unit, such as a smart device, for calculation of one or more athletic performance parameters. The calculated athletic performance parameters can be transmitted by the PPU to other electronic devices of those fans interested in following the athletic performance of a particular athlete, group of athletes, and/or team. Further, the athletic performance measuring unit can be configured to be integrated with the display system of an arena or stadium such that the athletic performance parameters can be displayed on the scoreboard of the arena.

20 Claims, 29 Drawing Sheets

(56) References Cited

U.S. PATENT DOCUMENTS

| | | |
|---|---|---|
| 5,844,861 A | 12/1998 | Maurer |
| 6,181,647 B1 | 1/2001 | Tipton et al. |
| 6,243,659 B1 | 6/2001 | Dominici et al. |
| 6,499,000 B2 | 12/2002 | Flentov et al. |
| 6,614,352 B2 | 9/2003 | Pellet et al. |
| 7,054,784 B2 | 5/2006 | Flentov et al. |
| 7,171,331 B2 | 1/2007 | Vock et al. |
| 7,192,387 B2 | 3/2007 | Mendel |
| 7,200,517 B2 | 4/2007 | Darley et al. |
| 7,331,310 B1 | 2/2008 | Sersland et al. |
| 7,693,668 B2 | 4/2010 | Vock et al. |
| 8,253,586 B1 | 8/2012 | Matak |
| 9,855,484 B1 * | 1/2018 | Matak .................. A63B 71/06 |
| 2007/0011919 A1 | 1/2007 | Case |
| 2007/0021269 A1 | 1/2007 | Shum |
| 2007/0142715 A1 | 6/2007 | Banet et al. |
| 2008/0306707 A1 | 12/2008 | Vock |

* cited by examiner

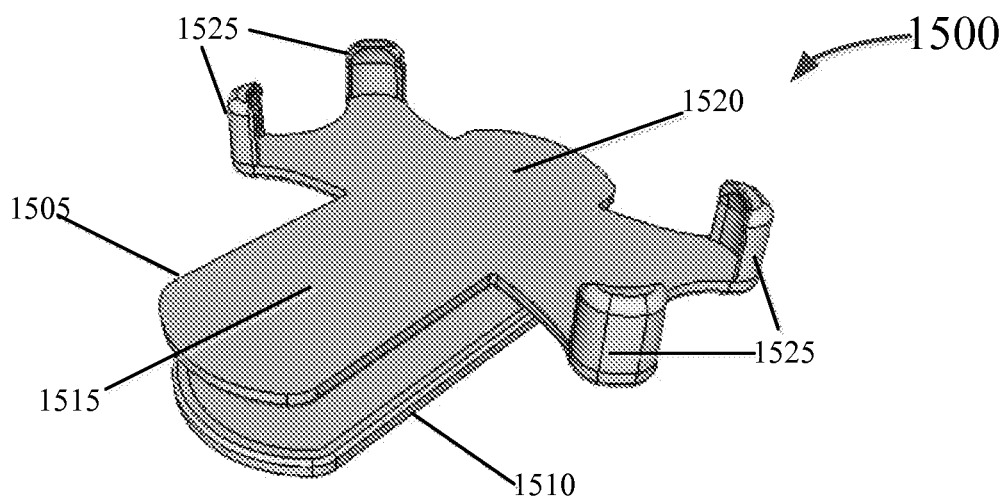
FIG. 15A
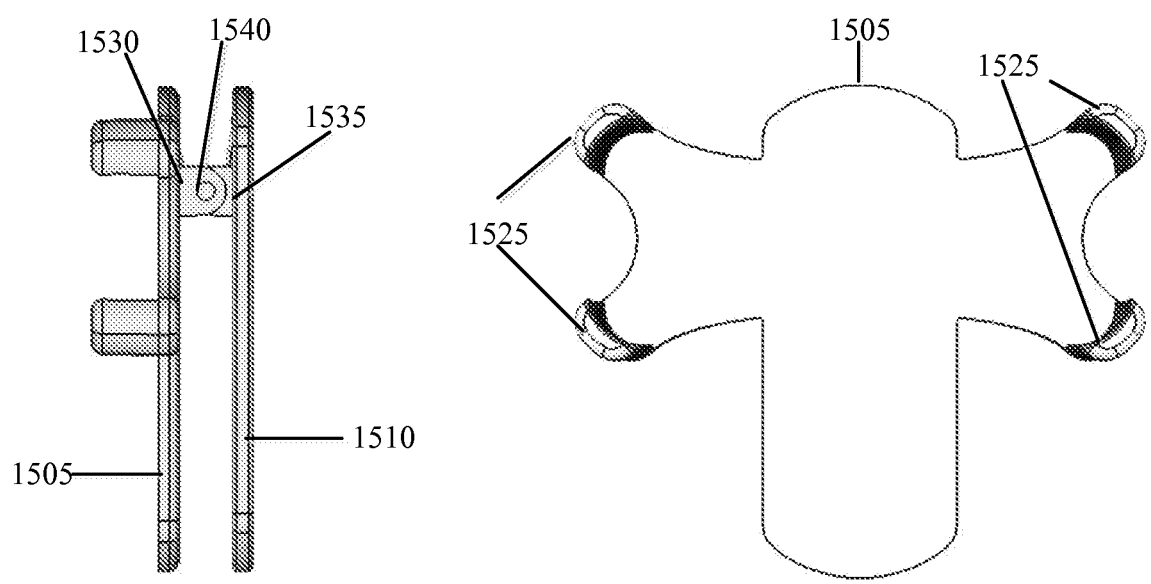
FIG. 15B  FIG. 15C

SYSTEMS, METHODS, AND APPARATUS FOR MEASURING ATHLETIC PERFORMANCE CHARACTERISTICS

CROSS-REFERENCE TO RELATED APPLICATIONS

This application is a continuation of and claims priority to co-pending U.S. patent application Ser. No. 14/103,445, which is a continuation-in-part of and claims priority under 35 U.S.C. § 120 to U.S. Pat. No. 8,860,584, titled Athletic-Wear Having Integral Measuring Sensors, which is a continuation of and claims priority under 35 U.S.C. § 120 to U.S. Pat. No. 8,253,586, titled Athletic-Wear Having Integral Measuring Sensors, the entire contents of each of which are hereby incorporated herein by reference for all purposes.

TECHNICAL FIELD

Aspects of this disclosure relate generally to electronic devices for measuring and displaying information, and more particularly to electronic devices having electronic circuitry and sensors for measuring, processing, displaying, and/or transmitting the various parameters of an athlete's performance, including, for example, real-time or near real-time display and data transmission.

BACKGROUND

Conventional athletic wear, such as shoes and boots have been designed that include technology for measuring and monitoring specific aspects of individual or athletic performance. For example, pedometers have been incorporated in footwear for measuring the distance a person walks or runs based upon body motion and different theoretical mathematical calculations. In addition, footwear and other athletic wear has been designed to measure and display specific physiological parameters such as pulse rate, weight and calorie loss, body temperature and the like. While these devices provide useful data for those who walk or run, other activities/sports may have other useful parameters, such as a jump height or vertical displacement, that are not currently capable of being measured and/or transmitted while the activity/sport is taking place. Further, these conventional devices are not able to monitor multiple athletes at one time to determine the amount of time those athletes are taking part in competition or to determine their level of output and/or the change in their level of output with regard to jump height/vertical displacement during the time they are taking part in competition. Such information could prove useful in determining if an athlete's output becomes less over time and whether the athlete may be tired and a substitution of that athlete may be in order.

BRIEF DESCRIPTION OF THE DRAWINGS

Reference will now be made to the accompanying drawings, which are not necessarily drawn to scale, and wherein:

FIGS. 15A-C present multiple views of a clip device for holding the athletic performance measuring unit of FIGS. 14A-H and securing the clip device to an article of clothing or other apparatus used by the athlete in accordance with one exemplary embodiment of the disclosure.

DETAILED DESCRIPTION OF THE EXAMPLE EMBODIMENTS

Figure 1:
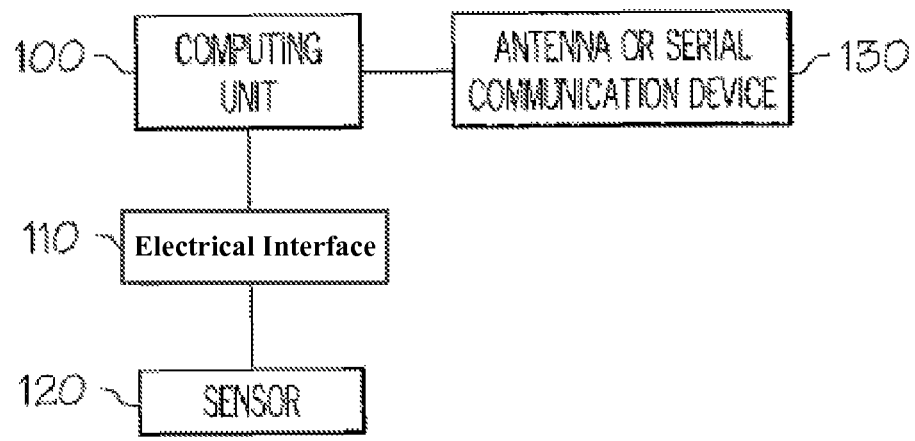
FIG. 1 is a block diagram presenting a system level view of the athletic performance measuring unit in accordance with one exemplary embodiment of the disclosure.

Exemplary embodiments will now be described more fully hereinafter with reference to the accompanying drawings, in which exemplary embodiments are shown. The concepts disclosed herein may, however, be embodied in many different forms and should not be construed as limited to the exemplary embodiments set forth herein; rather, these embodiments are provided so that this disclosure will be thorough and complete, and will fully convey the scope of the concepts to those skilled in the art. Like numbers refer to like, but not necessarily the same or identical, elements throughout. Turning now to the drawings, in which like numerals indicate like elements throughout the figures, exemplary embodiments are described in detail. As would be recognized by a person of ordinary skill in the art having the benefit of the present disclosure, the claimed invention may be embodied in many different forms and should not be construed as limited to the exemplary embodiments depicted and described herein.

The present disclosure is directed to systems, methods, and apparatus to track one or more parameters of performance for one or more athletes, animals, motorized vehicles, athletic support products, toys, or other products in any sport or other activity and deliver real-time or near real-time data on personal computing devices such as generic Personal Processing Units (PPUs), which may include, but are not limited to, a laptop computer, a personal computer, a smart device (e.g., smart phone, smart tablet, smart watch, smart television, smart desk, smart wall, smart display, smart video board/scoreboard, etc.), another mobile device, such as a digital assistant, personal digital assistant (PDA), mp3 player or other audio players, cell phone, pager, beeper, radio, portable television, portable DVD player, other video playing device, calculator, watch, etcetera, and/or non-personal computing devices such as networked computers, broadcast TV, display devices at arenas, stadiums, fields, or other locations where the athlete is participating and/or the athletic performance measuring unit is located, or one or more social or other forms of web server/website. In one example embodiment, an athlete performance measuring unit measures one or more performance parameters for an athlete or other animal or object to which the unit is coupled or integrated into and can be configured to upload or transmit that data from the onboard sensor system of the athlete performance measuring unit to one or more of the PPUs, (e.g., a laptop computer, a personal computer, a smart device, another mobile device, such as a digital assistant, PDA, mp3 player or other audio players, cell phone, pager, beeper, radio, portable television, portable DVD player, other video playing device, calculator, watch, etc.), and/or non-personal computing devices such as a networked computer, web server, broadcast TV, display devices at arenas, stadiums, fields, or other locations where the athlete is participating and/or the athletic performance measuring unit is located, or one or more social or other forms of website.

Examples of the athletic performance parameters to be transmitted by the athletic performance measuring unit include, but are not limited to, acceleration, cadence, distance, GPS, vertical leap, heart rate, pace, pressure, contact, speed, swing plane, temperature, time, and many more. In one example embodiment, the data is transmitted in real-time or near real-time from the athlete performance measuring unit to a main personal processing unit (PPU) (e.g., smart device, digital assistant, PDA, mp3 player or other audio player, cell phone, pager) that has the ability to transmit or download the sensor information to other personal (e.g., PPUs) and non-personal (e.g., network computers, web servers, video displays, etc.) devices. In certain example embodiments, the PPU is an athletic performance parameter dedicated on non-dedicated computing device that is empowered to download the performance data as described above. In one example embodiment, the PPU is similar to a PDA, smart phone, tablet, cell phone, or mp3 player in size and carries within it software that is capable of receiving and processing the sensor data received from the athlete performance measuring unit. Then the athletic parameter that has been so measured, processed, and recorded in an onboard memory unit can be transmitted to other personal and/or non-personal computing units if so desired by the owner of the PPU inputting a set of keystrokes, button pressing, or touching the screen if the PPU is so equipped.

Hereinafter, the athlete performance measuring unit will be described with reference to an example athletic performance measuring unit that, in certain exemplary embodiments, measures one or more athletic performance parameters (e.g., the vertical displacement (or height) or horizontal displacement (length) that occurs when an athlete or animal (e.g., dog, horse, etc.) jumps; when the vehicle, such as a bicycle, motorcycle, motorcross bike, all-terrain vehicle, three-wheeler, four-wheeler, skateboard, pogo stick, snowboard, scooter, windsurfing board, kite surfing board, skis, surfboard, snowmobile, automobile (e.g., rally sport cars), or other similar device; the animal collar, harness, or saddle; or the ball, toy, or any other product to which the unit is coupled or integrated in is caused to be jumped by the athlete or animal. However, the use of the term athletic performance measuring unit hereinafter is for example purposes only and shall not be read as limiting the scope of the athletic performance parameters capable of being measured by the example athletic performance measuring unit as those of ordinary skill in the art will recognize that many other athletic performance parameters may be measured by the athletic performance measuring unit and each parameter should be read into the following disclosure as if expressly disclosed therein.

FIG. 1 is a block diagram presenting a system-level view of the example athletic performance measuring unit in accordance with one exemplary embodiment of the disclosure. Referring now to FIG. 1, the exemplary athletic performance measuring unit can be integrated within or on an article of clothing such as a shoe, glove, wrist band, belt, strap, hat, shorts, cap, shirt, sports bra, underwear, helmet, pads, pants, or other such clothing item known to those of ordinary skill in the art. In one example, the athletic performance measuring unit system can include a computing unit 100 (such as a controller, microcontroller, ARM microcontroller or other type of processor). The computing unit 100 can communicate, for example, over an electrical interface 110 or other electrical interface with a sensor device 120. In certain example embodiments, the computing unit 100 also includes within itself a short-term memory. Additionally, an antenna 130 that transmits some form of electromagnetic radiation is connected to and/or electrically or communicably coupled with the computing unit 100. In certain example embodiments, the computing unit 100 monitors the athletic performance parameters, via the electrical interface 110 (which can include, for example, a serial, parallel, Bluetooth, USB, I2c, generic bus or other type of bus), that are being measured utilizing the sensor 120. Examples of the sensor 120 include but are not limited to, a magnetometer, an accelerometer, a gyroscope, radio transmitting and/or receiving circuitry, a vibration motor, an ultrasonic sensor, an infrared sensor, a buzzer, a speaker, a microphone, a global positioning system (GPS), a pressure sensor, an optical or other light sensor, and a piezo element. Examples of the athletic performance parameters to be measured include, but are not limited to, acceleration, cadence, distance, GPS, vertical leap, vertical touch height, heart rate, pace, pressure, contact, speed, swing plane, temperature, time, a generic athletic performance parameter and many more.

For example, once the computing unit 100 senses some real-time data, the unit 100 has the capability to process that data in real-time or near real-time as well as to process the data to obtain desirable quantities, for example, peak performance data such as the maximum height having been jumped by an athlete, the vertical touch height for the particular athlete, the average jump height for the particular athlete, the number of jumps made by a particular athlete, etc. The computing unit 100 may also be configured to provide period data for configurable extended periods of time such as 1, 5, 10, 20, 30, and 60 second intervals as well as any interval between one minute and ninety minutes. All of this information can be transferable from the computing unit 100 via the antenna 130 to another personal computing device (e.g., a PPU, such as a smart device) or onto a network, web server or other non-personal devices (not shown). In one example, the antenna unit 130 can be configured to communicate via Bluetooth technology, radio frequency or any other wireless method to a PPU or non-personal computing device and/or alternatively communicates through a USB mechanical connection. In another alternative, the computing unit 100 can communicate via Wi-Fi, over the air (OTA), or another type of electromagnetic communication to a PPU (e.g., a smart device) or non-personal computing device (e.g., networked web server, network computer, the Internet, etc.) as described below. Electrical power for the athletic performance measuring unit can be provided either from a plug socket in the article of clothing or from one or more batteries contained in the athletic performance measuring unit and can provide the necessary power to operate the computing unit 100, the electrical interface 110, the sensor 120 and/or the antenna 130.

Figure 2:
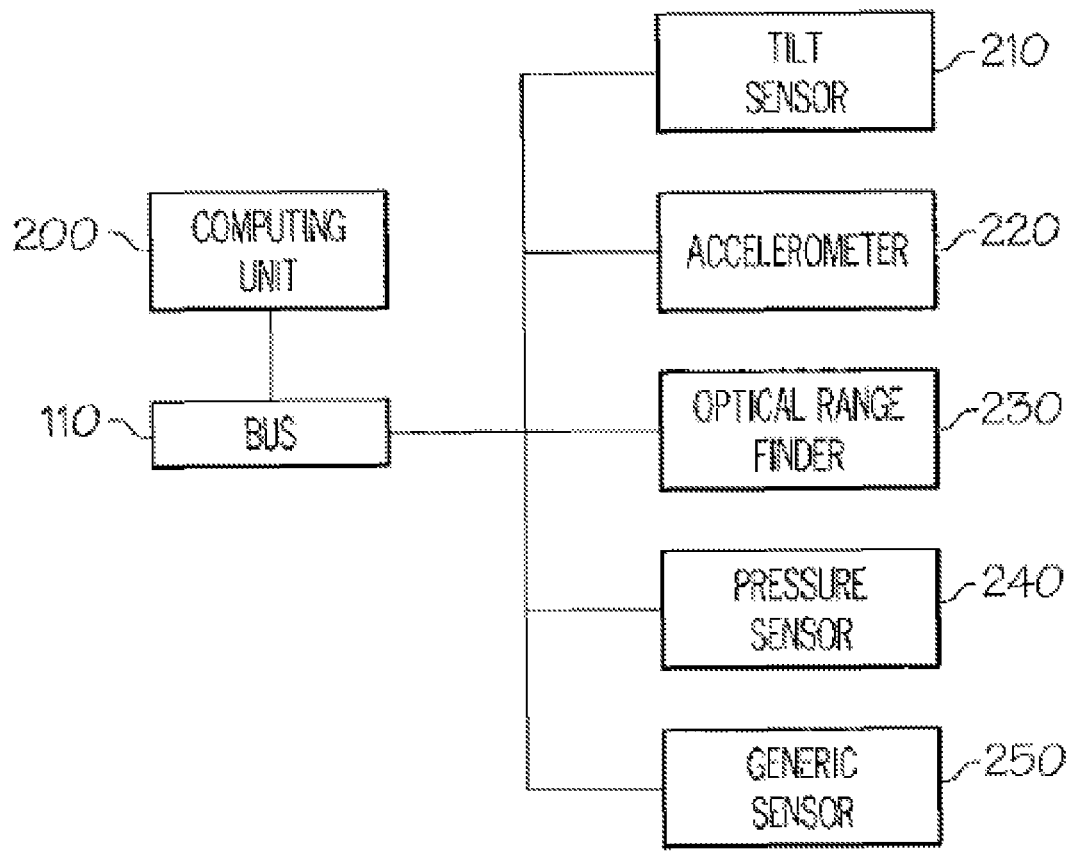
FIG. 2 is a block diagram presenting a graphical illustration of the example sensors that singly or in any combination may be included in the athletic performance measuring unit in accordance with one exemplary embodiment of the disclosure.

FIG. 2 is a block diagram presenting a graphical illustration of the example sensors that singly or in any combination may be integrated into the athletic performance measuring unit or an article of clothing such as a shoe, glove or similar item and/or communicably coupled to the athletic performance measuring unit in accordance with one exemplary embodiment of the disclosure. Now referring to FIG. 2, the athletic performance measuring unit may include a computing unit 200 that is integrated into the article of clothing or that is configured to be attached to the article of clothing or another device used by the athlete or animal (e.g., a dog wearing a shirt) while taking part in an activity. The computing unit 200 is capable of communicating with, and can be communicably coupled to a variety of different types of sensor units. Just a few examples of the sensor units 210-250 that computing unit 200 is able to communicate with are shown in FIG. 2. These, include but are not limited to, a tilt sensor 210, an accelerometer 220, an optical range finder 230, a pressure sensor 240, and a generic sensor 250. Other types of sensor that the computing unit 200 is able to communicate with can include, but are not limited to, laser, laser diode, and sound sensors. In this disclosure, the words 'integrated' or 'onboard' when used in connection with the disposition of items on the clothing are used interchangeably and mean that there is a unit that has been placed in the ordinary surface or interior of an item so as not to cause undue distortion of the article of clothing's ordinary purpose. In certain example embodiments, the athletic performance measuring unit may remain integrated into the article of clothing and can be washed with the article of clothing without damaging or affecting the performance capabilities of the athletic performance measuring unit. In another example embodiment, the sensors may have internal Wi-Fi or other wireless capability and may communicate directly with a PPU, such as a smart device, to provide sensor data for use/calculation by the PPU. Additionally, in certain example embodiments, the onboard computing unit 200 is detachable from the article of clothing and modularized as taught with reference to FIG. 3.

Figure 3A:
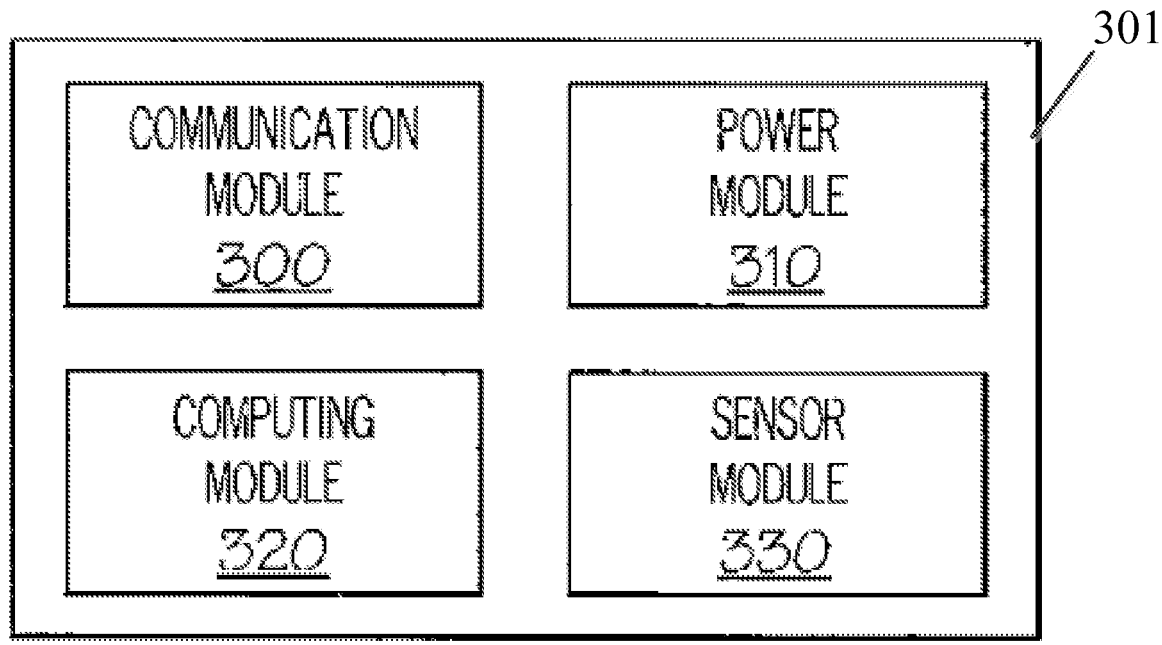
FIGS. 3A and 3B are block diagrams presenting a graphical representation of example sets of modularization choices for use with the athletic performance measuring unit in accordance with one exemplary embodiment of the disclosure.
Figure 3B:
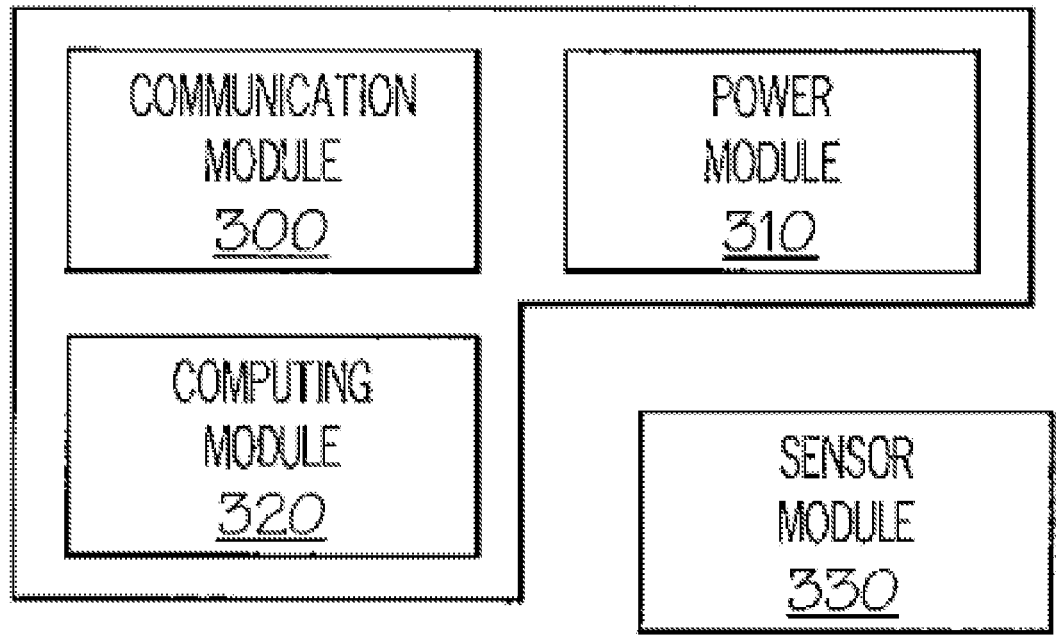

FIGS. 3A and 3B are block diagrams presenting a graphical representation of example sets of modularization choices for use with the athletic performance measuring unit 301 in accordance with one exemplary embodiment of the disclosure. Referring now to FIG. 3, the athletic performance measuring unit 301 may include or may be embodied by a detachable modularized system whereby the entire athletic performance measuring unit 301 may be removed from the article of clothing so as to make use of the athletic performance measuring unit 301 in, on, or alongside another article of clothing. In one embodiment, the hardware for the athletic performance measuring unit 301 that is modularized includes four main modules: a communication module 300, a power module 310, a computing module 320, and a sensor module 330. In certain example embodiments, two or more modularization configurations may be provided. FIG. 3A shows an example of the athletic performance measuring unit 301, wherein all four main modules 300-330 are selectively detachable as one large module. FIG. 3B shows an example of the athletic performance measuring unit 301, wherein the communication 300, power 310, and computing 320 modules are detachable as one module, while the sensor module 330 remains in, on, or alongside the article of clothing or device used by the athlete, animal, or another device used by the athlete.

Figure 4:
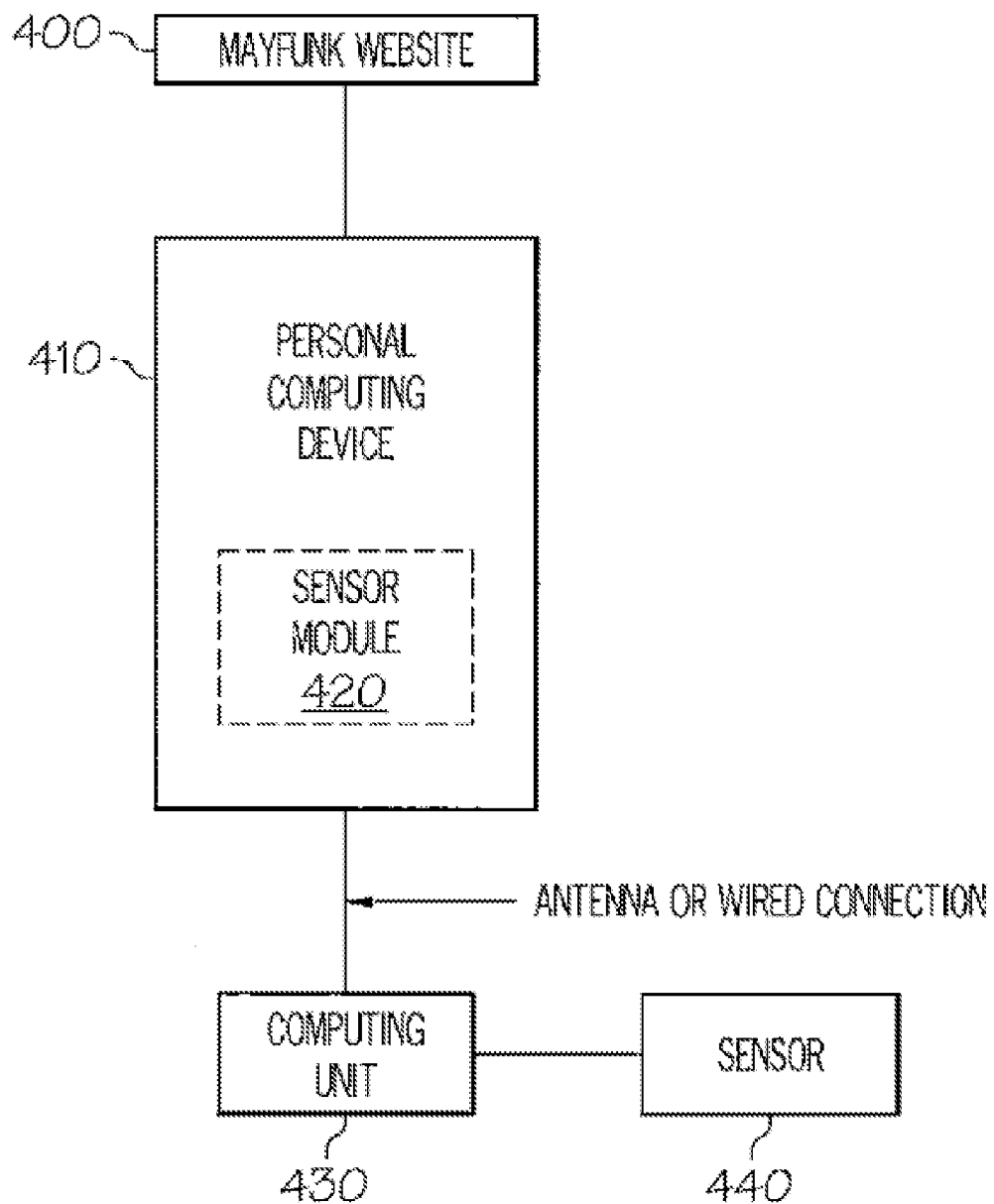
FIG. 4 is a block diagram presenting an example high level illustration of a sports-themed website utilized in coordination with the athletic performance measuring unit in accordance with one exemplary embodiment of the disclosure.

FIG. 4 is a block diagram presenting an example high level illustration of a sports-themed web server 400 utilized in coordination with the athletic performance measuring unit in accordance with one exemplary embodiment of the disclosure. For example, FIG. 4 depicts a social web server 400 (Mayfunk.com for example) presented and configured so that amateur or professional athletes in one or more sports are provided with a shared medium to share, compare, socialize, or compete utilizing specific details, such as athletic performance parameters, related to their sports. In certain examples, the web server 400 may also be configured to provide the ability for coaches and or scouts to search for athletes, including those located in major metropolitan areas, minor markets, and/or virtually anywhere on the globe. Additionally, the web server 400 can be configured so that professional and amateur athletes can set up a personal page on the web server 400 that is displayed on the website associated with the web server 400, where the athletes are able to display and/or broadcast their personal and statistical information (including, but not limited to, athletic performance parameters), videos such as YouTube and other audio/video performances. The example web server 400 may be configured to allow athletes from around the world to be able to judge their own performance and determine (according to their age, region, state, country, etc.) where they are in accordance to their performance "bar" for that particular sport or athletic maneuver.

In one example embodiment, a sensor module 420 is loaded into and/or communicably coupled to a personal computing device 410 (otherwise known as a personal processing unit PPU elsewhere in this disclosure). The sensor module 420 is programmed to collect and transmit data, such as athletic performance parameters, to the web server 400 where the information is received, processed, and visually presented on the web server 400. For example, a sensor 440 measures sensor data, such as a quantifiable athletic performance parameter, that is transmitted via an electrical interface (not shown) and read into the computing unit 430 that is onboard the article of clothing and/or other device used by the athlete or animal. This computing unit 430 transmits the sensor data to a personal computing device PPU 410 that processes the sensor data utilizing the sensor module software 420. Additionally, if the owner of the PPU 410 so desires, he or she may forward the athletic sensor data to the Mayfunk website 400 with a few keystrokes, button presses, or touch screen commands.

Figure 5:
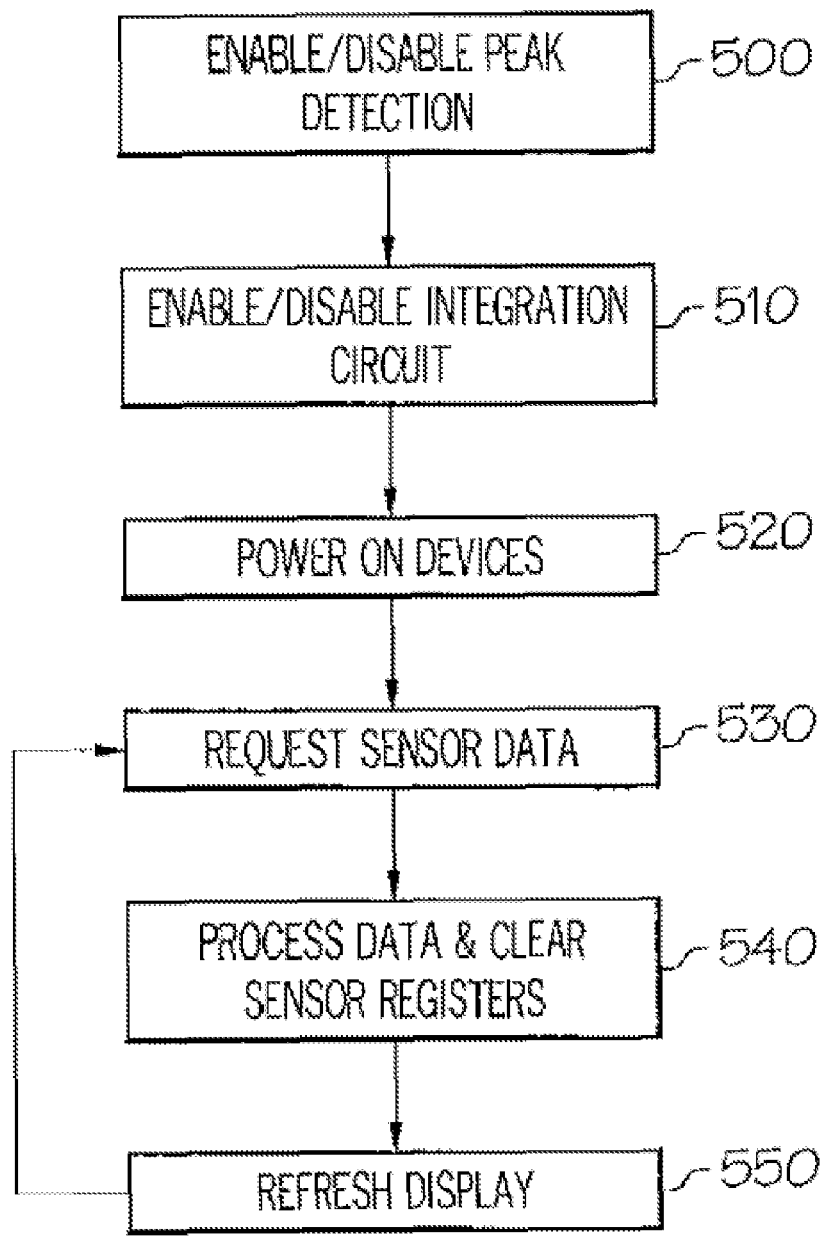
FIG. 5 is a flowchart presenting an example method of operation of the athletic performance measuring unit in accordance with one exemplary embodiment of the disclosure.

FIG. 5 is a flowchart presenting an example method of operation of the athletic performance measuring unit in accordance with one exemplary embodiment of the disclosure. In certain example embodiments, the athletic performance measuring unit itself and/or the article of clothing or other device used by the athlete may each or at least one may contain on/off buttons and one or more mode buttons to set the different scaling functions accessible from the onboard sensors communicably coupled to the athletic performance measuring unit. Referring now to FIGS. 1, 4, and 5, the example method can start up either through pressing an on switch located on the article of clothing or other device used by the athlete and communicably coupled to or physically located on the housing of the athletic performance measuring unit of FIG. 1, or through the inputting of commands to start the sensor data collection utilizing a PPU, such as personal computing device 410. The PPU 410 or the buttons on the article of clothing or other device used by the athlete or on the housing of the athletic performance measuring unit can transmit a command to the computing unit 100 integrated into or attached to the article of clothing or other device used by the athlete to commence ordinary operations. For example, at the start of ordinary operation, the software of the computing unit 100 can be configured to enable peak detection 500 in the event that the appropriate button(s) have been pressed on the article of clothing or other device used by the athlete, on the housing of the athletic performance measuring unit, or by way of receipt of a command(s) from the PPU 410; otherwise, this function can be disabled. In one example, peak detection 500 indicates the top-most measurement received by the computing unit 100 from the sensor 120 for each particular athletic performance parameter, such as jump height, touch height, jump length, temperature, breathing rate, and many other parameters that are amenable to this scaling of values.

In step 510, the integration circuit is enabled so as to integrate the values that are being sensed in the event that the appropriate button(s) have been pressed on the article of clothing or other device used by the athlete, on the housing of the athletic performance measuring unit, or by way of receipt of a command(s) from the PPU 410; otherwise, this function is disabled. In certain example embodiments, the integration circuit may also include summing circuits or various other data shaping and analysis equations. While steps 500-510 have utilized peak and integration circuits, this is for example purposes only and it should be understood that this is only a particular exemplary combination. A more generalized example of the method of FIG. 5 can include a generic summation function alone or in combination with a detection circuit. Further extending this concept allows for the inclusion of one or more other summation and or detection circuitries. After the integration circuits have been enabled in step 510, the athletic performance measuring unit is powered on in step 520, meaning that the sensor unit 120 is powered on via communication over electrical interface 110. Alternatively, the athletic performance measuring unit remains on and begins its operation method when it connects via a wireless or wired signal to the PPU 410. In one example, the computing unit 100 requests sensor data utilizing electrical interface 110 to communicate with the sensor unit 120 in step 530. Alternatively, instead of a pull system, the sensor unit 120 may push sensor data to the computing unit 100 via the electrical interface 110 anytime it is senses an activity. In another alternative, the sensor unit 120 may push sensor data directly to the PPU 410. When the computing unit 100 receives sensor data across the electrical interface 110, the sensor data is processed in step 540 by, for example, the onboard computing unit 100. Alternatively, the sensor data is transmitted to the PPU 410 and the sensor data is processed in step 540 by for example, the PPU 410 (e.g., via an application stored or provided through the PPU 410). In another alternative embodiment, the sensor data is transmitted to a non-personal computing device (e.g., a network computer or web server) and the sensor data is process in step 540 by the non-personal computing device. After receiving the sensor data, the computing unit 100 and/or the sensor unit 120 may also clear sensor registers to await the next data value. In step 550, the routine refreshes a display (such as an LCD, LED, or OLED display) to display the processed data value so that the athlete wearing the article of clothing or using the device that the athletic performance measuring unit is integrated into or attached to can view the most recent athletic performance parameter data sensed by the sensor unit 120. In one example embodiment, the method of FIG. 5 continues indefinitely as long as power is supplied to the various components or until a PPU 410 transmits a stop command to the athletic performance measuring unit or an off button is pressed by the athlete on the article of clothing, other device used by the athlete, or on the housing of the athletic performance measuring unit that is communicably coupled to the athletic performance measuring unit, to transmit a stop command.

Figure 6:
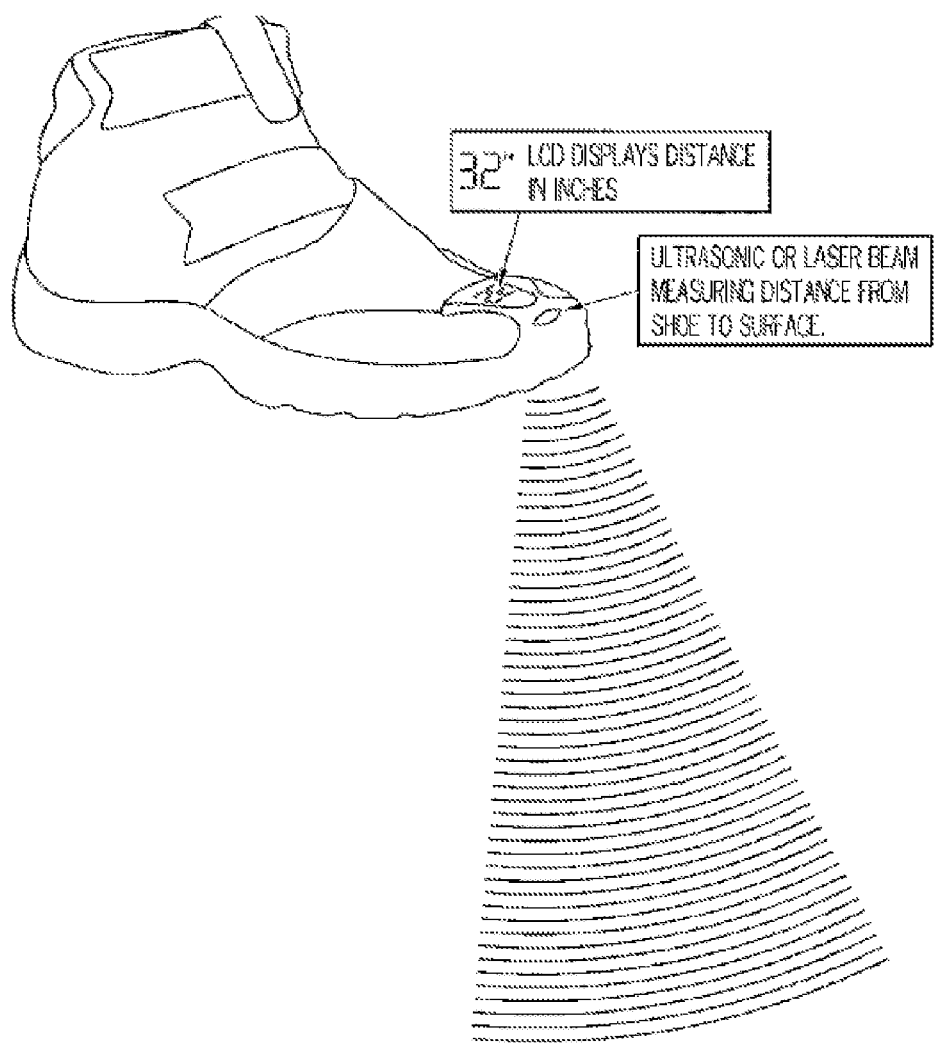
FIG. 6 is a graphical representation depicting one type of athletic shoe that incorporates the athletic performance measuring unit into the shoe itself in accordance with one exemplary embodiment of the disclosure.

FIG. 6 is a graphical representation depicting one type of article of clothing, in this case an athletic shoe, that incorporates the athletic performance measuring unit on the shoe itself in accordance with one exemplary embodiment. While FIG. 6 depicts a shoe as an article of clothing, in other example embodiments any article of clothing incorporating the athletic performance measuring unit (which may include an embedded sensor and modularized processing unit along with the associated power, antenna, and electrical interface needed to facilitate the measurement of one or more athletic parameters) may be used. Now referring to FIG. 6, the example shoe includes an electromagnetic sensor, such as a laser or ultrasonic sensor unit, on the sole of the shoe. However, neither the location of the sensor on the shoe nor the type of sensor should be viewed as limiting since there are a variety of locations for the sensor to be disposed upon an article of clothing. For example, when the article of clothing is a glove, the glove may have the sensor embedded on the middle part of a finger in the event that it is grasping a golf club whilst a sensor may be placed at the bottom of an athlete's small finger in the event he or she is grasping a baseball bat. In one example embodiment, the jump data (and/or continuous motion data) will be displayed in real-time or near real-time on the athlete's shoe via LCD, LED, OLED, or other types of displays and can in certain example embodiments also incorporate wireless technology between the sensors 120, the computing unit 100, the PPU, and/or the display.

Figure 7:
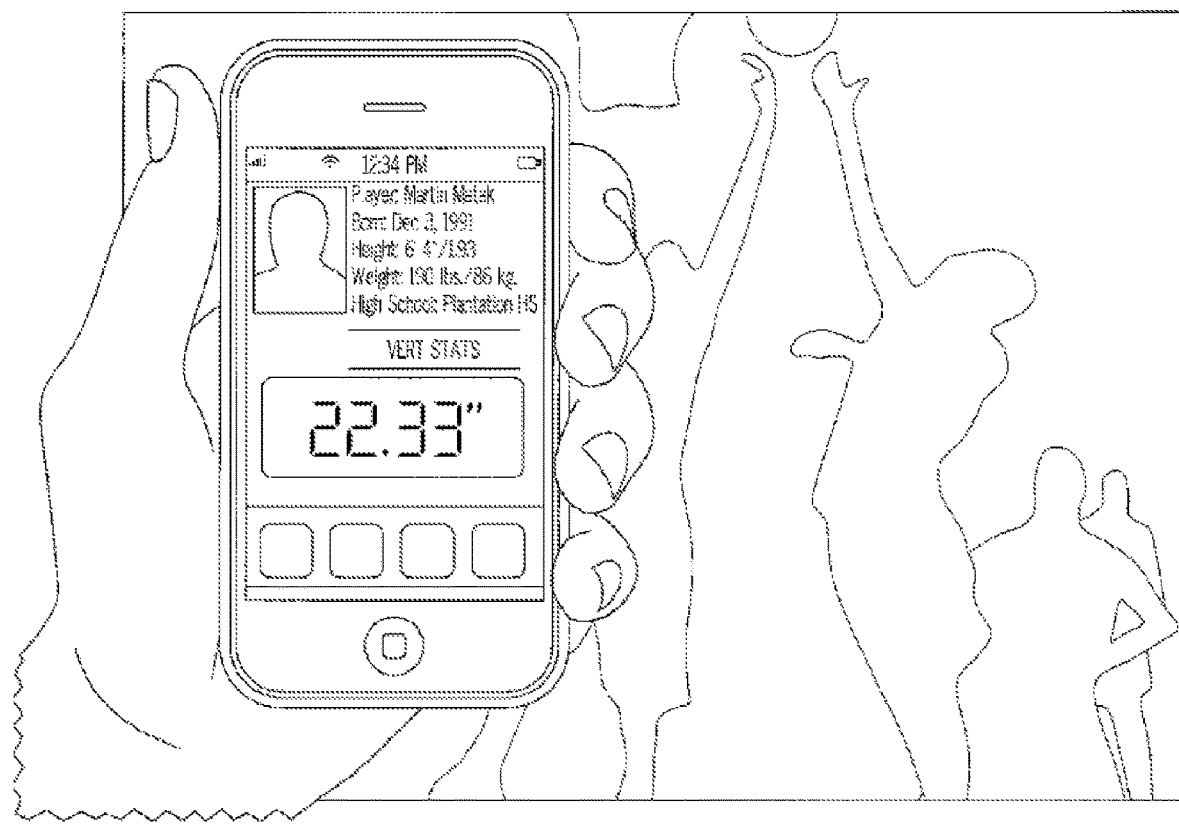
FIG. 7 is a graphical representation depicting the vertical measurement that was measured by and received from the example athletic performance measuring unit transmitted to and displayed on a remote personal computing device in accordance with one exemplary embodiment of the disclosure.

FIG. 7 is a graphical representation depicting the vertical measurement data that was measured by and received from the example athletic performance measuring unit and transmitted to and displayed on a remote PPU, such as a smart device shown at 410 of FIG. 4 in accordance with one exemplary embodiment of the disclosure.

Figure 8:
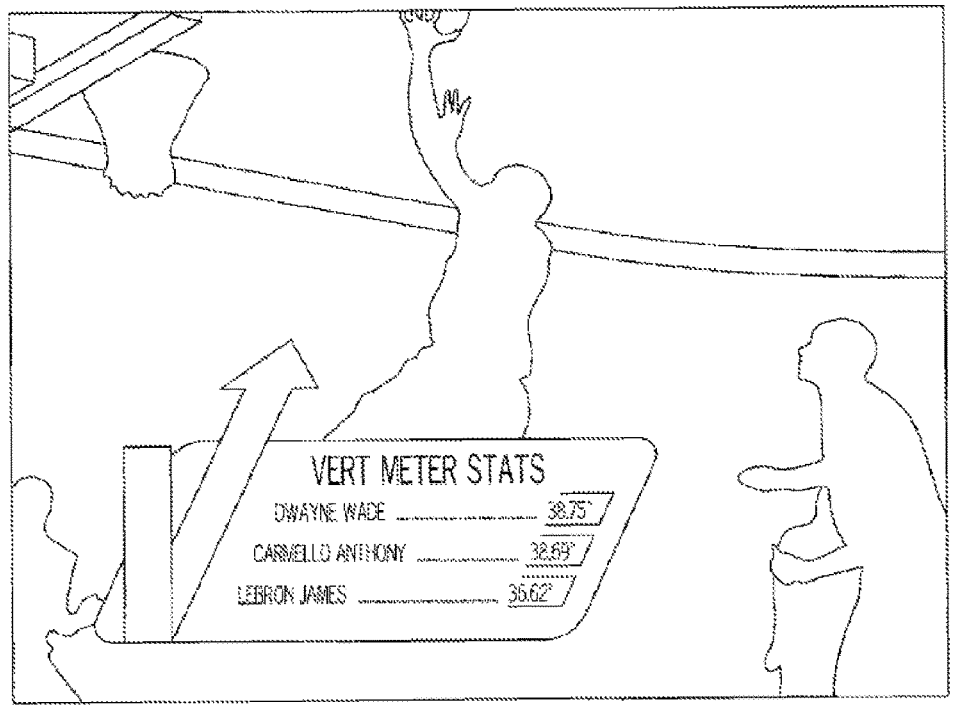
FIG. 8 is a graphical representation of vertical jump heights received from multiple athletic performance measuring units and displayed on a remote personal computing device or web server in accordance with one exemplary embodiment of the disclosure.

FIG. 8 is a graphical representation of the maximum or peak vertical jump heights received from multiple athletes each associated with a different athletic performance measuring unit and displayed on a remote personal computing device (such as the PPU of 410 of FIG. 4) or web server in accordance with one exemplary embodiment of the disclosure.

Data Transmission Examples a. Sensor to device: sensor in or communicably coupled to the vertical measuring device transmits data to an external device, for example, a PPU (e.g., a laptop computer, a personal computer, a smart device, another mobile device, such as a digital assistant, PDA, mp3 player or other audio players, cell phone, pager, beeper, radio, portable television, portable DVD player, other video playing device, calculator, watch, etc). The athletic performance measuring unit can be incorporated into or coupled to an article of clothing (e.g., a shoe, hat, wrist guards, belt, strap, shirt, pants, gloves, socks, shorts, helmet, undergarments etc.) for an athlete. The athlete can measure his or her performance by the sensor of the unit measuring one or more athletic performance characteristics and the athletic performance measuring unit can transmit this sensor data to the athlete's PPU as well as viewing this data on, for example, an LCD, LED, or OLED display of the athletic performance measuring unit. In certain example embodiments, the data displayed on the display can also be stored in the unit and/or on the PPU of the athlete.

b. The athletic performance measuring unit receives sensor data at the sensor and transmits the sensor data to a receiver to be broadcast on television. In this case, the athletic performance measuring unit transmits the sensor data to a receiver located near the field of play for the athlete. In one example, the sensor data is a specific athletic parameter (e.g., jump height, number of jumps, average jump height, touch height, jump length, etc.) being measured in real-time or near real-time for viewing at home on a television broadcast of the athletic event, via the PPU of any fan located at the athletic event, at home, or anywhere else where the PPU is able to receive data, or in a stadium/arena or other locale of the athletic event (e.g., on the scoreboard or another video display). In addition, in certain example embodiments, these measurements can be coupled with or presented along-side or with a specific sponsor endorsement to be used in an advertisement as the statistics are displayed in real-time or near real-time or as the game and player results are broadcast during the event.

c. Sensor data from the athletic performance measuring unit is uploaded to a web server. In this case, sensor data and/or calculated performance parameters (e.g., jump height, number of jumps, average jump height, touch height, jump length, etc.) can be transmitted or uploaded to a web server for a social website for athletes or any other website. The sensor data can be received by the web server directly from one or more of the sensors, from the athletic performance measuring unit, from the PPU of the athlete (e.g., via a mobile application on the smart device of the athlete), and/or from a non-personal computing device. The sensor data can be displayed on the website in many different formats, such as, for example, a historical display (displaying multiple outputs of sensor data over a user configurable historical time period), a comparative display (comparing sensor data received from one athletic event against sensor data received from one or more other athletic events), an average of the sensor data values received from one or more athletic events, a modification of the sensor data received based on one or more attributes of the athlete (e.g., calculating a touch height for an athlete based on the received sensor data for a jump height and based on one or more physical attributes of the athlete (such as the measured height of the athlete with one arm or both arms extended in the air). In this example, the athlete can compete with peers, socialize, analyze his/her performance "bar" data, and compare data results from previous performances and peers at the social website for athletes or another website where the sensor data is uploaded and displayed.

Figure 9:
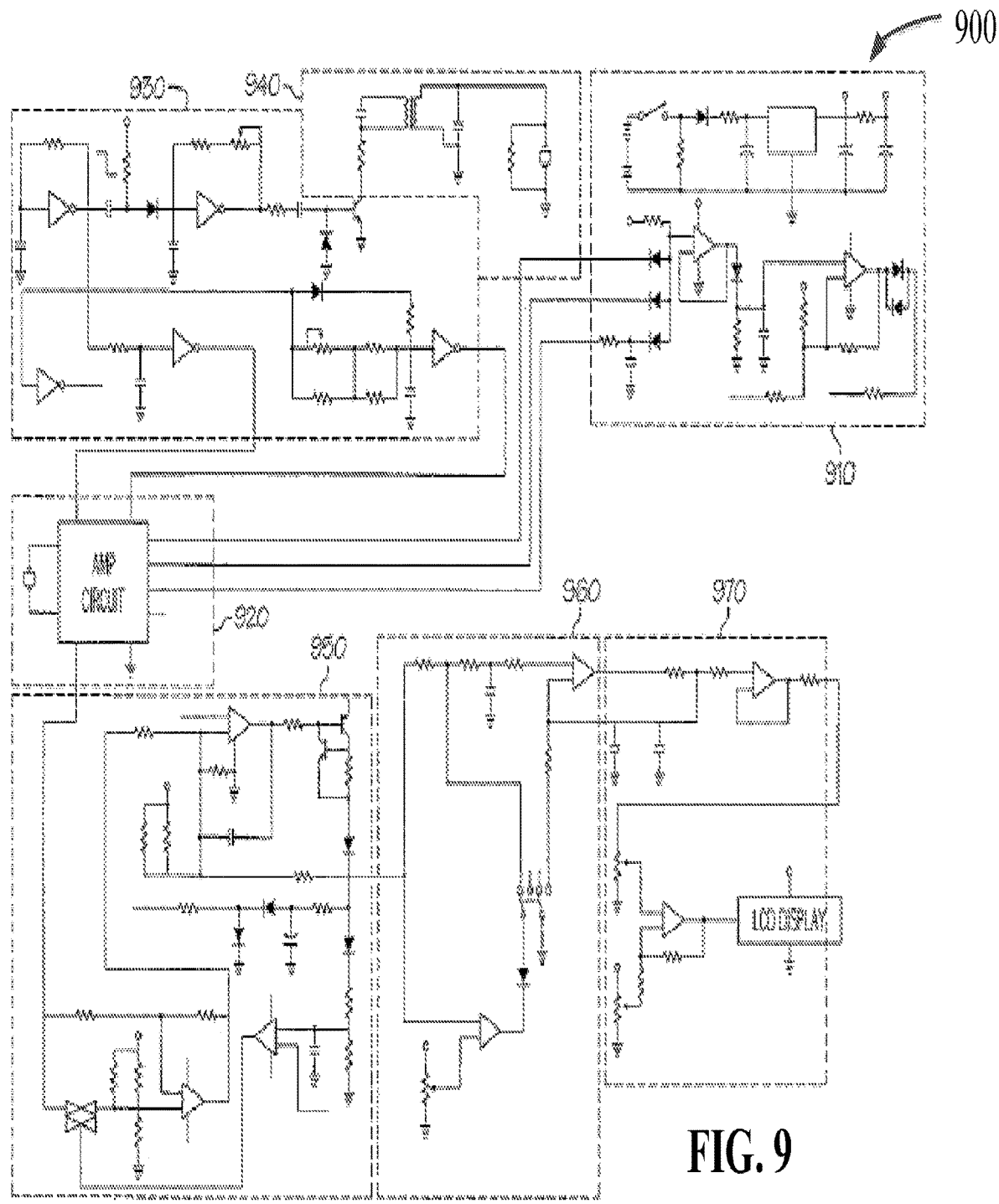
FIG. 9 is a circuit diagram presenting one possible electronic circuit for the athletic performance measuring unit in accordance with one exemplary embodiment of the disclosure.

FIG. 9 is a circuit diagram presenting one possible electronic circuit 900 for the athletic performance measuring unit in accordance with one exemplary embodiment of the disclosure. Referring to FIG. 9, the example circuit 900 can include seven basic sub-circuits including: 1) a Power Supply Sub-circuit; 2) a Pulse Timing Sub-circuit; 3) a Pulse Filtering Sub-circuit; 4) a Transmitter Sub-circuit; 5) a Detection Conditioning Sub-circuit; 6) a Peak Detection Sub-circuit; and 7) a Distance Readout Sub-circuit. In the example circuit 900, there are two ultrasonic sensors in use. One ultrasonic sensor is used as a speaker, which can send out short pulses or ultrasonic waves with a preferred frequency. The second ultrasonic sensor acts as a microphone and listens for any reflected ultrasonic signals. The AMP CIRCUIT uses properties of the discharge timing of an RC circuit to record a time delay as a voltage difference. For example, the longer the time, the larger the voltage difference that is being compared. If the circuit waits too long, the internal voltage in the RC circuit drops below some minimum threshold, and the timing circuit resets itself and sends out the next pulse. The rest of the circuitry includes additional electronics to either condition the voltages for output or display.

Examples of each of the aforementioned sub-circuits are now described below. The power supply sub-circuit 910 can provide on-board battery backed power and regulated voltages for operation. The pulse timing sub-circuit 920 can measure time delay from between pulse transmission and reception. The output can include short voltage pulses to the pulse filtering sub-circuit 930 to initiate a timing sequence while the input can include a voltage signal on an ultrasonic receiver. In one example, the timing sequence completes when input voltage at the ultrasonic receiver is high enough. A new timing sequence can be initiated either when an input voltage is recorded or a timeout condition is reached.

The pulse filtering sub-circuit 930 can condition the timing pulse from the pulse timing sub-circuit 920 as an acceptable input to transmitter sub-circuit 940. The transmitter sub-circuit 940 can set the operational frequency and emit an ultrasonic beam. In one example, the pulse filtering sub-circuit 930 takes a conditioned timing pulse as an input. Once a timing sequence completes in the pulse timing sub-circuit 920, a voltage signal corresponding to a time delay is passed to the detection conditioning sub-circuit 950 for conditioning into a distance measurement. The peak detection sub-circuit 960 is an optional sub-circuit that will hold the highest recorded value of one or more athletic performance parameters. This circuit 960 can be controlled via a physical switch, such as the button 1445 of the athletic performance measuring unit 1400, that can be used to disable or reset the peak value back to zero. In the distance readout sub-circuit 970, an input voltage is re-scaled as input for the dedicated LCD, LED, or OLED readout electronics.

Below of examples of athletic bundles and/or athletic performance parameters that may be sensed/calculated by the athletic performance measuring unit in accordance with one or more example embodiments of the disclosure, including the example embodiments discussed in FIGS. 1-3B, and 14. The example components presented below do not disparage the use of other devices or components. For example, the citing of a lithium battery as a power source for the athletic performance measuring unit is not limiting in the type of power source that may be used for the same or other athletic bundles.

Basic Athletic Activity Examples:
Basic Jump Measurement Configuration
Activity Specific Sensors: Athletic performance monitoring unit clipped to or integrated into a waistband, clipped to or integrated into the back of a sports bra, inserted or integrated into a belt or other article of clothing, such as a waist belt, shorts, shirts, bra, hat, pants, swimsuit, shoes, socks, underwear, clipped to or integrated into a collar, harness, or saddle to be attached to an animal, or taped on to the athlete's body using tape, such as kinesio tape or medical tape Inertial measurement unit that may contain accelerometers, gyroscopes, and/or magnetometers Communication Module: Bluetooth 4.0, Wi-Fi, and/or OTA for real-time, near real-time and/or delayed data transfer; graphical display that may include an LED, LCD or OLED display Power Module: Lithium ion rechargeable battery that can be attached or integrated into the athletic performance measuring unit.

Basic Integrated Shoe Jump Measurement Configuration:
Activity Specific Sensors: Instrumented shoes
Embedded range finding technology for vertical jump calculation
Accelerometers for lateral movement
Can include start/stop/reset buttons for interacting with the computing unit
Computing unit: Snaps onto back or side of shoe
Communication Module: data logger or LED Display attached and/or communicably coupled to the computing unit
Power Module Lithium Battery electrically coupled to the computing unit.

Basic Extreme Sport Configuration:
Activity Specific Sensors—Bicycle/BMX/motorcross/skateboard/scooter/snowboard/skis/surfboard/windsurfing board/kite surfing board/rally sport cars Computing Unit—Attached to or integrated into (in case of bicycle/BMX/motorcross) handlebar/seat/post/bike frame or attached to or integrated into (in the case of a skateboard/scooter/snowboard/windsurfing board/kite surfing board/surfboard/skis) trucks, rail, any flat surface, skateboard deck, snowboard deck, surfboard deck, wind surfing board deck or sail mast, kite surfing board deck, ski shoes, skateboard truck, bicycle frame, seat, post handle bar, or handle bar or other bike/BMX/motorcross stem or anywhere within the rally sport car Communication Module: Bluetooth 4.0, Wi-Fi, and/or OTA or data logger for real-time, near real-time and/or delayed data transfer; graphical display that may include LED, LCD, or OLED display coupled to or wirelessly attached and communicably coupled to the athletic performance measuring unit Power Module: Lithium battery attached and/or electrically coupled to the athletic performance measuring unit.

Basic Golf Bundle:
Activity Specific Sensors: Instrumented clubs, gloves
Glove: Athletic performance measuring unit clipped to back of the golf glove or integrated into the golf glove
Embedded palm and fingertip pressure sensors for grip information.
Includes start/stop/reset buttons for communication with computing unit.
Club: Athletic performance measuring unit clipped to the golf club or integrated into the golf club; embedded accelerometer and pressure sensors in club head for golf swing and ball strike data
Club handle provides a wired or wireless connection to glove. The example wired connection uses a magnetic coupling, so that if the grip is released on the club the wired connection can disengage without causing damage or injury (could be extended with additional sensors into an advanced training package to provide feedback on stance and club grip).
Embedded compass for club face direction data.
Computing unit: Snaps onto back of glove and/or integrated into any one of the glove, club shaft, club head, or club handle.
Communication Module: Bluetooth 4.0, Wi-Fi, and/or OTA or data logger for real-time, near real-time and/or delayed data transfer attached and/or communicably coupled to the computing unit
Power Module Lithium Battery electrically coupled to the computing unit.
Basic Cycling Bundle:
Activity Specific Sensors: Bicycle accessory pack
RPM sensor attached to bicycle tire
Tilt sensor for incline telemetry
GPS for location, personal heart rate monitor with magnetic coupling to prevent injury or damage in case of a fall
Includes handlebar start/stop/reset buttons communicably coupled to the athletic performance measuring unit/with the computing unit 100.
Athletic performance measuring unit: attached, integrated, or removably coupled to the bicycle on handlebar, bike stem, or other portion of the bicycle
Communication Module: Bluetooth 4.0, Wi-Fi, and/or OTA or data logger for real-time, near real-time and/or delayed data transfer attached and/or communicably coupled to the athletic performance measuring unit.
Power Module Lithium Battery attached to computing unit
Basic Running Bundle:
Activity Specific Sensors: Arm band unit, RF shoe pod
GPS Heart Rate Monitor, using magnetic couplers radio receiver antenna to communicate with shoe pod control buttons to use with computing unit
Shoe Pod: accelerometer for stride cadence information pressure sensor for footfall radio transmitter on/off switch
Computing unit: Attached or integrated into arm band or any other piece of clothing.
Communication Module: Bluetooth 4.0, Wi-Fi, and/or OTA or data logger and/or LED, LCD, OLED display or wireless communicably coupled to the athletic performance measuring unit
Power Module: Lithium Battery electrically coupled to the unit armband.

Basic Curling Bundle:
Activity Specific Sensors: shoes, glove, broom, belt
Athletic performance measuring unit clipped to waste or another portion of the body or clothing of the athlete; alternatively or in addition, shoes: pressure sensors for push off when throwing, provides balance and power information wired connection under clothing to computing unit at waist, using magnetic coupling for safety
Glove: accelerometer and tilt sensor for hand position information during throwing—wired connection under clothing to computing unit at waist
Broom: pressure sensor and accelerometer information concerning sweep speed and power—wired connection to glove using magnetic coupling
Computing unit: attached to or integrated into clothing, including a belt about the athlete's waist
Communication Module: Bluetooth 4.0, Wi-Fi, and/or OTA or data logger and/or LED, LCD, OLED display or wireless attached to computing unit
Power Module: Lithium Battery electrically coupled to the athletic performance measuring module.

Figure 10:
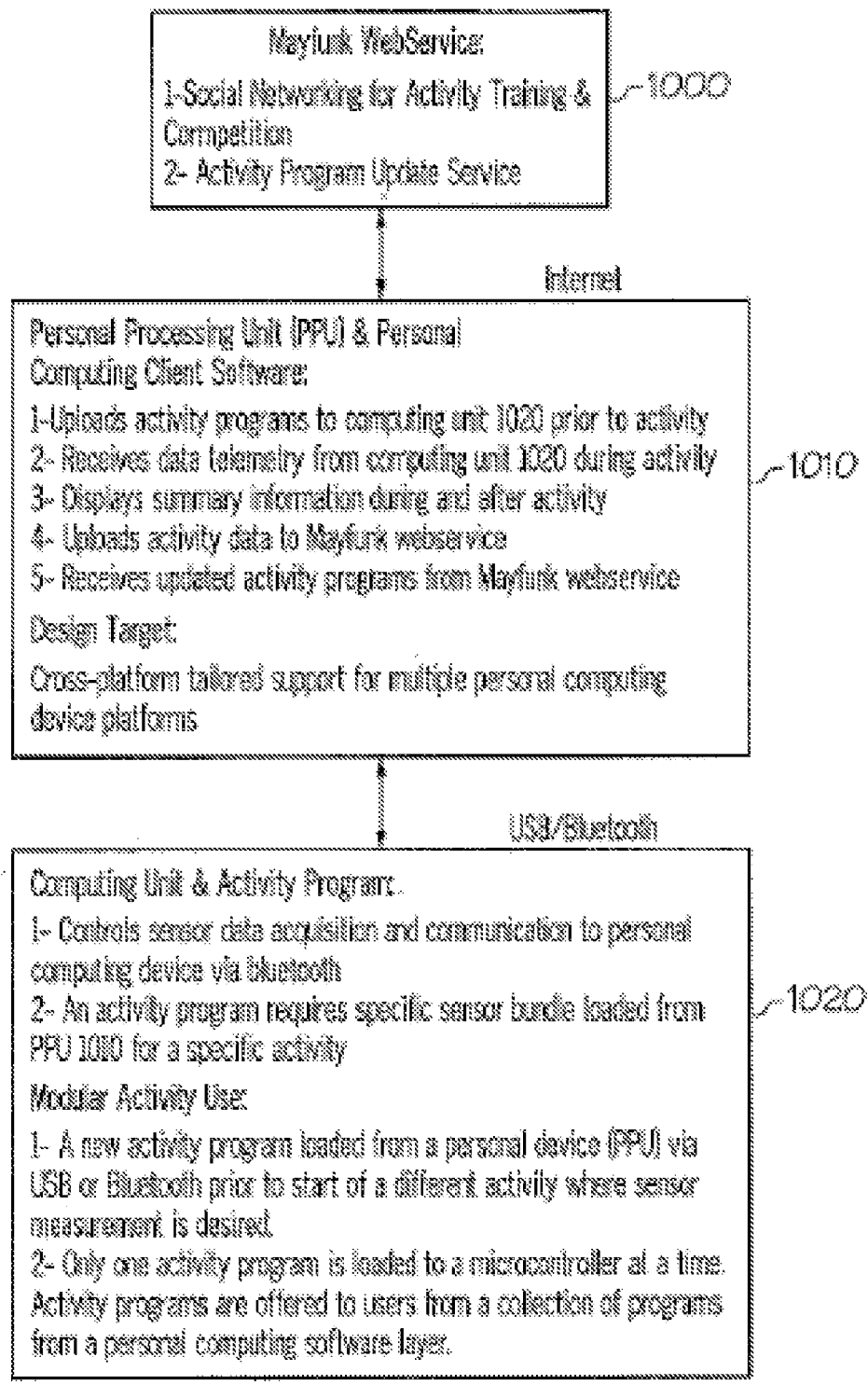
FIG. 10 is a block diagram presenting a system for measuring, transmitting, and displaying jump heights from the athletic performance measuring unit to a web server and/or directly or indirectly to one or more remote personal computing devices in accordance with one exemplary embodiment of the disclosure.
Figure 11A:
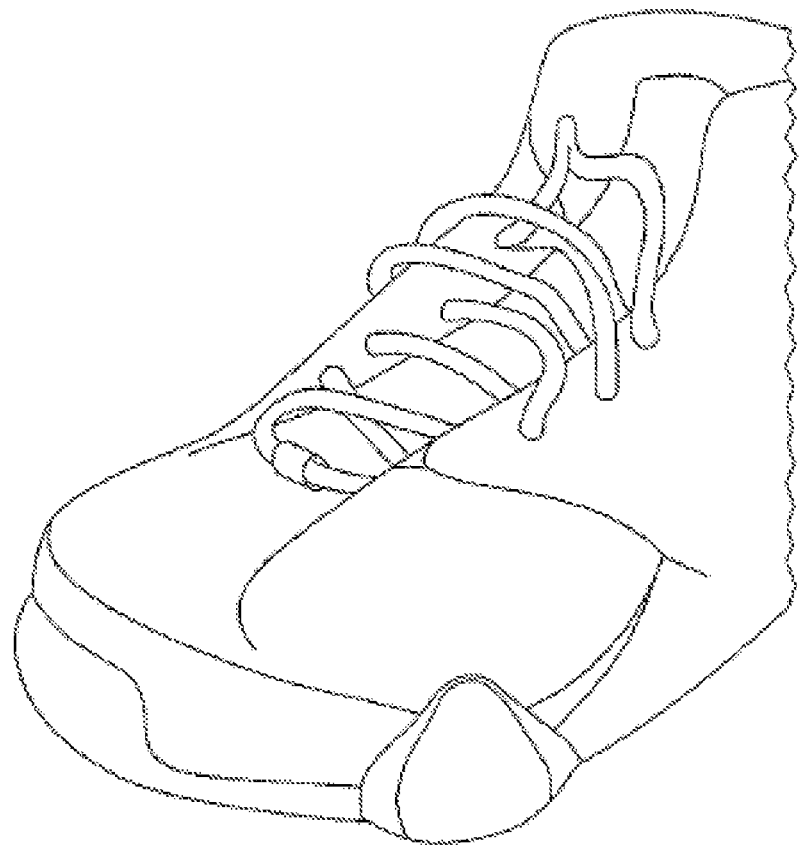
FIGS. 11A-12E are a series of illustrations presenting one manner of mounting a sensor for the athletic performance measuring unit on a shoe in accordance with one exemplary embodiment of the disclosure.
Figure 11B:
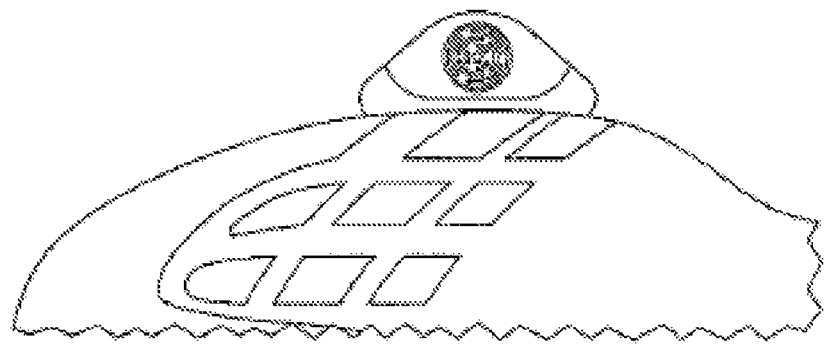
Figure 12A:
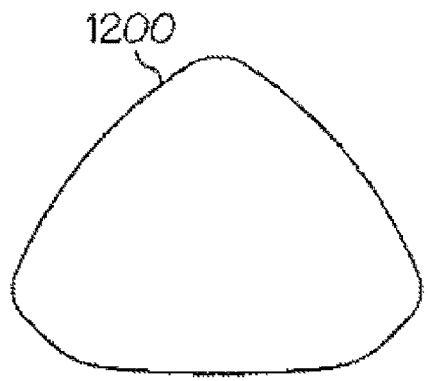
Figure 12B:
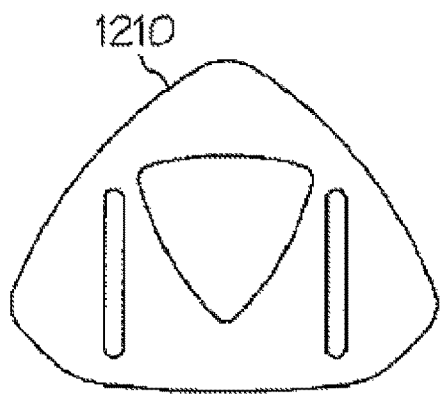
Figure 12C:
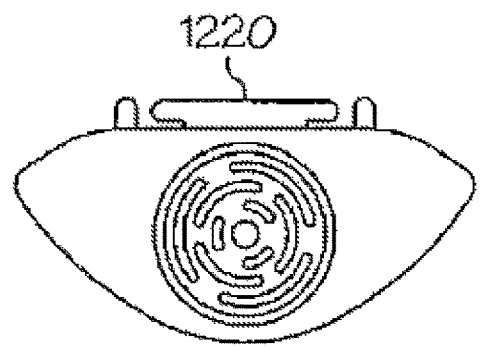
Figure 12D:
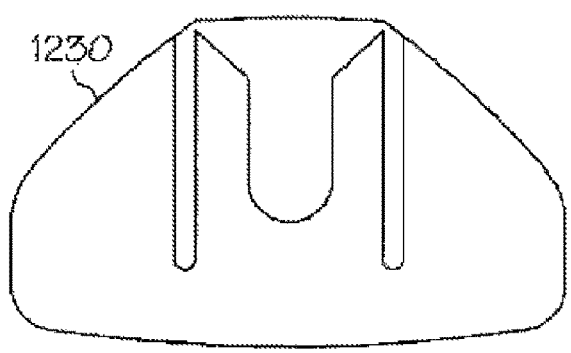
Figure 12E:
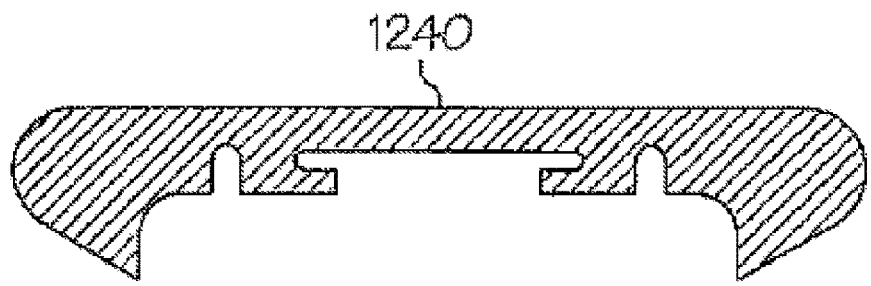

FIG. 10 is a block diagram presenting a system for measuring, transmitting, and displaying calculated jump heights and/or raw sensor data from the athletic performance measuring unit to a web server and/or directly or indirectly to one or more PPUs (including the athlete's PPU) in accordance with one exemplary embodiment. In one example embodiment, the system includes an Internet-based Mayfunk.com web service 1000. The Mayfunk.com web service 1000 can include a social networking web server for activity training & competition software architecture that provides interactive subscriber communication including the loading, storage, and retrieval of athletic statistics to and from the hardware and software supporting the web service 1000. In certain example embodiments, subscribers are able to share their athletic performance parameters as well as view and share the athletic performance parameters of friends, teammates, and/or famous athletes with friends on a real-time or near real-time basis. The web service 1000 makes it possible to share athletic performance parameter data by, for example, uploading and downloading the data during live athletic competition, such as professional or semi-professional sports as well as local adolescent, children, and/or adult leagues. Further, the web service 1000 includes a webpage that is configured to assist a user with the manual uploading, downloading, and storage of athletic performance parameter data that is transmitted from the athletic performance measuring unit, such as the unit 1400 of FIG. 14.

In other words, an athlete can use his or her PPU to monitor/compare his or her athletic performance parameters sensed/calculated by one or more athletic performance measuring units 1400 or those of his friends and manually input this data through the use of a webpage programmed for entry of this data. For example, an individual may enter the athletic performance parameter data manually by typing it into the webpage or optionally transfer the athletic performance parameter data by plugging the athletic performance measuring unit, such as unit 1400, into a computer port (e.g., USB wired, micro USB) or wirelessly (e.g., via Bluetooth, Wi-Fi, OTA, or any other wireless protocol) and loading the file into the web service 1000 via the Internet. The reverse procedure is also programmed into the Mayfunk.com web service software and client computing software. In other words, the webpage may be used to manually retrieve athletic performance parameter data from an online storage database of athletic performance parameter data for one or all athletes having profiles on the webservice 1000, as well as the loading of an athletic performance measuring unit, such as unit 1400, through a wired or wireless connection to an Internet-capable computer or smart device.

Alternatively, the web service 1000 may be programmed for automatic storage of athletic performance parameter data that bypasses the webpage itself. For example, during individual or team play, various athletic performance parameters from one or more athletes equipped with the athletic performance measuring unit, such as unit 1400, are sent automatically via the antenna 130 to the Internet for automatic storage in one or more databases and/or display on one or more pages of the web service 1000. In another example embodiment, during individual or team play, various athletic performance parameters from one or more athletes equipped with the athletic performance measuring unit, such as unit 1400, are sent automatically via the antenna 130 to a PPU via Bluetooth, Wi-Fi, OTA, or another wireless protocol and can then subsequently be transmitted from the PPU to the web service 1000 via the Internet for automatic storage in one or more databases and/or display on one or more pages of the web service 1000. In this manner, the exemplary system provides for real-time automated storage of athletic stats as well as manual storage and retrieval of the data entered into the webpage.

In addition, the system of FIG. 10 can provide for automated retrieval of athletic performance parameters. For example, subscribers (which are not intended to be limited to a formal subscription process or a requirement of payment to access the site) can automatically receive at their PPU real-time, near real-time or delayed transmission of athletic performance parameters for themselves or others of their choosing according to their user-selected or preprogrammed user preferences for selected athletic events, selected sports, or for a set of events suggested by the web service 1000. For example, the web service 1000 can poll first time users or at other predetermined times for the type of athletic events for which a user might want athletic performance parameter data and the type of athletic performance parameter data that the user may desire. If a user selects professional tennis and or a sub category of tennis competitions then this category can be streamed to the user's PPU at the time of the competition or the next time the PPU is activated. Those of ordinary skill in the art will recognize that all of the automated and or manual decisions discussed with reference to the system of FIG. 10 can alternatively be decided on an event-by-event basis leaving the question open until the user makes a decision.

In one example embodiment, the aforementioned functionalities are made possible through the use of personal computing client software loaded onto a subscriber's personal processing unit 1010 (PPU). This computing software can be updated via an activity program update service associated with the example web service 1000. In one example, the updates are optionally initiated automatically via a preprogrammed or pre-selected time frame or updated by a user activation request. User activation of the program update service may be governed via the default personal computing client software loaded into the PPU 1010 that presents a user of the PPU a series of choices to a) start the software update; b) select time period updates or c) accept a default update time.

As has been discussed previously, the PPU 1010 can be an electronic device (e.g., a laptop computer, a personal computer, a smart device, another mobile device, such as a digital assistant, PDA, mp3 player or other audio players, cell phone, pager, beeper, radio, portable television, portable DVD player, other video playing device, calculator, watch, etc. This PPU 1010 interacts with the Internet for the manual as well as automatic reception and transmission of athletic performance parameter data from the web service 1000 and for communication with the computing unit 1020 that controls a sensor 120 or array of sensors 120 for an athletic performance measuring unit, such as the unit 1400 of FIG. 14. In order to communicate with these sensors 120 and to operate them effectively, a set of software controls are typically configured for each sensor type. The PPU 1010 can be preloaded with a personal computing client software to upload activity programs to the computing unit 1020 prior to its activation. Once any activity program uploads are complete, data telemetry may be received from the computing unit 1020 controlling the activated one or more sensors 120. Additionally, each of the PPUs 1010 can be equipped with software that permits the display on a graphical user interface (GUI) associated with the PPU 1010 of summary information during and after the athletic activity. The PPU 1010 can then upload athletic performance parameter data via the Internet to the web service 1000 either automatically or through manual activation by user control. For example, when a user originally activates his or her subscription or creates a page on the website via the web service 1000, the user can be presented with the option of accepting predefined default periodic data transfers, making the transfers manually or leaving the question open for each event.

In addition, in certain example embodiments, there may be times where the software loaded into the computing unit 1020 of the athletic performance measuring unit, such as unit 1400 of FIG. 14, can be updated. These updates may arrive for a variety of reasons. For example, one potential reason for a software update could be due to changes in existing sensor software that may be beneficial in improving the sensing of the athletic performance parameters. Alternatively, the updates may be caused by the changing of modules in a sensor package that may or may not include new software in the computing unit 1020 for the athletic performance measuring unit 1400. Further, when a user desires to have a different type of sensor 120 or new sensor module to monitor his or her athletic performance parameters or those of another individual, an update to the activity program may be necessary for data acquisition to function more effectively. In this event, the webservice 1000 can provide automated or manual updated activity programs that are transmitted to the PPU 1010 of a user. The user is then able to receive updated software for the athletic performance measuring unit 1400, thereby improving the accuracy and efficiency of the acquisition of athletic performance parameters associated with the particular sensors 120.

In one example, the web service 1000 is able to determine the necessary updated activity program(s) by periodically polling the PPUs 1010 and/or the athletic performance measuring units 1400 communicably connected to the web service 1000 so as to discern the type of sensor activity programs necessary for each unit 1400. Alternatively, the updated activity program(s) can be requested by the user at the web service 1000 via a request from the personal computing client software loaded on the PPU 1010, which can determine the need for updated software based upon a transmitted update request across the Internet containing the current software version loaded in the computing unit 1020 of the athletic performance measuring unit.

In one exemplary embodiment, the activity program controls sensor data acquisition and communication to the PPU 1010 via wired or wireless communication (such as USB or Bluetooth, Wi-Fi, OTA, etc.). In certain embodiments, the activity program may be configured to work with a specific sensor bundle for a specific activity. In such an example, whenever a new activity requires a different type of sensor unit, a new activity program (e.g., mobile application or app) may need to be loaded into the computing unit 1020 of the athletic performance measuring unit, such as unit 1400 of FIG. 14. The new program may be downloaded from the athlete's PPU.

Finally, it should be understood that the software that has been described above and throughout this document are cross-platform tailored with support for multiple personal computing device platforms.

FIGS. 11A-12E are a series of illustrations presenting one manner of mounting or integrating a sensor for the athletic performance measuring unit on a shoe in accordance with one exemplary embodiment of the disclosure. Referring now to FIGS. 11A-12E, the example mounting system can include a sensor unit and bracket as shown in elements 1200-1240 of FIGS. 12A-E. An example sensor is shown in items 1200-1220 and an example mounting bracket for the sensor is shown in items 1230-1240. FIG. 12A presents a front view 1200 of the example sensor and FIG. 12B presents a back view 1210 of the sensor along with associated logo. The back view 1210 shows one or more protrusions (lines and dark triangle area) that can be integral with or coupled to the sensor unit. In one example, these protrusions can extend off the ordinary surface of the light triangular area of the sensor unit. These protrusions are configured to be inserted into the bracket as a male connector is inserted into the female connector bracket shown in 1230-1240 of FIGS. 12D-E. Another back view 1220 of the sensor is provided in FIG. 12C, wherein the view 1220 shows a mounting bracket male connector in the top of FIG. 12C that is to be inserted in the slot of the female bracket of 1230-1240 of FIGS. 12D-E. Element 1230 of FIG. 12D presents the bracket front view mounting clip-in slot that serves as the receiver for the sensor unit protrusions described with respect to items 1200-1220 of FIGS. 12A-C. Element 1240 presents the bracket top view 1240 and more clearly illustrates the mounting clip-in slot for receiving the male connector piece. As shown in this example, the bracket can be attached to a shoe with an adhesive and the sensor unit can be attached to the bracket with a simple male-female snap in connector configuration. However, other attachment configurations are possible, such as the physical integration of the sensor unit into the shoe as one piece with the shoe without mounting it on a bracket. Also, while a shoe has been shown as the piece of clothing that has the sensor and/or the athletic performance measuring unit as a whole, it is contemplated that the unit, such as unit 1400 of FIG. 14 may be coupled or integrated into another portion of the body or clothing of the user (e.g., with the example clip of FIGS. 15A-C), may be coupled to or integrated into another device used by the user (e.g., a bicycle, skateboard, golf club, snowboard, skis, motorcycle, motorcross, all-terrain vehicle, jet ski, snowmobile, surfboard, scooter, wake board, windsurfing board, kite surfing board, pogo stick, rally sport car, in-line skates, or the like), or may be integral with or removably coupled to clothing, including footwear or other body wear (e.g., shirts, shorts, underwear, sports bra, pants, jacket, hat or other headwear, straps, belts, socks, gloves, medical tape, and/or kinesio tape). Additionally, the entire system may be made integral with the article(s) of clothing or the articles of clothing may be provided with pockets to removably insert and remove the athletic performance measuring unit, such as unit 1400 of FIG. 14 from the article of clothing such that it is not easily identifiable to an external user and provides no performance penalties for the use of the device. In certain example embodiments where the athletic performance measuring unit is integrated into clothing, the clothing may be washed without fear of damaging the athletic performance measuring unit. In any case, whether overtly displayed or covertly worn the athletic performance measuring units are designed to be fully detachable, partially detachable, or non-detachable, thus, running the full range of potential options. Additional modifications to the mounting bracket system may also include the connection system of FIGS. 13A-B.

Figure 13A:
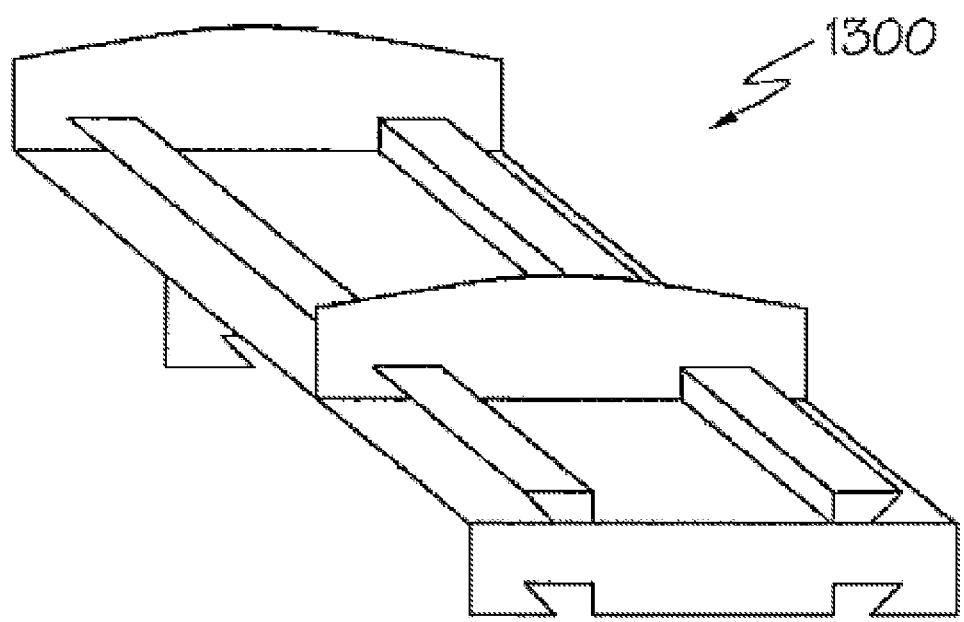
FIGS. 13A-B present two illustrations of an example a tongue and groove locking system for electro-mechanical connections along with stackable add-ons for the athletic performance measuring unit in accordance with one exemplary embodiment of the disclosure.
Figure 13B:
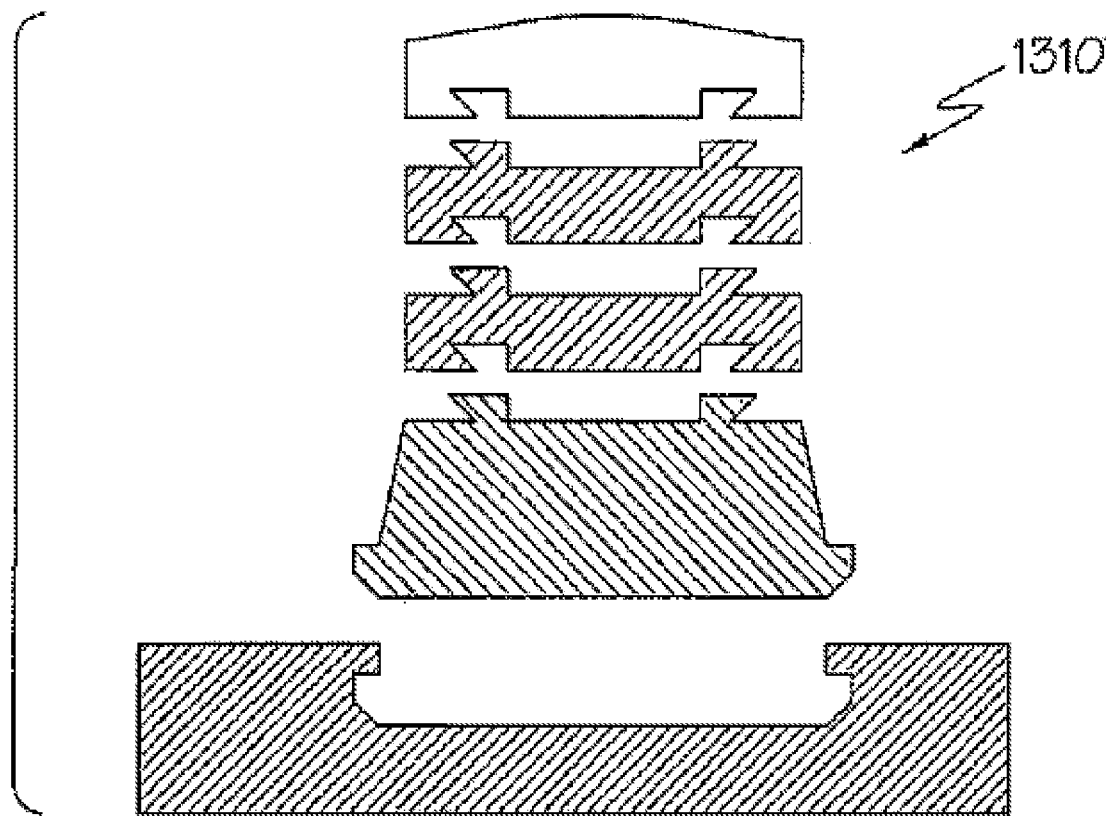

FIGS. 13A-B present two illustrations of an example tongue-and-groove locking system 1300-1310 for mechanical or electro-mechanical connections in accordance with an exemplary embodiment. Referring to FIGS. 1, 13A-B, and 14, the exemplary system 1300-1310 shows a tongue and groove connection where the tongue and groove rails contain the electrical connections for the hardware. Element 1310 illustrates that the tongue and groove connections can provide stackable add-ons with an electrical connection to the mounting bracket. In this example, the athletic sensors 120 are embedded/integrated or removably coupled or inserted in the piece of clothing (not shown) and a computing unit 110 attaches to the bracket whilst stackable add-ons provide further capabilities and updates to the existing hardware all capped off with a battery for easy replacement. While the exemplary sensors 120 of FIGS. 13A-B have been described as being embedded/integrated in the piece of athletic clothing, they may also be contained in one of the stackable add-ons, or otherwise communicably coupled to the athletic performance measuring unit.

Figure 14A:
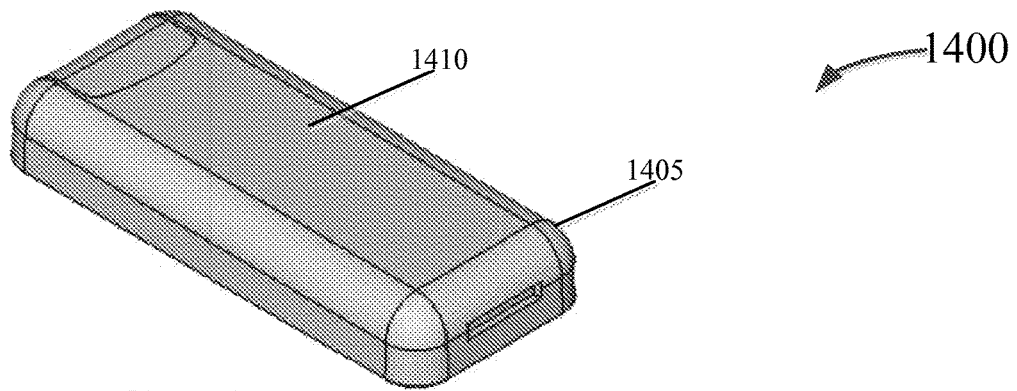
FIGS. 14A-H present multiple views of an alternative athletic performance measuring unit in accordance with one exemplary embodiment of the disclosure.
Figure 14B:
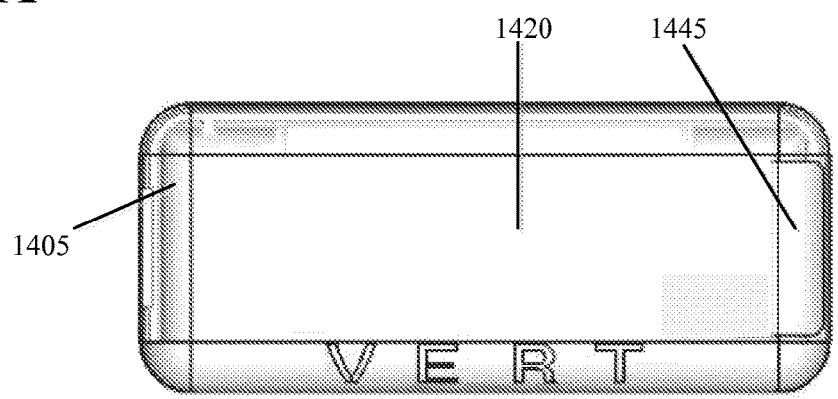
Figure 14C:
Figure 14D:
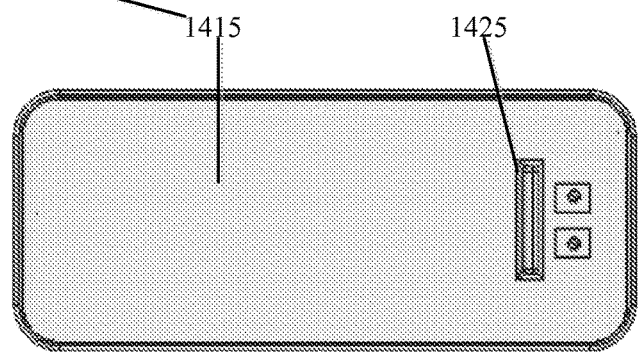
Figure 14E:
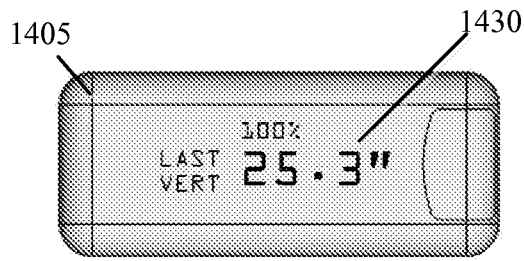
Figure 14F:
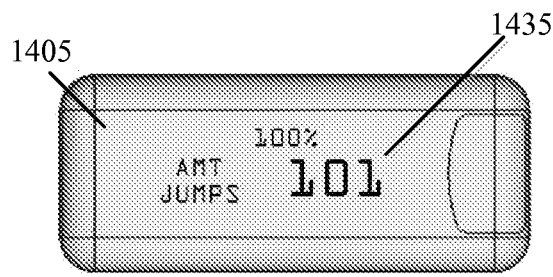
Figure 14G:
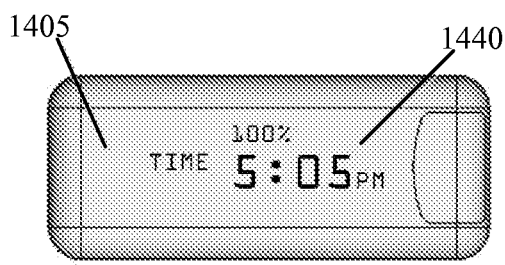
Figure 14H:
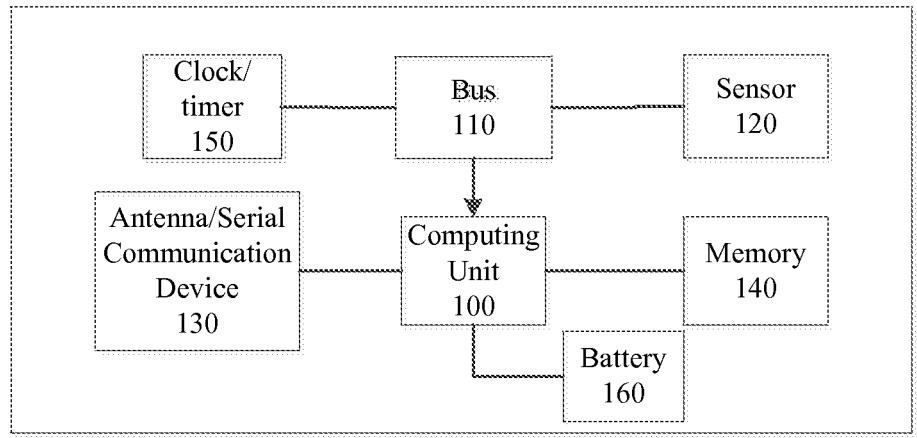

FIGS. 14A-14H present multiple views of an alternative athletic performance measuring unit 1400 in accordance with one exemplary embodiment of the disclosure. Now referring to FIGS. 1 and 14A-H. The example athletic performance measuring unit 1400 can include a housing 1405 having a front wall, a back wall, top and bottom walls and one or more side walls. The walls of the housing 1405 can define an interior cavity. In one example embodiment, the housing 1405 can include a front housing panel 1410 and a rear housing panel 1415 that is coupled to the front housing panel 1410 to define the interior cavity of the housing 1405. For example, the front housing panel 1410 and the rear housing panel 1415 can be snap-fitted together, screwed together using screws or other coupling devices, adhered together using glue or another type of adhesive, ultrasonically sealed or otherwise coupled together in another manner known to those of ordinary skill in the art to create the housing 1405. Alternatively, the housing 1405 can be formed as a single-piece housing or can be made up of more than two panels. The front 1410 and rear 1415 housing panels can be made of plastic, metal, glass, or any other material known to those of ordinary skill in the art. In another alternative embodiment, the unit 1400 may include the components discussed below without a housing. For example, the components may be independently coupled or integrated into another device, such as a bicycle, motorcycle, motorcross bike, all-terrain vehicle, three-wheeler, four-wheeler, skateboard, pogo stick, snowboard, scooter, windsurfing board, kite surfing board, skis, surfboard, snowmobile, automobile (e.g., rally sport cars), or other similar device; the animal collar, harness, or saddle; or a ball, toy, or any other product to which the unit is coupled or integrated In certain example embodiments, as shown in FIG. 14H, the housing 1405 can include the computing unit 100 (such as a controller, microcontroller, ARM microcontroller or other type of processor), the electrical interface 110 (which can include, for example, a serial, parallel, Bluetooth, USB, I2c, generic bus or other type of electrical interface), one or more sensors 120, volatile and/or non-volatile memory 140, optionally a clock and/or timer 150 and a battery 160 electrically coupled to at least one of the computing unit 100, the electrical interface 110, the sensors 120, the memory 140, and the clock/timer 150. Example discussion of at least a portion of these components is provided above with reference to FIG. 1, the contents of which are incorporated herein by reference.

In one example embodiment, the one or more sensors 120 can be generally operated or tailored for a specific athletic endeavor or the measurement of a particular athletic performance parameter. The exemplary sensors 120 can be made up of a combination of digital or analog devices. In certain example embodiments, the sensors 120 include, but are not limited to, a gyroscope and an accelerometer communicably coupled to the computing unit 100. In certain alternative embodiments, the sensors 120 are capable of transmitting sensor data via Blue tooth, Wi-Fi, OTA via another wireless protocol directly to a PPU (e.g., the athlete's smart device), the web server, or a non-personal computing device without the need for the housing 1405, the computing unit 100, or the antenna 130.

In certain embodiments, the gyroscope is a three-axis gyroscope and the accelerometer is a three-axis accelerometer. Alternatively, the sensors 120 can be any other type of sensor, including but not limited to, a magnetometer, radio transmitting and/or receiving circuitry, a vibration motor, an ultrasonic sensor, an infrared sensor, a buzzer, a speaker, a microphone, a GPS device, a pressure sensor, an optical or other light sensor, and a piezo element. In addition, the sensors 120 can include electronics that act as sensor inputs or they can also include indicators and switches to be used to control the computing unit 100 operation or to provide real-time or near real-time feedback. In the case of a golf-training scenario, the sensors 120 optionally include indicator lights for feedback on club face position or stance balance.

Furthermore, the athletic performance measuring unit 1400 can be uploaded with customized software programs depending on the athletic activity or the athletic performance parameter to be monitored and displayed. The athletic performance measuring unit 1400 is meant to be a common reusable element across multiple athletic activities that make use of similar sensor technologies. When it is desired to review new or different athletic performance parameters or if new technologies are developed, the athletic performance measuring unit 1400 can be upgraded, either through wired or wireless communication to provide the unit 1400 with new capabilities, yet still remain backwards compatible with previously purchases athletic sensor sets.

In one example embodiment, new software may be optionally uploaded to the unit 1400 via a wired or wireless connection to a PPU, such as a personal computer, laptop computer or smart device, before the athlete begins a new athletic activity. While the athletic performance measuring unit 1400 will typically come pre-configured to measure and display one or more athletic performance parameters as part of a purchase of the unit 1400, the sensors 120 and/or software of the unit 1400 can be modified to measure and display different parameters than originally available in its initial configuration so that the unit 1400 may be used in other athletic activities and may provide the athlete with other athletic performance parameters. As such, the same athletic performance measuring unit 1400 can be re-used with different sensors 120 by, for example, uploading the corresponding software programs for the desired sensors 120 from a PPU via, for example, a mobile application loaded on the smart device or via the web server. The example sensor configurations can be extended further using radio telemetry technology for sensor situations where a physical connection between the computing unit 100 and sensor 120 is impractical or impossible. Such example sensors 120 may need to provide their own power source.

In certain example embodiments, the battery 160 is a rechargeable lithium-ion battery. In addition or in the alternative, the athletic performance measuring unit 1400 may also be powered from an external power source. For example, the housing 1405 of the athletic performance measuring unit 1400 can include one or more device connections (e.g., a USB connector) for electrically coupling the unit 1400 to an external source of power including, but not limited to, a laptop computer, a personal computer, a smart device, a conventional wall outlet, and a battery pack. In one example embodiment, the same battery 160 energizes the computing unit 100, sensors 120, and communications module 130. Each of the computing unit 100, electrical interface 110, sensors 120, memory 140, optional clock/timer 150, and battery 160 can be disposed within the interior cavity of the housing 1405 in one example embodiment. Alternatively, one or more components, such as one or more sensors 120 may be disposed outside of the housing 1405 yet still be capable of providing sensor data to the computing unit 100 either via a direct coupling (e.g., wired) or via wireless communication. In another alternative embodiment, the battery 160 may be a physically separated module connected to the unit 1400 only by a wire lead. The exact form factor and voltage battery needed, may be determined by the space, weight, and movement constraints of an individual athletic activity. As the system is modular different battery options can be included with different sensors 120, different activity bundles, or optionally provided a la carte. Furthermore, while the example of FIG. 14H presents a single computing unit 100 in the housing 1405, in certain example embodiments, the unit 1400 may include two or more computing units 100 representing two or more microprocessors within the housing 1405. In the example embodiment that includes two microprocessors, one of the microprocessors can receive data from the sensors 120, calculate information based on the received sensor data, as necessary, and present the data for viewing on the display 1420. The second microprocessor can control the wireless communication between the athletic performance measuring unit 1400 and other PPUs and/or non-personal computing devices by way of, for example, Wi-Fi, OTA, and/or Bluetooth communication.

Further, the housing 1405 can also include the antenna 130. The antenna 130 can be positioned inside the housing 1405 or alternatively can be positioned through an opening (not shown) of the housing 1405. In yet another alternative embodiment, the antenna 130 (not shown) can be disposed on an exterior surface of the housing 1405. In certain exemplary embodiments, the antenna 130 is a transmitter/receiver (or transceiver) capable of both transmitting data from the unit 1400 and receiving data for the unit 1400. For example, the antenna 130 is configured to receive, such as via Wi-Fi, Bluetooth and/or OTA the one or more customized software programs that provide computer-executable instructions to the computing unit 100 for operating the components of the unit 1400. In addition, the housing 1405 of the athletic performance measuring unit 1400 can include one or more device connections for communicably coupling the unit 1400 to a PPU for receiving data, such as operational software programs, via the connection The front housing panel 1410 can also include an opening for receiving and providing a viewing path to a display 1420. In one exemplary embodiment, the display 1420 is an organic light emitting diode (OLED) display. Alternatively, the display 1420 can be any form of digital display including, but not limited to, light emitting diode (LED) display, liquid crystal display (LCD), plasma display, or any other form of display technology known to one of ordinary skill in the art. In alternative embodiments, instead of or in addition to the display 1420 and the antenna 130, the athletic performance measuring unit 1400 may also output sensor data and/or athletic performance parameter data to a PPU or data logging device such as a micro-SD card which is later read by a personal computer/laptop computer. In certain example embodiments, the rear housing panel 1415 can also include a battery access recess 1425 that can assist with separating the rear housing panel 1415 from the front housing panel 1410 to access the interior cavity and replace the battery as necessary.

FIGS. 14E-G present multiple views of the athletic performance measuring unit 1400 showing example forms of information that may be displayed on the display 1420. The information presented on the display 1420 in these examples includes jump height 1430, jump count or the number of jumps made and sensed in one or more sessions 1435, and the current time 1440. These presentations on the display are for example purposes only as many other types of information may be presented on the display 1420 including, but not limited to, average jump height, touch height (the height an athlete extending one or both arms in the air would reach with the person's fingers based at least in part on the sensed and/or calculated jump height), jump length, jump hang time, swing speed, number of swings, and swing speed average.

FIGS. 15A-C present multiple views of a clip device 1500 for holding the athletic performance measuring unit 1400 and for securing the athletic performance measuring unit 1400 to an article of clothing or other device (e.g., a bicycle, motorcycle, motorcross bike, all-terrain vehicle, three-wheeler, four-wheeler, skateboard, pogo stick, snowboard, scooter, windsurfing board, kite surfing board, skis, surfboard, snowmobile, automobile (e.g., rally sport cars), or other similar device; the animal collar, harness, or saddle; or the ball, toy, or any other product to which the unit is coupled or integrated) and used by the athlete or animal (for the collar, harness, or saddle) in accordance with one exemplary embodiment of the disclosure. Referring to FIGS. 14A-15C, the exemplary clip device 1500 includes a front panel 1505 and a rear panel 1510. In one example embodiment, each of the front panel 1505 and the rear panel 1510 are substantially planar. However, in alternative embodiments, one or both of the front panel 1505 and the rear panel 1510 could be curved along one or more axes to allow for the clip device to be secured to another curved or generally cylindrically-shaped surface, such as a frame, handlebars, or bike stem of a bicycle.

Each of the front panel 1505 and the back panel 1510 have a front surface and a rear surface such that the rear surface of the front panel 1505 is disposed adjacent the front surface of the back panel 1510. The front panel 1505 includes a clip securing portion 1515 generally disposed along the bottom portion of the panel 1505 and an athletic performance measuring unit receiving portion 1520 generally disposed along a top portion of the panel. However, the position of each is for example purposes only. The front panel 1505 can also include one or more catch tabs 1525 that extend orthogonally or substantially orthogonally out from the front surface of the front panel 1505. In one exemplary embodiment, the clip device 1500 includes four catch tabs 1525 corresponding to the four corners of the unit 1400. Each catch tab 1525 can have a wall with an arcuate shape and can be configured to slightly deform or flex generally-radially outward as the vertical measurement unit 1400 is pressed into the clip device 1500 along the receiving portion and to provide a holding force to hold the unit 1400 in place once the back panel housing 1415 abuts the front surface of the front panel 1505 along the receiving portion of the front panel 1505.

The clip device 1500 can also include one or more spring mounting tabs 1530 extending orthogonally or substantially orthogonally out from the rear surface of the front panel 1505 and one or more spring mounting tabs 1535 extending orthogonally or substantially orthogonally out from the front surface of the back panel 1510. The spring mounting tabs 1530 and 1535 work cooperatively to hold a spring 1540, such as a torsion spring. For example, the torsion spring 1540 can bias the front surface of the back panel 1510 towards the rear surface of the front panel 1505 along the clip securing portion 1515 of the front panel 1505. A user can squeeze the top edges of the front panel 1505 and back panel 1510 above the spring mounting tabs 1530 and 1535 together to open a space between the front panel 1505 and back panel 1510 below the spring mounting tabs 1530 and 1535 and place an article of clothing, belt, strap, or other device (e.g., board portion of a skateboard, scooter, surfboard, windsurfing board, kite surfing board, or a tubular section of handle bars or frame of a bicycle, etc.) between the front panel 1505 and back panel 1510 and release the top edges. The spring force of the spring 1540 will cause the space between the front panel 1505 and back panel 1510 below the spring mounting tabs 1530 and 1535 to move towards one another and grasp the material/element between the panels 1505, 1510.

Figure 16A:
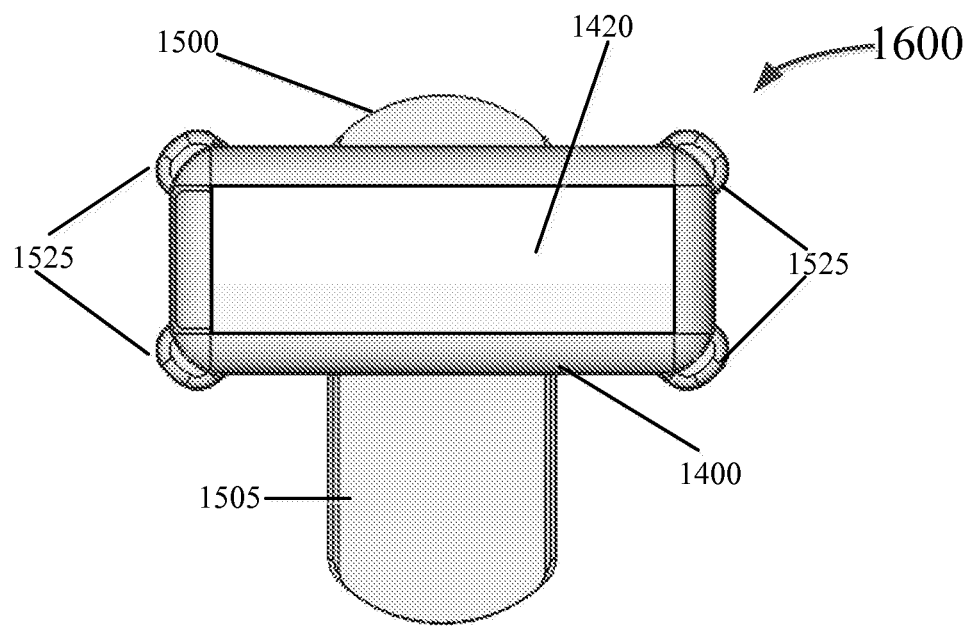
FIGS. 16A and 16B are front and rear views of the athletic performance measuring unit of FIGS. 14A-H secured by the clip device of FIGS. 15A-C in accordance with on exemplary embodiment of the disclosure.
Figure 16B:
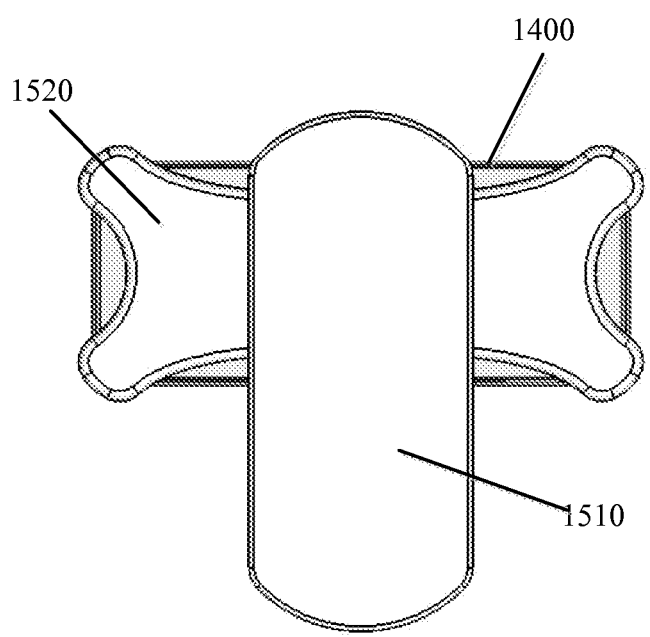

FIGS. 16A and 16B are front and rear views of the athletic performance measuring unit 1400 secured in the clip device 1500 in accordance with one exemplary embodiment of the disclosure. As can be seen in FIG. 16A, the catch tabs 1525 hold the four corner edges of the athletic performance measuring unit 1400 to keep it attached to the clip device 1500.

In certain example embodiments, the athletic performance measuring unit 1400 can be coupled to or integrated into athletic shoes or other footwear similar to that shown in FIG. 6. Referring to FIGS. 6 and 14, the example shoes of FIG. 6 present an example embodiment in which athletic performance measuring units are integrally formed in the shoe. However, alternatively the athletic performance measuring unit 1400 can alternatively be velcroed to the shoe, clipped to the shoe, such as by using the example clip 1500 or otherwise removably or fixedly attached to the shoe or any other article of clothing. The athletic performance measuring unit 1400 can sense, measure, record, and/or display the height of a particular jump. In certain example embodiments, the sensors 120 can include one or more gyroscopes and one or more accelerometers. In an alternate embodiment, the sensors 120 can be ultrasonic or laser transmitters and unit 1400 can further include processing electronic circuitry which transmits, receives and processes the signals with digital or digital/analog conversion technology. Other technologies, such as radio, optical, and electromagnetic transmissions of different frequencies including microwaves may also be alternatively utilized.

The sensors and ultrasonic transducers can either be incorporated into the unit and/or placed about various locations on the shoe soles, (i.e., toe, heel or central area, or about the perimeter of the shoe) or any other type of clothing. In certain example embodiments, the digital display location can vary on the footwear/clothing as well. It is contemplated that miniaturized technology having durability, impact and shock-resistant features to protect the sensor, and electronic packages and or devices within the base or perimeter of the footwear and/or within the housing 1405 will optimize performance.

In addition, in certain example embodiments, once the unit 1400 detects and displays the jump height, that same data can be relayed in real-time or near real-time to PPUs, the web server, repeaters, non-personal computing devices (e.g., arena displays, jumbotrons, and televisions for home (remote) or local viewers (in a manner similar to how the first-down line is overlaid on a televised display of a football field)) as discussed in greater detail below. Similarly, the sensor data sensed by the sensors of the unit 1400 can be transmitted either directly or indirectly to a PPU which can calculate, for example, jump height, touch height, average jump, peak jump, hang time, jump length, and/or number of jumps based on the sensed sensor data. The PPU can then transmit the calculated athletic performance parameters to other PPUs (e.g., a laptop computer, a personal computer, a smart device, another mobile device, such as a digital assistant, PDA, mp3 player or other audio players, cell phone, pager, beeper, radio, portable television, portable DVD player, other video playing device, calculator, watch, etc.), non-personal computing devices (e.g., networked computer, web server, broadcast TV, display devices at arenas, stadiums, fields, or other locations where the athlete is participating and/or the athletic performance measuring unit is located, or one or more social or other forms of website) and/or back to the unit 1400, as will also be discussed in greater detail below.

As such, with the unit 1400, the fan, reporter, coach or corporate officer can watch the athletic contests and/or their favorite player, listen and view the player's statistics in real-time or near real-time, and monitor one or more athletic performance parameters of that athlete, such as the maximum heights of jumps for dunks, hang time, spectacular plays or tip-offs. In addition, the display 1420 can be modified to provide enhanced graphics that would illustrate the vertical leap by arrows, vectors and vivid color schemes.

As one example, an individual athlete during basketball practice will have the ability to capture his/her individual jump-shot performance and measure his/her ideal vertical leap height and rate. This can be accomplished, for example, by the athlete taking a series of twenty similar jump-shots and analyzing jump height vs. shot success; thereby allowing the player to apply these statistics in an individual or team practice. In addition, the sensor data sensed by the unit 1400 and/or the athletic performance parameter data generated by the unit 1400 can help a player to determine where he/she ranks amongst his/her peer group known as a "bar" by, for example, displaying and comparing personal athletic performance parameter data to athletic performance parameter data of other athletes via the web server on a social website, as discussed below.

Figure 17:
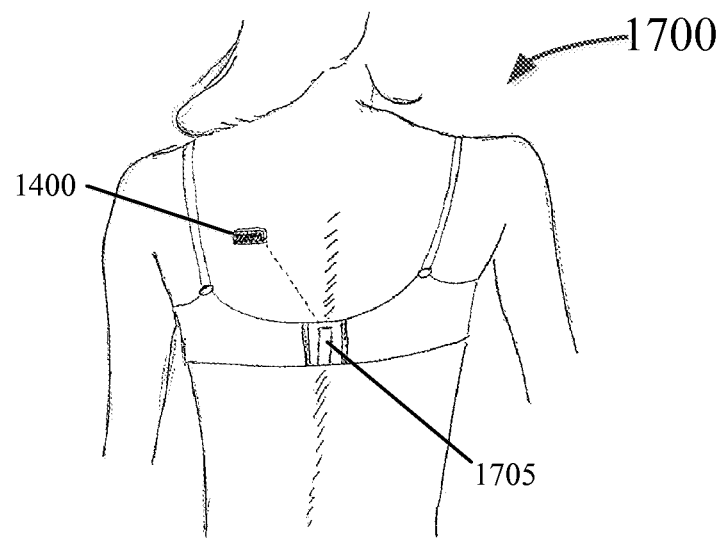
FIG. 17 is a graphical illustration of a sports bra including a pocket for receiving the athletic performance measuring unit of FIGS. 14A-H in accordance with one exemplary embodiment of the disclosure.

FIG. 17 is a graphical illustration of a sports bra 1700 including an integral or added pocket for receiving and/or integrating the example athletic performance measuring unit 1400 in accordance with one exemplary embodiment of the disclosure. Now referring to FIGS. 14A-H and 17, the exemplary sports bra 1700 includes a pocket 1705. In one example embodiment, the pocket 1705 is enclosed on the bottom, left, and right sides and is open along the top side. The athletic performance measuring unit 1400 can be inserted into the pocket 1705 and removed from the pocket 1705 through the opening. The ability to insert and remove the athletic performance measuring unit 1400 from clothing material as desired allows a user to move the unit 1400 to the particular clothing they are wearing that day and reduces the need for a single user to have multiple units (each integrated with a particular piece of clothing). Alternatively, the unit 1400 is integrated into the sport bra 1700 or any other type of clothing, such that the bra 1700 or any other type of clothing can be washed with the unit 1400 still integrated and the unit 1400, which may or may not include an outer housing 1405, will remain operational. While the example pocket 1705 is presented along the back side of the sports bra 1700 this is for example purposes only, as the pocket 1705 could alternatively be positioned along any other portion of the sports bra 1700 or any other type of clothing. Further, while the example of FIG. 17 is described with reference to a sports bra 1700, this too is for example purposes only, as an integral pocket may be provided in other types of clothing, including bras or any other type of undergarment worn by men or women including, but not limited to, bras, undershirts, panties, boxers, briefs, boxer-briefs, sliding pants, spandex pants, and the like.

Figure 18:
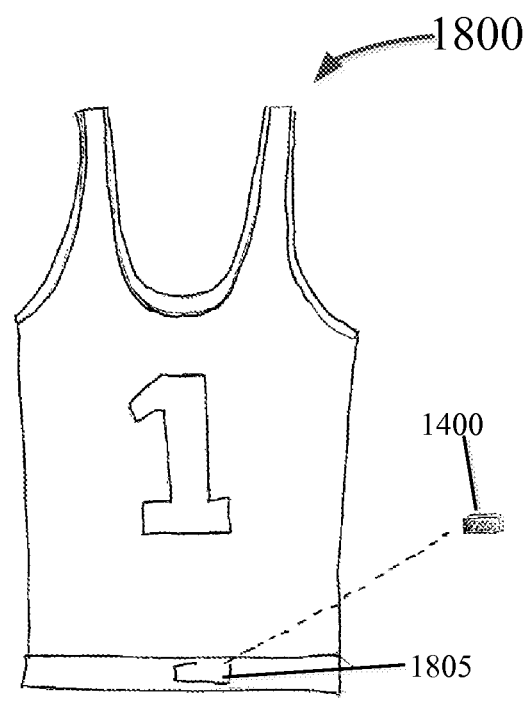
FIG. 18 is a graphical illustration of a sports jersey including an integrated pocket for receiving the athletic performance measuring unit of FIGS. 14A-H in accordance with one exemplary embodiment of the disclosure.

FIG. 18 is a graphical illustration of a sports jersey 1800 including an integral or added pocket for receiving and/or integrating the example athletic performance measuring unit 1400 in accordance with one exemplary embodiment of the disclosure. Now referring to FIGS. 14A-H and 18, the exemplary sports jersey 1800 includes a pocket 1805. In one example embodiment, the pocket 1805 is enclosed on the bottom, left, and right sides and can be partially enclosed and partially open along the top side. The athletic performance measuring unit 1400 can be inserted into the pocket 1805 and removed from the pocket 1805 through the opening. The ability to insert and remove the athletic performance measuring unit 1400 from clothing material as desired allows a user to move the unit 1400 to the particular clothing they are wearing that day and reduces the need for a single user to have multiple units (each integrated with a particular piece of clothing). Alternatively, the unit 1400 is integrated into the sports jersey 1800 or any other type of clothing, such that the sports jersey 1800 or any other type of clothing can be washed with the unit 1400 still integrated therein and the unit 1400, which may or may not include an outer housing 1405, will remain operational. While the example pocket 1805 is presented along the front side of the sports jersey 1800, this is for example purposes only, as the pocket 1805 could alternatively be positioned along any other portion of the sports jersey 1800. Further, while the example of FIG. 18 is described with reference to a sports jersey 1800 (such as a basketball jersey), this too is for example purposes only as an integral or added pocket may be provided in other types of jerseys or any other type of shirt worn by men or women while conducting their activity including, but not limited to, volleyball jerseys, football jerseys, baseball jerseys, t-shirts, sweatshirts, undershirts, jackets, and the like.

Figure 19:
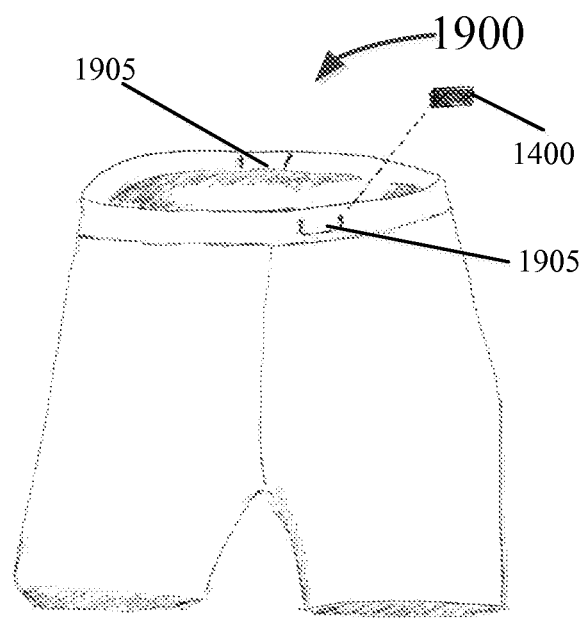
FIG. 19 is a graphical illustration of underwear or shorts including an integrated pocket for receiving the athletic performance measuring unit of FIGS. 14A-H in accordance with one exemplary embodiment of the disclosure.

FIG. 19 is a graphical illustration of a pair of shorts 1900 including an integral or added pocket for receiving and/or integrating the example athletic performance measuring unit 1400 in accordance with one exemplary embodiment of the disclosure. Now referring to FIGS. 14A-H and 19, the exemplary shorts 1900 includes a pocket 1905. In one example embodiment, the pocket 1905 is enclosed on the bottom, left, and right sides and can be partially enclosed and partially open along the top side. The athletic performance measuring unit 1400 can be inserted into the pocket 1905 and removed from the pocket 1905 through the opening. The ability to insert and remove the athletic performance measuring unit 1400 from clothing material as desired allows a user to move the unit 1400 to the particular clothing they are wearing that day and reduces the need for a single user to have multiple units (each integrated with a particular piece of clothing). Alternatively, the unit 1400 is integrated into the shorts 1900 or any other type of clothing, such that the shorts 1900 or any other type of clothing can be washed with the unit 1400 still integrated therein and the unit 1400, which may or may not include an outer housing 1405, will remain operational. While the example pocket 1905 is presented along the front side of the shorts 1900 in the waistband area, this is for example purposes only, as the pocket 1905 could alternatively be positioned along any other portion of the shorts 1900. Further, while the example of FIG. 19 is described with reference to shorts 1900 (such as a basketball shorts), this too is for example purposes only as an integral or added pocket may be provided in other types of shorts or pants worn by men or women while conducting their sporting activity including, but not limited to, volleyball shorts, basketball shorts, football pants, sliding pants, sweatpants, and the like.

Figure 20:
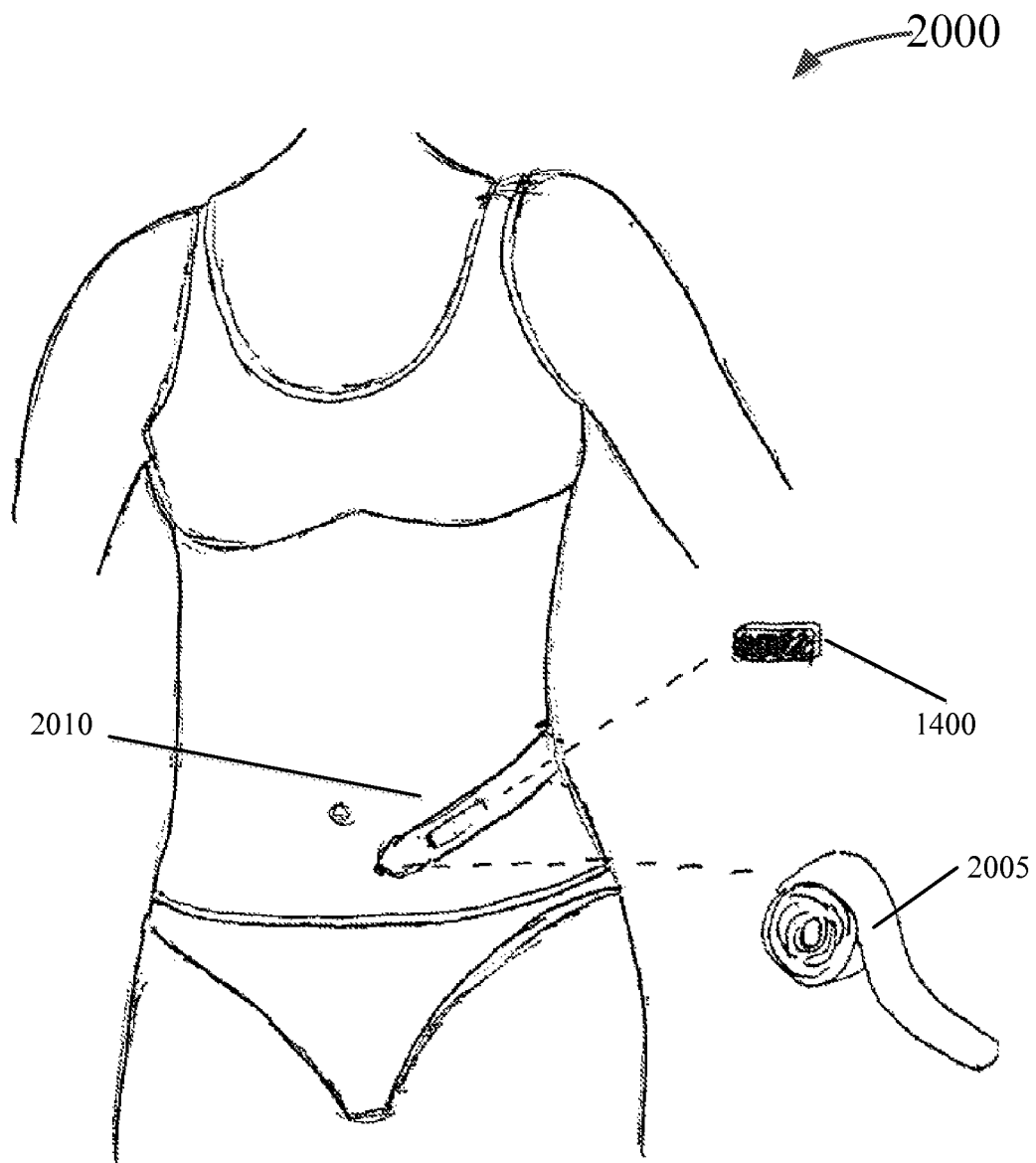
FIG. 20 is a graphical illustration of another method for securing the athletic performance measuring unit to the body of an athlete in accordance with one exemplary embodiment of the disclosure.

FIG. 20 is a graphical illustration of another method 2000 for securing the athletic performance measuring unit 1400 to the body of an athlete in accordance with an exemplary embodiment of the disclosure. Referring now to FIGS. 14A-H and 20, the exemplary method of attachment 2000 includes the athletic performance measuring unit 1400 and tape 2005. In one example embodiment, the tape 2005 can be kinesio tape, medical tape, or any other type of elastic therapeutic tape, such as those tapes having an elastic cotton strip with an acrylic adhesive. The athlete places the athletic performance measuring unit 1400 against the surface 2010 of the athlete's skin and tapes the unit to the surface 2010 using the kinesio tape. The athletic performance measuring unit 1400 can be taped to any portion of the athlete's body, including, but not limited to the stomach region, the back area or anywhere along the arms or legs of the athlete.

Figure 21A:
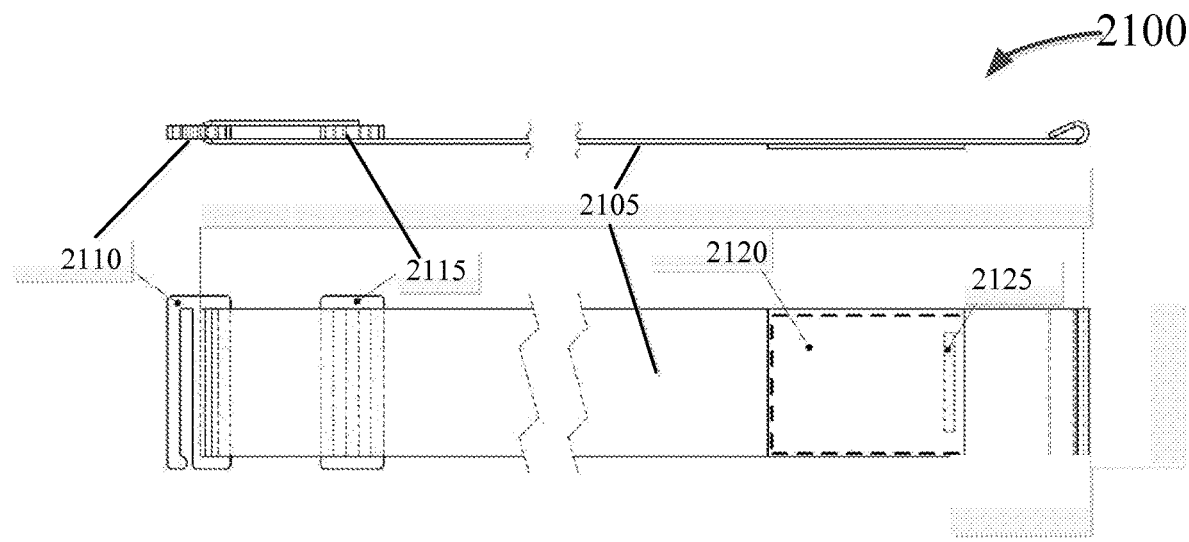
FIGS. 21A and 21B are graphic illustrations of belts for holding the athletic performance measuring unit of FIGS. 14A-H and securing the unit to the body of an athlete in accordance with one exemplary embodiment of the disclosure.
Figure 21B:
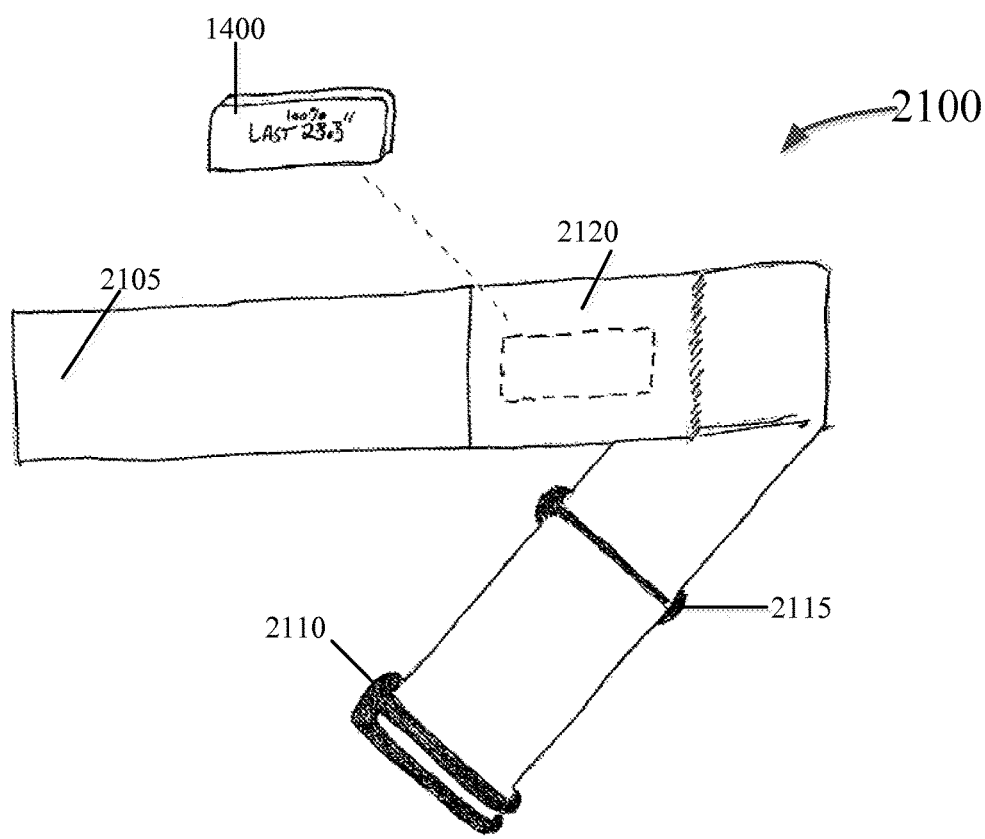

FIGS. 21A and 21B are graphical illustrations of belts 2100 with an integral pouch for holding or integrating the athletic performance measuring unit 1400 and securing the unit 1400 to the athlete's body in accordance with one exemplary embodiment of the disclosure. Referring to FIGS. 14A-H, 21A, and 21B, each of the exemplary belts 2100 can include a belt body 2105 having a first end and an opposing, distal second end and one or more belt clips 2110, 2115 for coupling opposing ends of the belt body 2105. The belt body 2105 can be elastic, semi-elastic, or generally rigid. Along at least one side of the belt body 2105 can be included a pocket 2120 for receiving the athletic performance measuring unit 1400. In one example embodiment, the pocket 2120 can include enclosed top and bottom edges and one side edge that is also enclosed. The opposing side edge can include an opening for passing the athletic performance measuring unit 1400 into the pocket 2120. This opposing side edge may include one or more mechanisms for opening and closing the pocket 2120, such as Velcro or magnets for example, for closing the side edge and trapping the unit 1400 within the pocket 2120. In an alternative embodiment, all sides of the pocket 2120 can be enclosed such that athletic performance measuring unit 1400 is integrated into the belt body 2105. In certain example embodiments, all or a portion of the pocket 2120 may be made of a translucent or transparent material so that the display 1420 of the unit 1400 can be viewed when the unit 1400, which may or may not include an outer housing 1405, is inside of the pocket 2120. Each of the belts 2100 may be configured to go around the waist, arm, or leg of an athlete or animal in certain example embodiments.

Figure 22A:
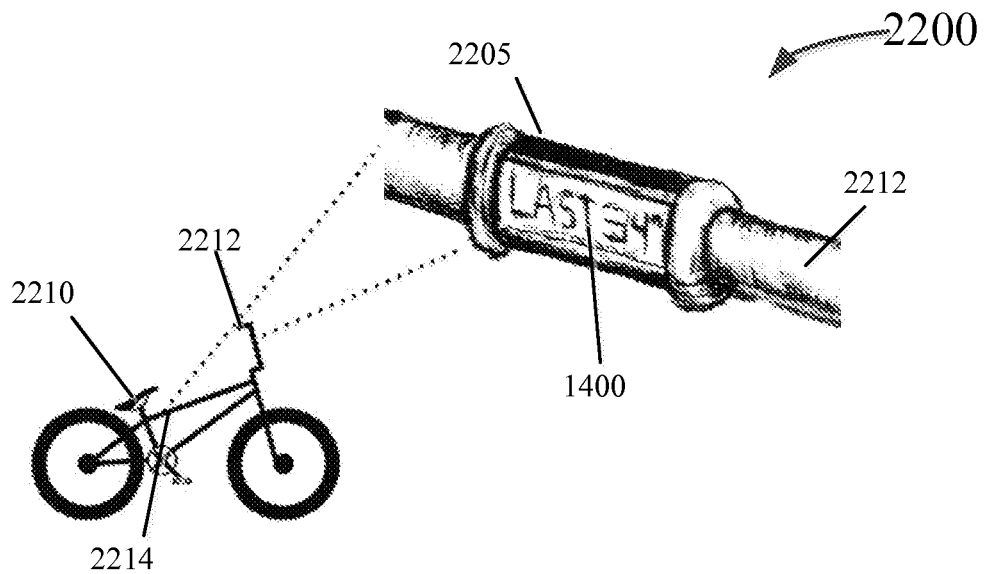
FIGS. 22A-22C are graphical illustrations of multiple configurations for securing or integrating the athletic performance measuring unit to a bicycle or motorcycle in accordance with one exemplary embodiment of the disclosure.
Figure 22B:
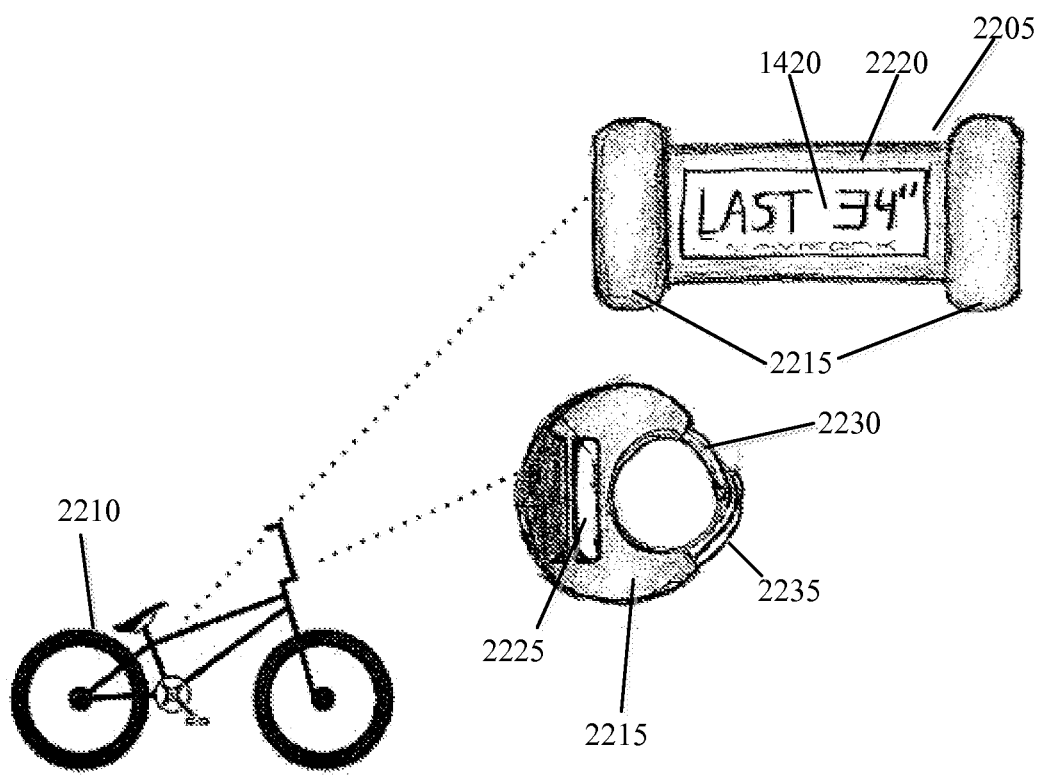
Figure 22C:
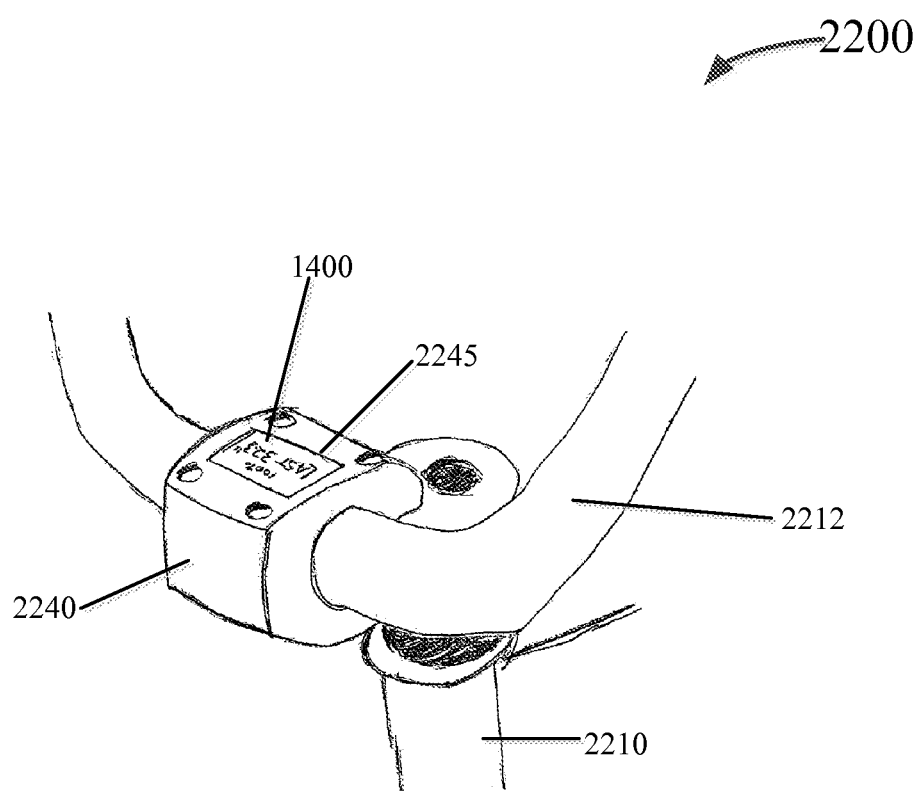

FIGS. 22A-22C are graphical illustrations of multiple methods 2200 for securing and/or integrating the athletic performance measuring unit 1400 to a bicycle in accordance with one exemplary embodiment of the disclosure. While FIGS. 22A-22C make particular reference a bicycle, the teachings should not be so limited. For example, similar mechanisms to those described may also be used to couple or integrate the athletic performance measuring unit 1400 to a motorcycle, scooter, snowmobile, all-terrain vehicle, motorcross bike, rally sport automobile or other similar mode of personal transportation that may be used by an athlete. Referring now to FIGS. 14A-H and 22A-C, the first example method and apparatus includes a measuring unit securing device 2205 that is configured to be integrated, coupled, or removably coupled to the handlebars 2212, bike stem, or another portion of the frame 2214 of a bicycle 2210.

In one example embodiment, the measuring unit securing device 2205 includes a unit housing 2220 having a first end and an opposing second end. The unit housing 2220 can have a cylindrical or partially cylindrical shape along its interior edge in certain example embodiments and can be constructed of rubber or another elastic material, plastic, metal, or any other suitable material. Further, the unit housing 2220 may have a partially curved and partially planar surface along its outer surface. Each opposing end of the unit housing 2220 can include a cushioning member 2215. In one example embodiment, the cushioning member 2215 is made of rubber; however, other cushioning or shock-absorbing materials may be substituted without departing from the scope of this disclosure. In one example, the cushioning member 2215 and the unit housing 2220 are made of the same material. In certain example embodiments, each cushioning member 2215 can also have a cylindrical or partially cylindrical shape. Further, each cushioning member 2215 can have a diameter that is greater than the diameter of the unit housing 2220 in certain example embodiments.

For a unit housing 2220 and/or cushioning members 2215 that are partially cylindrical in shape, the example device can further include fastening members 2230 and 2235 extending from each end of the unit housing 2220 and/or the cushioning members 2215 that are configured to be coupled to one-another to hold the measuring unit securing device 2205 in place on the handle bars 2212 or frame 2214 of the bicycle 2210. Alternatively, the unit 1400 or portions of the unit 1400, which may or may not include an outer housing 1405, may be integrated into the handle bars 2212, frame 2214 or bike stem of the bicycle 2210. Similarly, the unit 1400, which may or may not include an outer housing 1405, can be integrated into the steering wheel/mechanism, dashboard or another portion of a motorcycle, scooter, snowmobile, all-terrain vehicle, motorcross bike, or rally sport automobile.

In certain example embodiments, the fastening members 2230 and 2235 are made of Velcro. Alternatively, buttons, snaps, or other known types of securing members including but not limited to, screws, rivets, studs, and eyelets may be used. A measuring unit insertion opening 2225 can be positioned along one or both ends of the measuring unit securing device 2205. In operation, the athlete can slide the athletic performance measuring unit 1400 into the opening 2225 until the display 1420 is capable of being viewed in the unit housing. In an alternative embodiment, the unit 1400 may already be integrated into the opening 2225 and sold with the bicycle 2210 as a whole or as an additional part that can be individually purchased. In certain example embodiments, the unit housing 2220 includes a cut-out section for viewing the display 1420 of the athletic performance measuring unit 1400. Alternatively, the unit housing 2220 includes a transparent or translucent panel through which the display 1420 can be viewed.

FIG. 22C presents an alternative measuring unit securing device 2240 for integrating the athletic performance measuring unit 1400 to a bicycle. For example, in FIG. 22C, the alternative measuring unit securing device 2240 includes an opening 2245 in the bike stem for receiving and securing/integrating the athletic performance measuring unit 1400. For example the unit 1400 may be integrated into the bike stem and sold with the bicycle 2210 as a whole or as a separate part with the unit 1400 already integrated therein. Alternatively, the unit 1400 may be inserted into and removed from the opening 2245 as desired by the user. While the example is shown integrated into the bike stem 2240, alternatively the unit 1400 can be integrated into any other portion of the bicycle 2210 or a motorcycle, scooter, snowmobile, all-terrain vehicle, motorcross bike, or rally sport automobile. For example, the athletic performance measuring unit 1400 can be inserted into the measuring unit securing device 2240 from either the back side or the front side and the device 2240 can be removably coupled to the handlebars 2212 by tightening one or more fasteners, such as screws, bolts, nuts, etc. to reduce the radius of curvature of the inner surface of the measuring unit securing device 2240 thereby tightening the device 2240 to the bicycle. The alternative measuring unit securing device 2240 can be constructed of metal, rubber or another elastic material, plastic, or any other suitable material. As with the device 2205, the device 2240 may include cushioning and/or shock absorbing materials or features to protect the athletic performance measuring unit 1400, which may or may not include an outer housing 1405, while in use.

In yet another alternative embodiment, the handlebars 2212, gooseneck (bike stem) or another portion of the frame 2214 of the bicycle 2210 can have an opening machined therein having a size and shape to slidably receive the athletic performance measuring unit 1400 at least partially therein or to integrate the unit 1400 therein to thereby permanently affix the unit 1400 to the bicycle 2210. In addition, the machined-out portion of the bicycle 2210 may include cushioning and/or shock absorbing materials or features to protect the athletic performance measuring unit 1400, which may or may not include an outer housing 1405, while in use.

Figure 23A:
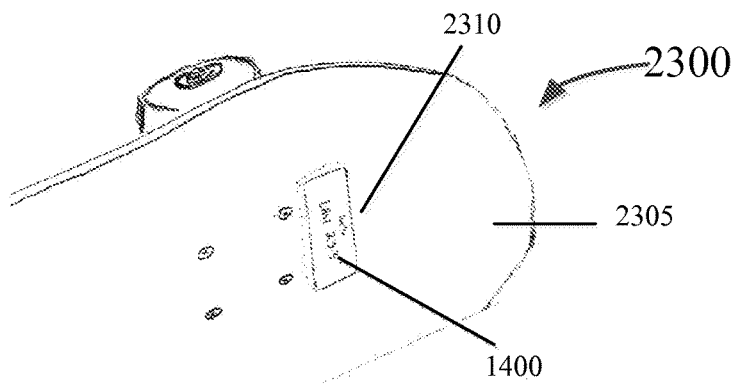
FIGS. 23A-23C are graphical illustrations of multiple configurations for securing or integrating the athletic performance measuring unit to a skateboard or other similar device in accordance with one exemplary embodiment of the disclosure.
Figure 23B:
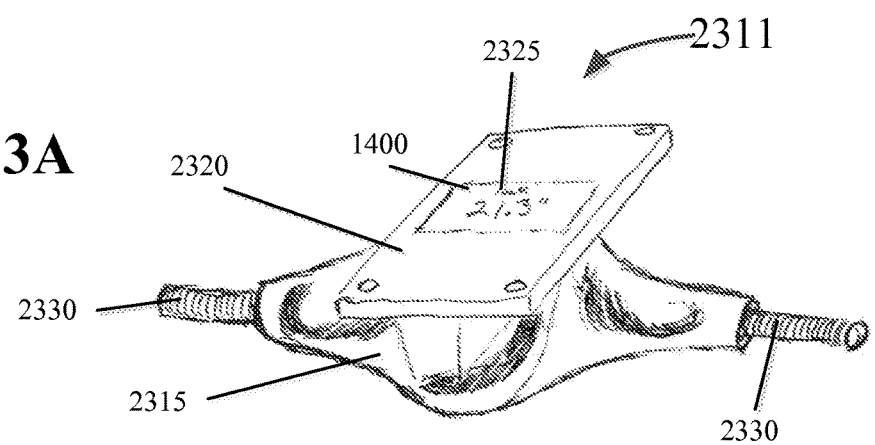
Figure 23C:
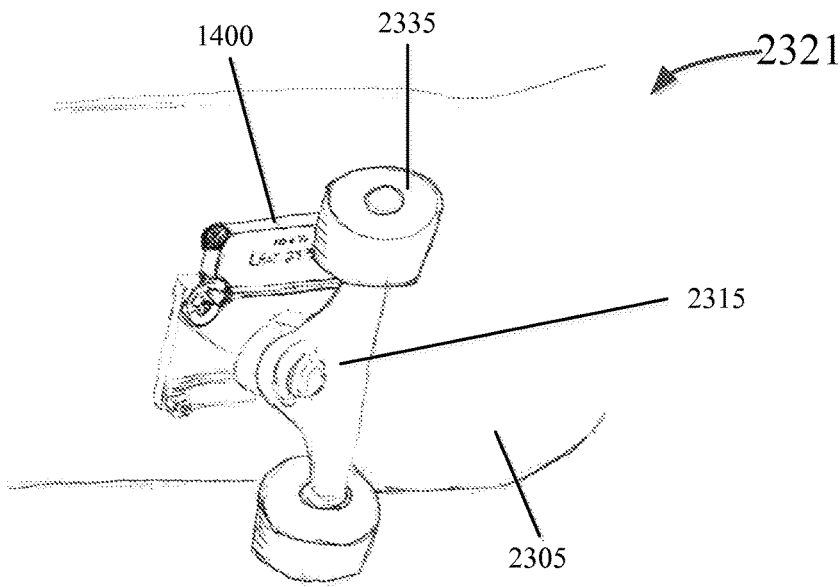

FIGS. 23A-23C are graphical illustrations of multiple configurations for securing or integrating the athletic performance measuring unit 1400 to a skateboard or other similar device in accordance with one exemplary embodiment of the disclosure. While the examples of FIGS. 23A-23C depict skateboards, other similar devices, such as surfboard, wakeboard, windsurfing board, kite surfing board, scooter, skis, snowboard, any other device with a planar or substantially planar surface, or the like may be similarly outfitted/integrated with the athletic performance measuring unit 1400. Now referring to FIGS. 14A-H and 23A-C, the first example configuration 2300 includes a skateboard 2300 having a board or skateboard deck 2305 (e.g., a planar or substantially planar surface). An opening 2310 can be milled in the skateboard deck 2305. For example, the opening 2310 can be just slightly larger than the dimensions of the athletic performance measuring unit 1400. The athletic performance measuring unit 1400 can then be placed into the opening 2310 and secured to or integrated into either the skateboard deck 2305 or the axle of truck 2311 of the skateboard. As such, a skateboard deck 2305 with integrated athletic performance measuring unit 1400 could be sold as a separate part and added to a skateboard. In addition, adjacent or surrounding the athletic performance measuring unit and within the opening 2310 cushioning and/or shock absorbing materials or features may be included to protect the athletic performance measuring unit 1400, which may or may not include the housing 1405, while in use. As discussed above, while the example of FIG. 23A presents a skateboard, similar placement and milling configurations could also be accomplished with a surfboard, wakeboard, windsurfing board, kite surfing board, scooter, skis, snowboard, any other device with a planar or substantially planar surface, or the like.

The next example configuration 2311, in FIG. 23B, includes an exemplary axle or truck 2315 of the skateboard 2300. The truck 2315 includes a mounting plate 2320 for mounting the truck 2315 to the skateboard deck 2305. The truck 2315 also includes axle posts 2330 upon which the wheels 2335 may be coupled. In this example configuration 2311, the mounting plate 2320 of the truck 2315 can be milled out to create an opening 2325 or cavity in the mounting plate 2320 with dimensions slightly larger than the dimensions of the athletic performance measuring unit 1400. The athletic performance measuring unit 1400 can then be placed into the opening 2325 and secured to or integrated into the mounting plate 2320 using an adhesive, Velcro, a transparent cover plate or other similar means for adhering. Further, in certain example embodiments, the skateboard deck 2305 may also be milled out to create an opening, such as 2310 or could include a transparent area in the skateboard deck 2305 that is aligned with the opening 2325 so that information from the athletic performance measuring unit 1400 can be viewed. As such, a truck 2315 with integrated athletic performance measuring unit 1400 could be sold as a separate part and added to a skateboard. In addition, adjacent or surrounding the athletic performance measuring unit 1400 and within the opening 2325 cushioning and/or shock absorbing materials or features may be included to protect the athletic performance measuring unit 1400, which may or may not include the housing 1405, while in use.

The next example configuration 2321, in FIG. 23C, includes an exemplary axle or truck 2315 and the skateboard deck 2305 of the skateboard 2300. In this configuration, the athletic performance measuring unit 1400 can be coupled to or integrated into the bottom side of the skateboard deck 2305 and on or adjacent to the truck assembly 2315. The athletic performance measuring unit 1400 can be attached to or integrated into the skateboard deck 2305 and/or the truck 2315 with screws, bolts, adhesive, Velcro, or any other attachment means known to those of ordinary skill in the art. In addition, adjacent or surrounding the athletic performance measuring unit 1400 cushioning and/or shock absorbing materials or features may be included to protect the athletic performance measuring unit 1400, which may or may not include the housing 1405, while in use.

Further, the athletic performance measuring unit 1400 can also be coupled or integrated into a firearm. For example, the unit 1400 may be coupled or integrated into the barrel, stock, and/or grip of a firearm or into any other part of the gun. In this example, the sensor 120 of the unit 1400 can be configured to measure the amount or recoil of the firearm when the firearm is discharged.

Also, the athletic performance measuring unit 1400 can be coupled or integrated into collars, harnesses and/or saddles for animals, such as dogs and horses. For example, the unit 1400 can be removably coupled to a collar or harness using the clip 1500 of FIG. 15. Alternatively, the unit 1400 can be integral with and non-removable from the collar or harness. Similar opportunities are available for the saddles for horses. In these examples the sensor 120 for the unit 1400 can be configured to measure the height and length of a jump by a horse or a dog during, for example competitions involving animals.

In another example embodiment, the unit 1400 can be coupled to or integrated into balls of all kinds, shapes, and sizes, including volleyballs, softballs, baseballs, footballs, and golf balls, NERF® balls. Further the unit can be coupled to or integrated into non-sports related products, such as, for example, catapult toys. For any of the above, the unit 1400 can be configured to provide height sensor data and horizontal distance sensor data, as well as other positional sensor data.

In addition to the potential for personal improvement derived through the use of the athletic performance measuring unit 1400, the unit 1400 can also, in certain example embodiments, allow viewers of a game, whether at the game or at a location remote from the game, to track, analyze, and tout athletic performance data for the athlete as generated by the unit 1400 in real-time or near real-time. For example, sensor data can be collected by the sensors 120 of the athletic performance measuring unit 1400 and the athletic performance parameter(s) determined (e.g., jump height, touch height, or swing speed) and transmitted via the onboard antenna 130 to one or more other PPUs and/or non-personal computing devices, either directly or indirectly. Alternatively, the sensor data can be collected by the sensors 120 of the athletic performance measuring unit 1400 and transmitted via the onboard antenna 130 to one or more PPUs (e.g., one or more smart devices) and/or non-personal computing devices (e.g. the web server, network server, scoreboard, etc.) for calculation of the one or more athletic performance parameters. In certain examples, these other PPUs or non-personal computing devices receive the sensor data and/or athletic performance parameter for the local display of the athletic performance parameter or for forwarding of the athletic performance parameter onto another communication media such as the Internet, a web site driven by a web server, an interactive television or some other network. In one example one or more dedicated servers may be provided that can each be configured for the collection, formatting, and transmission of this athletic performance parameter data in real-time or near real-time onto one or more other networks. In so doing, fans will have the ability to watch and monitor their favorite players' athletic performance parameters simultaneously as actions occur in real-time or near real-time during a game. In certain example embodiments, the fan can choose which player or players to monitor, the athletic performance parameter(s) to monitor and the PPU (e.g., a laptop computer, a personal computer, a smart device, another mobile device, such as a digital assistant, PDA, mp3 player or other audio players, cell phone, pager, beeper, radio, portable television, portable DVD player, other video playing device, calculator, watch, etc.) or non-personal computer (e.g., web server, network server, stadium scoreboard, jumbotron or other non-personal display within the stadium or arena.

In certain example embodiments, transmission to different communication media such as stadium scoreboards, interactive TVs, PPUs, and or web servers, can be controlled locally, as shown below in FIG. 25 or determined and/or controlled by a central server, network computer, and/or web server. For example, the individual athletic performance measuring units 1400 can communicate to a server or other network computer, discussed below, which in turn can stream, download or transfer data feeds based on subscriber preferences to any Internet-capable device. In addition, the server or network computer can also provide real-time or near real-time athletic performance parameter data for television, cable, satellite, and Internet viewers as well.

Figure 24:
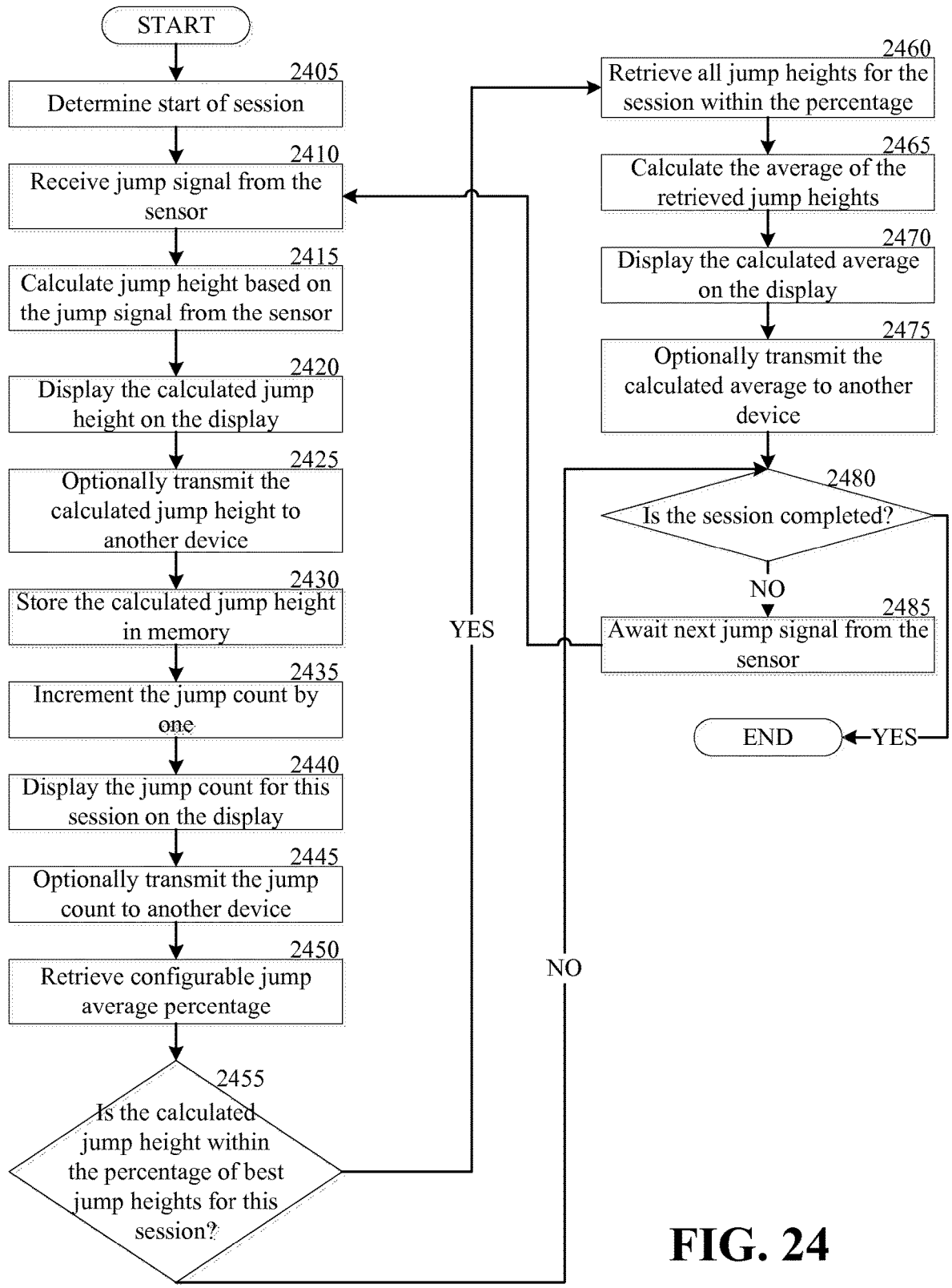
FIG. 24 is a flow chart of a method for sensing, calculating, and displaying athletic performance parameters during and athletic session, in accordance with one exemplary embodiment of the disclosure.

FIG. 24 is a flow chart of an example method 2400 for sensing, calculating, and displaying athletic performance parameters during and athletic session using, for example, the athletic performance measuring unit 1400 of FIGS. 14A-H, in accordance with one exemplary embodiment. The exemplary method 2400, described below, may be performed by the athletic performance measuring unit 1400, a PPU, and/or the non-personal computing device. The exemplary method 2400 will be described with reference to jump height as the athletic performance parameter; however, this is only for purposes of example as other athletic performance parameters could be substituted for, and should each be individually read as being a part of this method. As such, where the discussion of the method below and the drawings state a jump signal or a jump height, any other athletic performance parameter could be substituted, such as a swing and swing speed.

Referring now to FIGS. 1, 14A-H, and 24, the exemplary method 2400 begins at the START step and proceeds to step 2405, where the start of a session is determined at the athletic performance measuring unit 2400. In one example, a user can start a session by pressing the button 1445 on the unit 1400 to enter the proper mode based on information presented on the display 1420 for starting a session by the computing unit 100. In another example, as long as the unit 1400 is already turned on, as soon as unit 1400 is in communication (e.g., wireless communication or wired communication) with a PPU or non-personal computing device, the unit is capable of automatically transmitting sensor data and/or athletic performance parameter data to the PPU or non-personal computing device. In step 2410, a jump signal containing sensor jump data is received by the one or more sensors 120. In certain example embodiments, the sensors 120 sense an action, such as a jump by an athlete, and transmit or otherwise provide that sensor data to the computing unit 100. Alternatively, the sensors 120 are continuously transmitting or otherwise providing sensor data to the computing unit 100. The jump height is calculated based on the sensor jump data received from the sensors 120 in step 2415. For example, the jump height can be calculated by the computing unit 100. Alternatively, the sensor jump data can be transmitted by the unit 1400 by way of the antenna 130 to a PPU or non-personal computing device remote from the unit 1400 for jump height and other calculations discussed in steps 2430, 2435, and 2450-2465. In step 2420, the calculated jump height can be displayed on the display 1420 of the athletic performance measuring unit 1400, similar to that shown in FIG. 14E. In addition, as an optional feature, the calculated jump height can be transmitted to another device in step 2425. For example, the computing unit 100 can transmit the jump height via the antenna 130 to one or multiple PPUs and/or non-personal computing devices for display on those devices via, for example Wi-Fi or Bluetooth transmission. Alternatively, where the PPU or non-personal computing device calculates the jump height, the PPU or non-personal computing device can transmit the calculated jump height to other PPUs, non-personal computing devices, and/or the unit 1400 for display on the unit 1400.

Figure 25:
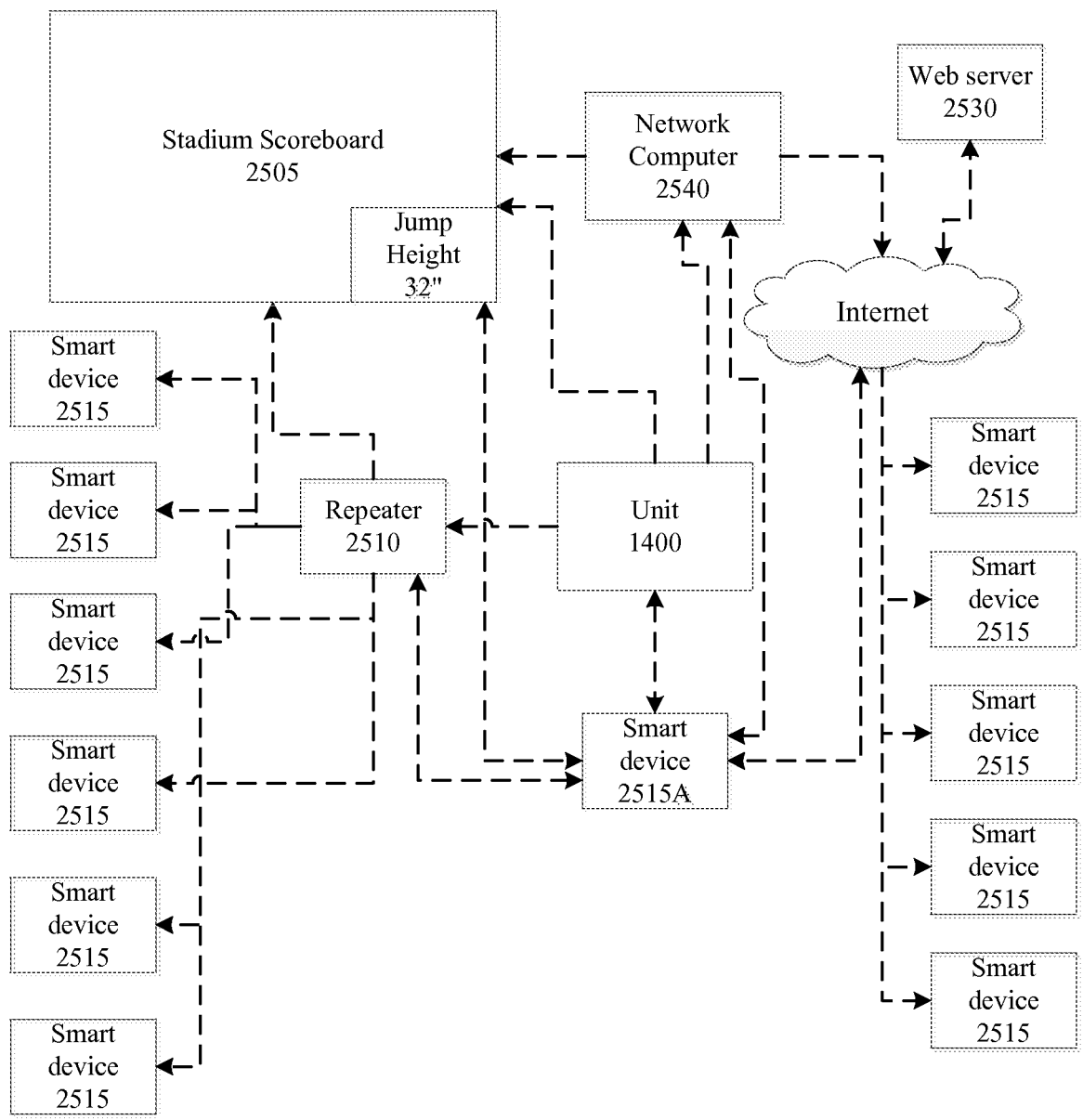
FIG. 25 is a graphical illustration of the real-time or near real-time communication of athletic performance data by the athletic performance measuring unit with other electronic devices in accordance with one exemplary embodiment of the disclosure.

FIG. 25 is a graphical illustration of the real-time or near real-time communication system for the communication of athletic performance parameters by the athletic performance measuring unit 1400 or the PPU (e.g., smart device 2515A) with other devices in accordance with one exemplary embodiment of the disclosure. As shown in FIG. 25, in one example, the athletic performance measuring unit 1400 can transmit the calculated jump height or raw sensor data either directly or indirectly to one or more PPUs, such as one or more smart devices 2515, and/or one or more non-personal computing devices, such as a network computer 2540, a wireless communication repeater 2510, and/or a stadium scoreboard 2505 or other display within a stadium, arena or field of play in real-time or near real-time. For example, the athletic performance measuring unit 1400 can either directly transmit the calculated jump height to the smart devices 2515 via Wi-Fi, Bluetooth, or OTA communication or the unit 1400 can transmit the calculated jump height data to a repeater that then transmits the data to the smart phones 2515 and tablets 2520. Alternatively, the unit 1400 can transmit the raw sensor data to the smart device 2515A, which can calculate the calculated jump height and the smart device 2515A can transmit the calculated jump height to other PPUs (e.g., smart devices 2515, non-personal computing devices (e.g., network computer 2540, scoreboard 2505, the web server 2530 (via the Internet, and/or the repeater 2510)). In addition, the athlete can set up their own PPU, such as a smart device 2515A to receive the calculated jump height data and pass that calculated jump height data along with certain identification information of the athlete to a web server 2530, such as a social web server, for display on a posting board of the web server 2530 or on the athlete's personal page of that web server 2530. This can be done in real-time or near real-time, after a session ends, or upon command from the athlete either at the athletic performance measuring unit 1400 or at the smart device 2515.

Figure 26A:
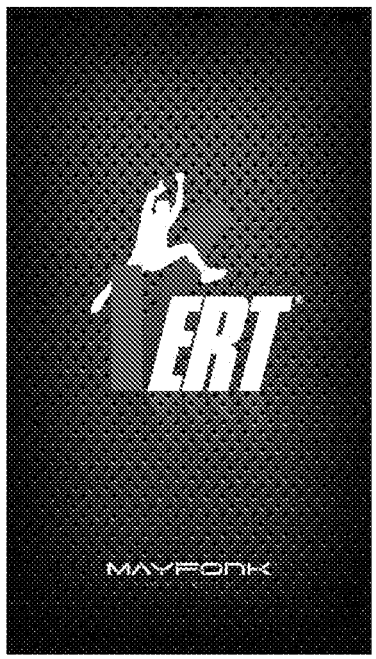
FIGS. 26A-G present example depictions of screenshots for a social mobile application communicably connected to a web server for the display of athletic performance data measured by the athletic performance measuring unit in accordance with one exemplary embodiment of the disclosure.
Figure 26B:
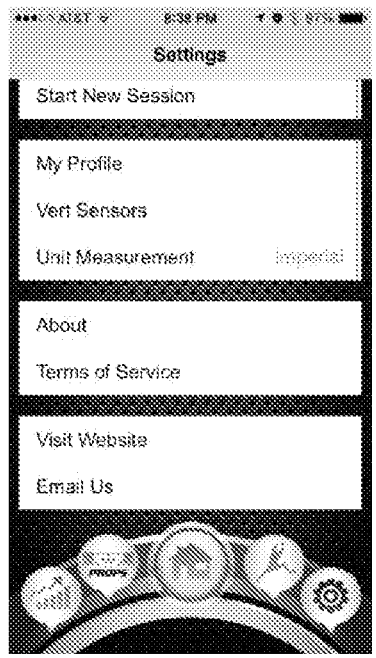

FIGS. 26A-G present example depictions of screenshots for a social media mobile application connected to web server 2530 for the display of athletic performance data measured by the athletic performance measuring unit 1400, the PPU 2515 and/or a non-personal computing device in accordance with one exemplary embodiment of the disclosure. FIG. 26A depicts a screenshot of an example front page or loading page for the exemplary social media mobile application connected to the web server 2530. FIG. 26B depicts a screenshot of an example settings page for the social media mobile application connected to the web server 2530. In one example the settings page can provide an athlete with the ability to communicably link the athletic performance measuring unit 1400 with the web server via a unique IP address. The communication can include the sensor data and/or athletic performance parameters measured and/or calculated by the unit 1400, PPU 2515, or non-personal computing device, software upgrades and updates downloaded from the web server to the unit 1400 (via, for example, the PPU) and changes to parameters being measured by the unit 1400 based on changes to the software for the unit 1400 or changes to the sensors 120 providing information to the unit 1400, the PPU and/or the non-personal computing device, each and any of which can be downloaded from the web server to the unit 1400 either via direct wire connection to a laptop or personal computer or wirelessly via, for example, the Internet and optionally via the PPU. In addition, the athlete can create a profile or personal page on the web server 2530 by providing, for example, personal information for display on the web server 2530, uploading photos or videos for display on the web server 2530, providing personal data, such as name, age, height, weight, standing touch height (for use in calculating a touch height based at least in part on the calculated jump height), and/or selecting friends who also have profiles or personal pages on the web server so that they can see updates by friends of athletic performance data and so friends can see their updates of athletic performance data.

Figure 26C:
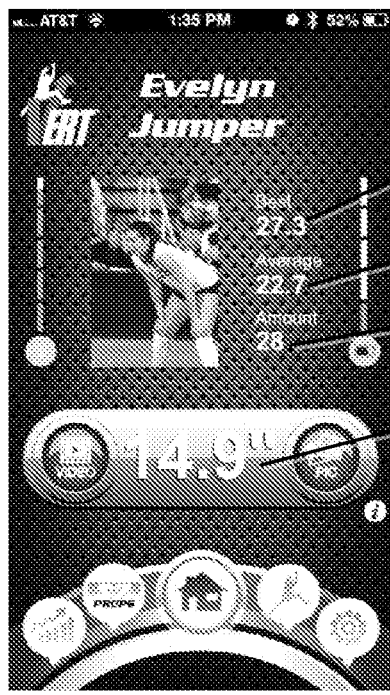
Figure 26D:
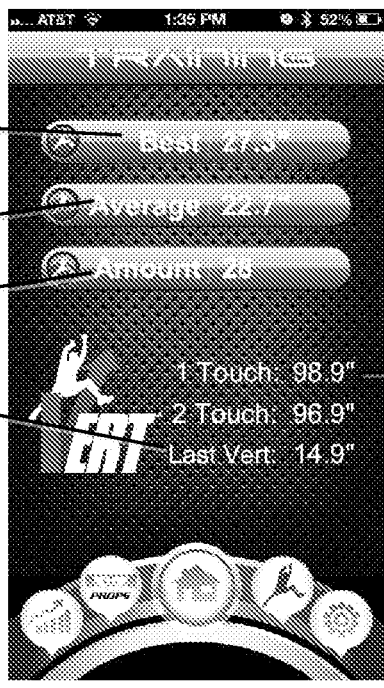

FIGS. 26C and 26D present two example depictions of screenshots of a social media mobile application connected to a web server and presenting a profile or personal page for an athlete. For example, FIG. 26C can be an example of how information about an athlete may be presented to friends or other users viewing the website 2530 while FIG. 26D can be an example of how information about the athlete may be presented to the athlete when viewing their own profile on the website. As can be seen in FIGS. 26C and 26D, the pages can include the latest calculated athletic performance parameter 2605, in this case the most recently calculated jump height 2605, the number of jumps 2610, the average jump height 2615, the touch jump height 2620, and/or the best or peak jump height 2625.

Figure 26E:
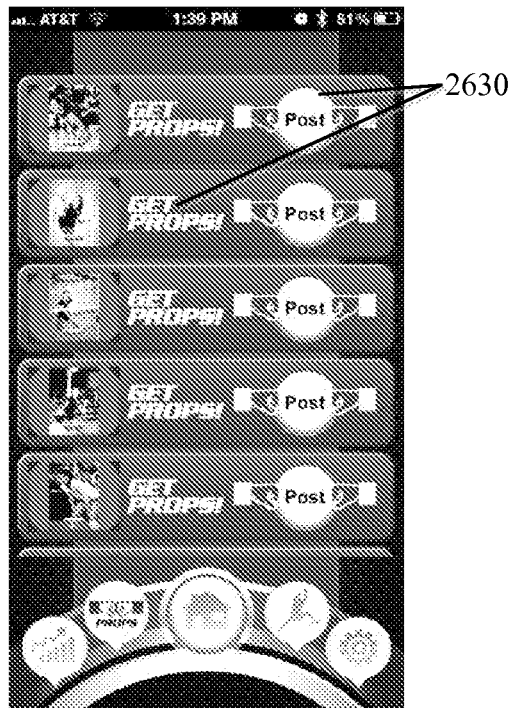
Figure 26F:
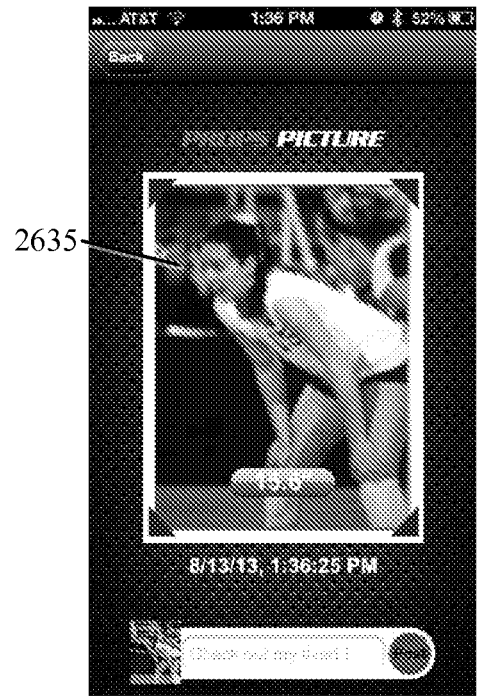

FIG. 26E presents an example depiction of a screenshot of a social media mobile application connected to a web server and presenting a friends feed screen for an athlete on the web server 2530. For example, the feed screen can provide a listing of athletic performance data received by the web server 2530 for people that the athlete is friends with or whom the athlete has chosen to follow (such as famous athletes). In one example embodiment, the feed screen can list athletic performance data updates in an ordered format, such as most recent, most viewed, or alphabetically by the name of the friend or person being followed, for example. The feed screen can also provide the name and/or picture of the friend or person being followed as well as the athletic performance data (e.g., jump height). In certain example embodiments, the athletic performance data may be the peak performance data for a particular session, the average of the performance data, and/or the most recently measured and/or calculated athletic performance data. The feed screen can also provide the viewer of the data the ability to give a friend or other person they are following "props" for their performance by selecting a props button 2630 that can be positioned adjacent to the athletic performance data. This "props" is similar to congratulating or liking another person's performance. Props can be posted on the feed screen, props can be given by the athlete or props can be received by the athlete for one or more particular athletic performance parameters, videos, or stats. When the viewer selects the props button 2630, for example, the athlete for which props were given may be notified and a notification of props being received 2635 may be displayed on the athlete's profile or personal page. In addition, a notification of props being received 2635 or given may also be displayed on another social network for the athlete, such as FACEBOOK® and/or TWITTER®. In one example, the athlete's profile or personal page can list the number of props received for a particular athletic performance data/video/stat and/or the names of the persons giving the athlete props for their performance.

Figure 26G:
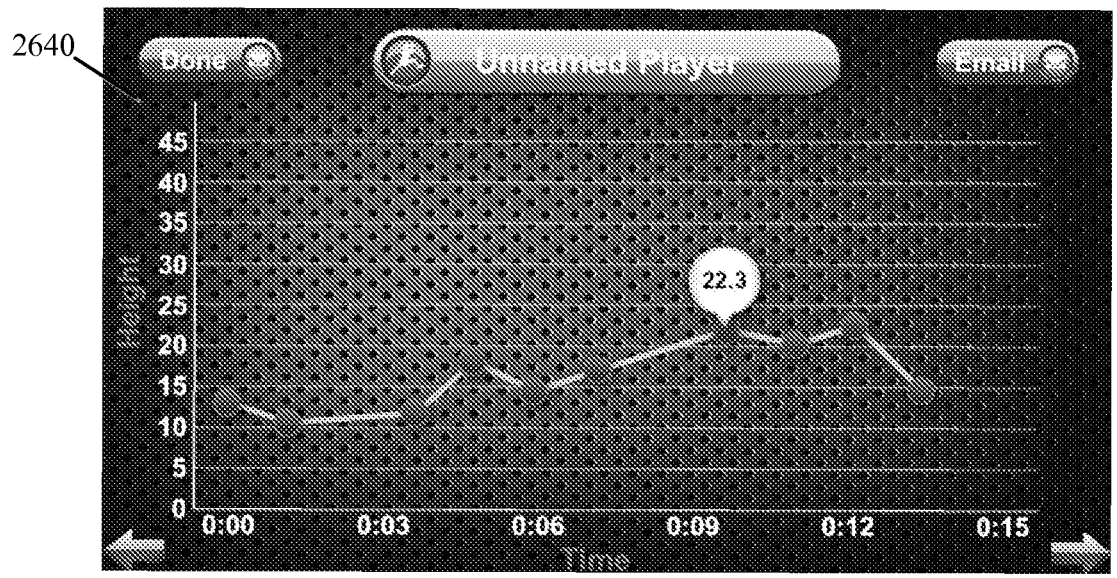

In addition, the web server 2530 can also receive, either wirelessly or by wired connection to a PPU or directly to sensors 120, athletic performance data from the unit 1400 for all or a portion of a session. The web server 2530 can be configured to store this data for later review and can also display all or a portion of the athletic performance data from a session in numerous ways. FIG. 26G presents an example depiction of a screenshot of a social media mobile application connected to a web server and presenting the athletic performance data. In FIG. 26G, the athletic performance data is an athlete's jump height and the web server 2530 presents the data in the form of a line graph 2640 over the time period of the session. However, alternate graphing and data manipulation tools are available based on the type of athletic performance data and the needs of the viewer. In addition, the graph may be presented with certain data highlighted and/or the jump data may be linked to video or audio also stored on the web server 2530 and associated with the athlete so that a viewer could select the particular athletic performance data and be presented with the video or audio associated with that particular athletic performance data point.

Returning to FIG. 25, the athletic performance measuring unit 1400 or a PPU can also transmit the calculated jump height with or without certain identification information of the athlete either directly to a stadium scoreboard 2505 or indirectly to the stadium scoreboard 2505 via the network computer 2540. In addition, the network computer 2540 can be configured to transmit the calculated jump height data to other PPUs that are local or remote from the athletic event by transmitting the data via the Internet, intranet, web server 2530 or any other network. In this manner, fans watching an athletic event, either at the event or remote from the event, can receive the calculated athletic performance parameter on their own PPUs in real-time or near real-time and those at the event can also view the calculated athletic performance parameter on one or more scoreboards 2505 or video boards at the athletic event.

In addition, advertising can be linked to the display of these athletic performance parameters for the enjoyment of the fans. For example, in the case of a basketball game, the retrieval and display of athletic performance parameters from one or more athletic performance measuring units 1400 or PPUs 2515 on the stadium scoreboard 2505, suite monitors, arena monitors, or the like and/or for direct or indirect transmission to the PPUs of fans within the arena could be endorsed by one or more specific "advertisers" and the athletic performance parameters could be displayed in real-time or near real-time as the game (and player) results are posted during broadcast of the event via television, radio, and the Internet. For example, fans with smart devices 2515 or other PPUs that have, for example downloaded an application, such as a VERT® mobile application, on their smart device 2515 or other PPU, can give props to players/plays that occur during the athletic even. An advertiser can select a group (anything more than one) of players/plays that have received the most props during the athletic even. The advertiser can send the selected group of players/plays to the PPUs 2515 of the fans at the athletic event who have downloaded the VERT® mobile or regular application and/ or who have given at least one player/play props during the game. The fans can then be asked to vote for the best player/play of the night (e.g., "the best Vert of the night, sponsored by VERIZON®"). The fan can be presented with an ad from the advertiser (in this example VERIZON® while being given the opportunity to vote. If the fan votes, it can be transmitted from the PPU 2515 to a non-personal computing device (e.g., web server 2530, network computer 2540, and/or scoreboard 2505, where the votes can be tabulated. Once the votes are received and tabulated, the advertiser can display the winner of the vote along with the name of the advertiser or an ad from the advertiser on the scoreboard and/or transmit the winning information along with the name of the advertiser and/or an ad from the advertiser to the PPUs 2515 of the fans for display on the PPUs 2515 of the fans, for example, at the athletic event.

In step 2430 of FIG. 24, the calculated jump height can be stored in a memory storage area 140 of the unit 1400, the PPU (e.g., smart device 2515A), and/or a non-personal computing device (e.g., web server 2530, network computer 2540, etc.). For example, the athletic performance measuring unit 1400 may include volatile memory, non-volatile memory, and/or a combination of both and the calculated jump height may be stored in either of these types of memory, which may be included within the housing 1405 of the unit 1400.

Alternatively, the PPU (e.g., smart device 2515A) or non-personal computing device (e.g., web server 2530, network computer 2540, etc.) may include non-volatile memory and/or volatile memory and the calculated jump height may be stored in either of these types of memory. In step 2440, a jump counter can be incremented by one based on the sensed jump data and/or the calculated jump height. In certain example embodiments, the unit 1400 may calculate (count) and store the number of jumps (based on sensed jump data from the sensors 120) that an athlete has completed during a session or over multiple sessions. In an alternative embodiment, the PPU (e.g., the smart device 2515A) or non-personal computing device (e.g., web server 2530, network computer 2540, etc.) may calculate (count) and store the number of jumps (based on sensed jump data from the sensors 120) that an athlete has completed during a session or over multiple sessions.

The current jump count, as represented in the jump counter, can be displayed on the display 1420 of the unit 1400 in step 2440 or on a display of the smart device 2515A. For example, the computing unit 100 can retrieve the current jump count from memory 140 and can present it for display on the OLED display 1420 of the athletic performance measuring unit 1400 in a manner similar to that shown in FIG. 14F. Alternatively, the smart device 2515A can retrieve the current jump count (e.g., from memory) and can present it for display on the smart device 2515A. In addition, as an optional feature, the jump count can be transmitted to another device in step 2445. For example, the computing unit 100 (via the antenna 130) and/or the PPU 2515A can transmit the jump count to one or multiple PPUs and/or non-personal computing devices for display on those devices via, for example Wi-Fi, OTA, and/or Bluetooth transmission.

In step 2450, the configurable jump average percentage is retrieved. In one example, the PPU (e.g., smart device 2515A) can retrieve the configurable jump average from memory in the device 2515A or from the web server 2530 or the unit 1400. The smart device 2515A can calculate the average jump height that is sensed over a range of jumps sensed by the sensor 120. In certain situations, an athlete or another person may not want the average to include every jump sensed because some jumps may not have occurred with as much intensity and/or the sensor 120 may misconstrue a step for a jump and including this data in the average would throw off the average. In an effort to eliminate outlier data, the smart device 2515A can have stored therein a jump average percentage that sets a limit or range of the sensed jumps that will be used in calculating the jump average. This jump average percentage may be hard coded in the mobile application downloaded onto the smart device 2515A or may be configurable by the user of the PPU 2515A. For example, the jump average percentage can be set at 25%, meaning that only the top 25% highest jumps in a session or over multiple sessions, as desired, are used to calculate a jump average. When configurable, this jump average percentage can be set anywhere from 0.1%-100%. In an alternative embodiment, instead of using a percentage, the average can be calculated on the previous X number of jumps, wherein X can be any number between 2 and 1000. In an alternative embodiment, the computing unit 100 or a non-personal computing device (e.g., the web server 2530) can retrieve the configurable jump average from memory (e.g., memory 140 in the unit 1400). In certain example embodiments, the unit 1400 or the web server 2530 can calculate the average jump height that is sensed over a range of jumps sensed by the sensor 120 based on for example, the jump average percentage discussed above.

In step 2455 an inquiry is conducted to determine if the calculated jump height is within the set jump average percentage for this session. However, as discussed above, it could alternatively be for multiple sessions. In certain example embodiments, the smart device 2515A can compare the currently calculated jump height to the previously calculated jump heights stored in memory of the smart device 2515A based on the jump average percentage to determine if the currently calculated jump height satisfies the set jump average percentage. Alternatively, the computing unit 100 or the web server 2530 can compare the currently calculated jump height to the previously calculated jump heights stored in memory (e.g., memory 140 for the unit 1400) based on the jump average percentage to determine if the currently calculated jump height satisfies the set jump average percentage. If the currently calculated jump height does not satisfy the set jump average percentage, the NO branch is followed to step 2480. Otherwise the YES branch is followed to step 2460, where the smart device 2515A, computing unit 100, or the web server 2530 can retrieve all of the jump heights for the session (including the currently calculated jump height) that fall within the set jump average percentage. For example, if ninety-nine jumps have been stored in memory (e.g., memory of the smart device 2515A or memory 140 of the unit 1400) for the current session, the jump average percentage is set at 25%, and the currently calcualated jump height is within the top 25% of calculated jump heights for the session, then the currently calculated jump height along with highest twenty-four of the previously calculated jump heights will be retrieved to calculate the jump height average.

In step 2465, the jump height average is calculated based on the currently calculated jump height and the retrieved jump heights. In one example, the jump height average is calculated by the smart device 2515A. Alternatively it is calculated by the computing unit 100 of the unit 1400 or the web server 2530. The average jump height can be displayed on the display 1420 of the unit 1400 and/or on the display of the smart device 2515 in step 2470. For example, the smart device 2515 can present the calculated average jump height for display on a display screen. Alternatively, the computing unit 100 can present the calculated average jump height for display on the OLED display 1420 of the athletic performance measuring unit 1400. In addition, as an optional feature, the calculated average jump height can be transmitted to another device in step 2475. For example, the smart device 2515A and/or the computing unit 100 can transmit the calculated average jump height to one or multiple PPUs and/or non-personal computing devices (e.g., the web server 2530, stadium scoreboard 2505, etc.) for display on those devices via, for example Wi-Fi, OTA, or Bluetooth transmission.

In step 2480, an inquiry is conducted to determine if the session is completed. For example, the session may be completed by the athlete turning off the athletic performance measuring unit 1400 using the button 1445. In one alternative example, the session may be completed by the athlete selecting to start a new session using the button 1445. In another alternative example, the session can be ended if the computing unit 100 does not receive sensed jump data or does not determine that a jump has occurred for a predetermined amount of time based on, for example, information provided to the computing unit 100 from the computing unit 100 or a clock/timer 150 communicably coupled to the computing unit 100. The predetermined amount of time can be preset in the computing unit and can be any amount including, for example, any time between 1-100 minutes. The determination as to whether a session has been completed may be determined by the smart device 2515A or the computing unit 100 of the unit 1400. If the session is completed, the YES branch is followed to the END step. Otherwise the NO branch is followed to step 2485, where the unit 1400, such as the computing unit 100 awaits the next jump signal from the sensors 120. The process then returns to step 2410.

In another example embodiment, the athletic performance measuring unit 1400 may be used in a real-time or near real-time environment to assist coaches of athletes to evaluate and track the performance of the athlete or a team of athletes during an athletic competition or practice based on one or more athletic performance parameters being sensed/calculated by the unit 1400 or a PPU (e.g., smart device 2515A). The ability to track athletic performance parameters in real-time or near real-time during an athletic competition or practice can provide the coach with insight into whether the athlete is, for example, becoming fatigued or reaching a limit, such as a jump limit, and should be replaced on the field of play.

Figure 27:
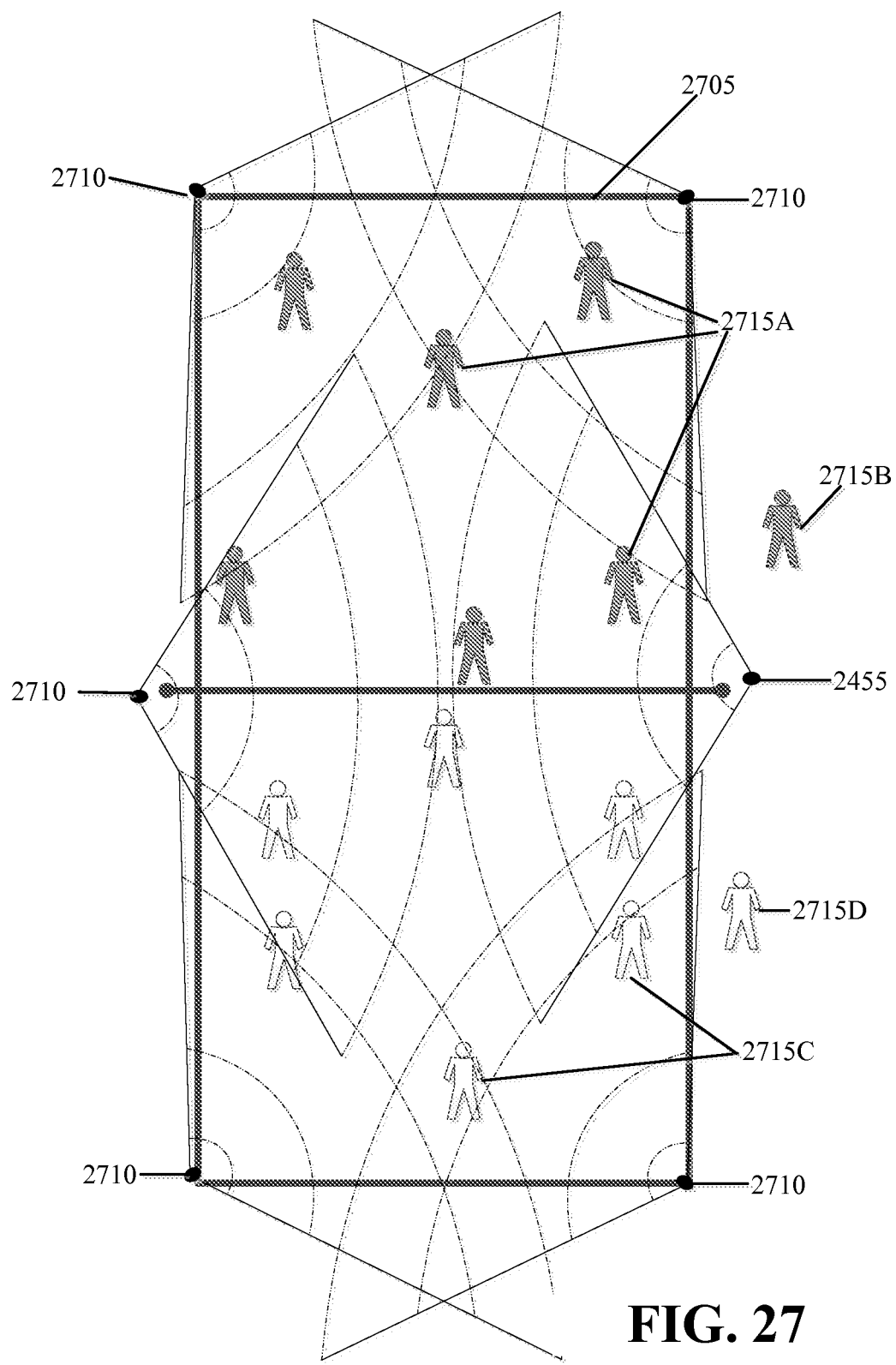
FIG. 27 is a block diagram depicting an example system 2700 for monitoring one or more athletic performance parameters on a field of play in accordance with one example embodiment of the disclosure.

FIG. 27 is a block diagram depicting an example system 2700 for monitoring positional changes of athletes and/or one or more athletic performance parameters on a field of play in accordance with one example embodiment of the disclosure. Referring now to FIGS. 14A-H and 27, the exemplary system 2700 can be set up around a field of play 2705. The field of play 2705 can be any type of competition field, including a football field, baseball field, basketball court, hockey rink, or the volleyball court 2705 depicted in FIG. 27.

Near the field of play 2705 can be one or more transceivers 2710. In the example embodiment of FIG. 27, six transceivers 2710 have been positioned around the volleyball court. However, this is for example purposes only as the number and positioning of the transceivers can be modified based on the field of view of each transceiver and the coverage area for the field of play 2705. For example, the number and positioning of the transceivers 2710 may be designed so that the athletic performance measuring unit 1400 worn by an athlete 2715 can be sensed by at least one transceiver 2710 when the athlete is on the field of play 2705, within the "out of bounds" lines, or within the foul lines. In one example embodiment, the number and positioning of the transceivers can be such that every portion of the field of play 2705 is capable of being sensed by at least three transceivers 2710 so that the exact position of an athletic performance measuring unit 1400 on the field of play can be determined (and accordingly, the location of the athlete wearing that unit 1400 can be tracked). The transceivers 2710 can each be communicably coupled to a PPU (e.g., a smart device 2515A) or a non-personal computer (not shown), such as a server computer, to receive and process the data received by the transceivers 2710. The PPU and/or non-personal computer can either be provided software by the web server 2530 to process the data received by the transceivers 2710 or can transmit the transceiver data to the web server 2530 for processing at the web server 2530. In the system 2700 the field of play contains one or more athletes 2715. One or more of these athletes 2715 can be wearing or have attached to them or another device they are using in competition, an athletic performance measuring unit 1400. This will allow for the monitoring not only of the desired athletic performance parameters typically provided by the unit 1400 but also the amount of time that the athlete 2715 is taking part in the athletic event and the location of the athlete 2715 at all times when the athlete is on the field of play 2705 during the athletic event.

In one example embodiment, the coach or another member of an athlete's team can select athletes 2715 of the team to be monitored during an athletic event. This can be done via the web server 2530 using a PPU (e.g., the smart device 2515A or a laptop computer). While a coach may select all of his team's athletes 2715 for monitoring during an athletic competition, the coach may also select athletes 2715 from the opposing team, as monitoring their performance during an athletic event may provide strategic information. The coach or other person may also select the one or more athletic performance parameters they want to monitor for each athlete 2715. In certain example embodiments, the same or different parameters may be monitored for each of the selected athletes 2715.

At the start of the athletic event, a session may be started for all of the athletes 2715 selected or for all athletes wearing an athletic performance measuring unit 1400. In certain example embodiments, this session start can be done automatically, by each athlete 2715 through the use of the unit 1400, and/or by the coach selecting to start a coaching monitoring session. As an athlete 2715 enters the field of play 2705, the athlete can be sensed by one or more of the transceivers 2710 based on an athlete identifier, such as an IP address or an identifier code, received from the athletic performance measuring unit 1400. When the transceivers 2710 sense the athlete 2715 entering the field of play 2705 (either by sensing a signal or by sensing a signal having at least a predetermined strength), a signal can be sent to the PPU or non-personal computing device which can start a timer associated with the athlete 2715. The timer can represent the amount of time that the athlete is taking part in the athletic competition. In certain example embodiments, the timer can be linked to a game clock for the athletic event, such that the timer will only be incremented when the game clock is not stopped for a break in the action. Further, while the athlete, such as athlete 2715A or 2715C, is on the field of play 2705, the transceivers 2710 can also receive the athletic performance data sensed/calculated by the athletic performance measuring unit 1400 and can store and present that data for display at the athletic event, such as on the scoreboard 2505, to one or more PPUs 2515 at the athletic event, and/or to one or more PPUs 2515 at locations remote from the athletic event.

The transceivers 2710 can also monitor the exact position of the athlete 2715 on the field of play 2705 based on, for example, a triangulation of the signal received from the antenna 130 on the athletic performance measuring unit 1400 by multiple transceivers 2715. The position for the athlete, and in effect potentially all of the athletes 2715 on the field of play, can be communicated to the PPU and/or non-personal computing device. The PPU and/or non-personal computing device can either alone or via the web server 2530 generated a real-time or near real-time depiction of the field of play 2705 and the position of each athlete 2715 on the field of play for presentment on the PPU (e.g., smart device 2515A) and/or web server 2530 and/or for transmission to one or more PPUs, including those PPUs 2515 at the athletic event and those that are located remotely from the athletic event. In addition, the coach or another person on the team can input information related to plays being run by the team at the PPU. The PPU can retrieve information presenting the expected player positioning and movement for the input play and can overlay or underlay that or present a side-by-side comparison of the expected player positioning and movement and the actual payer positioning and movement on the display of the PPU in real-time or near real time. This comparison of expected to actual player positioning and movement can be stored on the web server 2530 or at the PPU (e.g., smart device 2515A) and can be used by the coach to show the players after the game or during a time when the players are on the side line the comparison and any errors the players may have made.

As athletes 2715 leave the field of play, such as athlete 2715B and 2715D, they leave the sensed area of the transceivers 2710. This can cause the transceivers 2710 to either no longer receive a signal from the unit 1400 worn by the athlete or to receive a sufficiently week signal such as would be representative of the player no longer being on the field of play. At that time, the transceivers 2710 can transmit a signal to the PPU and/or non-personal computing device, which can stop the timer associated with the athlete 2715 based on an athlete identifier, such as an IP address or an identifier code, received from the athletic performance measuring unit 1400. Accordingly, as different athletes 2715 enter and exit the field of play 2705, the exemplary system 2700 can track the location of each athlete 2715 based on that athlete's athletic performance measuring unit 1400 in real-time or near real-time, can retrieve and display locally, on the web server, or to PPUs not local to the athletic event, the desired sensed/calculated athletic performance data, and can measure and present the amount of time that the athlete 2715 has been on the field of play 2705 during the athletic event.

Figure 28A:
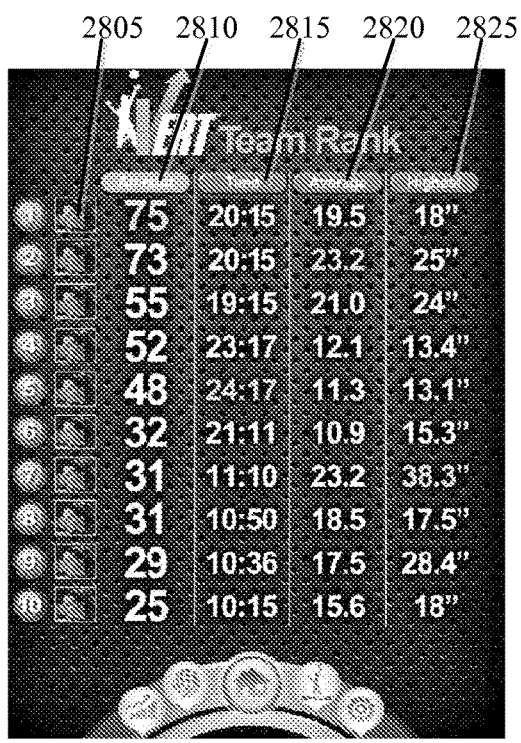
FIGS. 28A-B present example depictions of screenshots of a social mobile application communicably connected to a web server for the display of a team management and real-time athletic performance parameter evaluation portal provided via a social mobile application via the web server in accordance with one example embodiment of the disclosure.
Figure 28B:
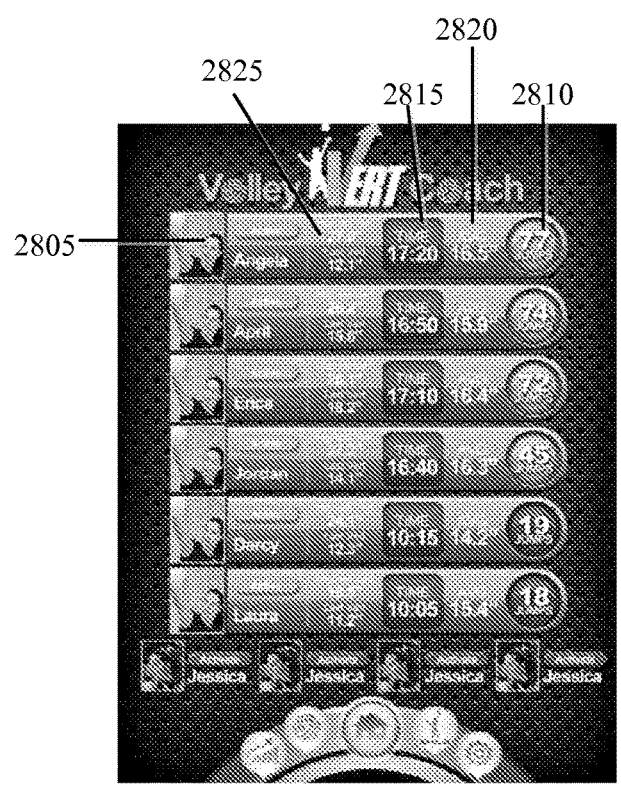

FIGS. 28A-B present example depictions of screenshots for a team management and real-time athletic performance parameter evaluation portal provided via a social media mobile application communicably coupled to the social media web server in accordance with one example embodiment of the disclosure. Referring to FIGS. 28A-B the evaluation portal can be a very useful tool for coaches and other evaluators. For example, as shown the mobile application may provide an identifier 2805 for each of the selected athletes on the team. The identifier can be the player's name, number, picture, or any other unique identifier. Further, the portal can provide a listing of certain athletic performance parameters such as the number of jumps 2810, the time 2815 that each player has been in the game, an average 2820 for the desired athletic performance parameter (e.g., average jump height, average swing speed, etc.) and the peak or highest value 2825 that each player has received for the desired athletic performance parameter (e.g., highest jump, fastest swing speed, etc.).

In addition, FIG. 28B presents screenshots of a social media mobile application communicably coupled to a web server and presenting an alternative method for tracking player participation during an athletic event. As shown in FIG. 28B, in situations where a system similar that that described in FIG. 27 is not provided for tracking the time players are in the game, the coach or assistant may manually select and deselect the players in the game and track the participation time in that manner.

As such, a coach or other team manager or member can review this data to know how long each of the athletes 2715 on his and/or the other team have been playing in the current athletic event, the current, historical and/or change in one or more athletic performance parameters, and the positioning of one or more athletes 2715 on the field of play 2705 during the athletic event in real-time or near real-time. This information can be used by the coach to evaluate fatigue of athletes 2715 and to determine when an athlete 2715 should be substituted for based on a deterioration in one or more athletic performance parameters over the time played.

In another example embodiment, the athletic performance measuring unit 1400 also has the capability to be configured in more complicated situations were multiple units 1400 work together in a meshed network configuration. A mesh capable computing unit 100A is optionally used in place of the basic computing unit 100 using the same athletic sensor sets 120. In such an example configuration, each unit 1400 can make peer wireless connections to nearby units 1400 in the mesh in such a way that only one data logging unit or PPU, (e.g., personal computer, laptop computer, tablet, or smart phone) would be necessary to pull data from any and all athletic performance measuring units 1400 in the mesh network. In this way, the athletic performance measuring unit 1400 can also be scaled to receive and provide team performance information in a coordinated way. The following are some basic examples of different contemplated configurations.

Figure 29:
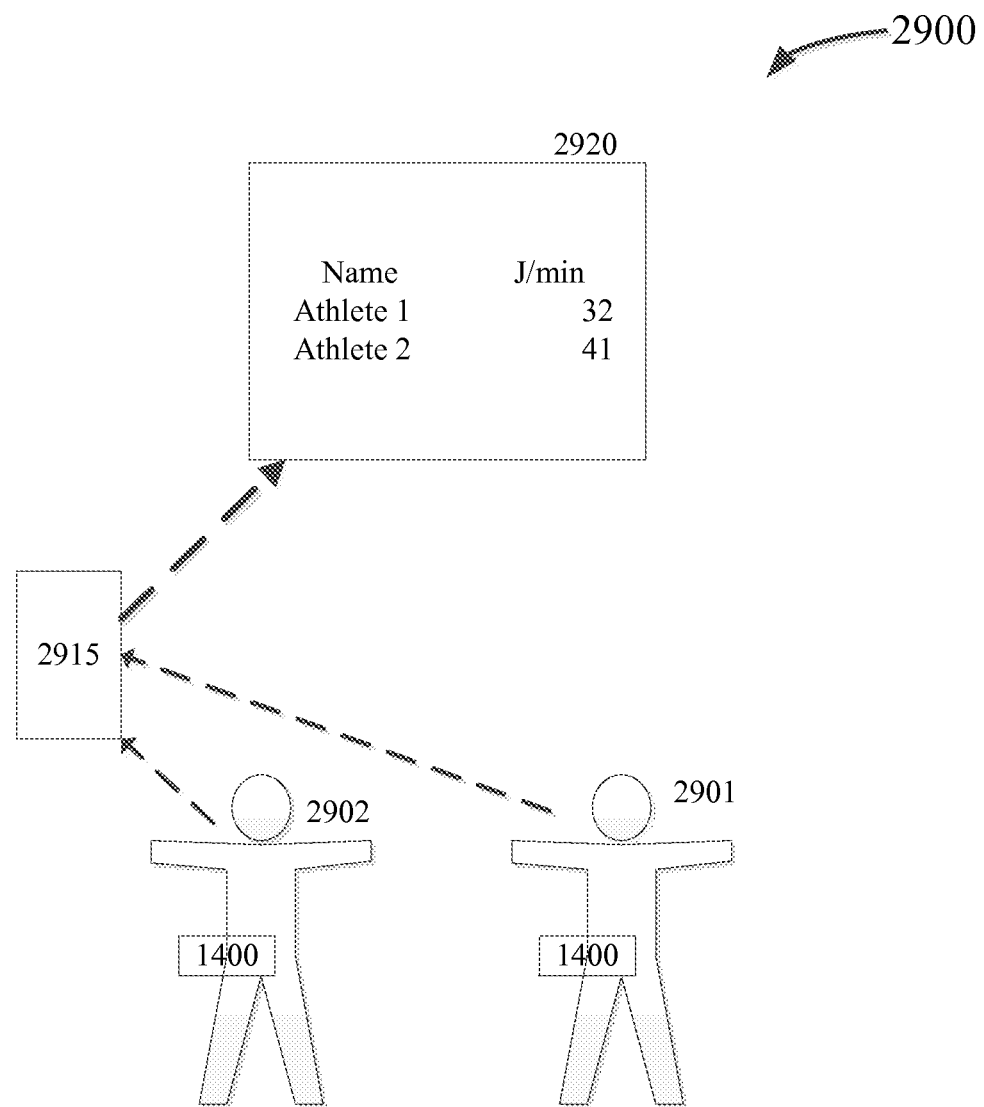
FIG. 29 is a graphical illustration of a method of using the athletic performance measuring unit in a gym environment in accordance with one exemplary embodiment of the disclosure.

FIG. 29 is a graphical illustration of a system 2900 of using the athletic performance measuring unit in a gym environment in accordance with one exemplary embodiment of the disclosure. Referring to FIGS. 14A-H and 29, the exemplary system 2900 can be located in a gym or other type of workout location or facility. In one example embodiment, each athlete 2901, 2902 can have an athletic performance measuring unit 1400 coupled to or otherwise associated with the athlete 2901, 2902. Each of the athletic performance measuring units 1400 can be communicably coupled to one or more PPUs 2915 and/or a non-personal computing device (not shown). While the example embodiment of FIG. 29 depicts a single PPU 2915, in alternative embodiments, more than one, include one PPU for each athletic performance measuring unit 1400 may be provided. The system further includes a video board or television 2920. In one example embodiment, the television 2920 is configured to receive athletic performance parameters from the one or more PPUs 2915 and/or the non-personal computing device and display the received athletic performance parameters on the television screen 2920.

For example, the athletic performance measuring unit 1400 for each athlete 2901, 2902 may include a unique identifier that is transmitted with the sensor data or the calculated athletic performance parameters to the PPU 2915 and/or the non-personal computing device. The PPU 2915 and/or the non-personal computing device can, based on the received sensor data from the units 1400, calculate athletic performance parameters for each of the athletes 2901, 2902. The PPU 2915 and/or the non-personal computing device can then transmit the name or other identifier associated with the athlete and the athlete's calculated or sensed athletic performance parameters to the television 2920 for display. In one example embodiment, multiple athletes and multiple athletic performance parameters can be displayed on the television 2920 at the same time or substantially the same time, thereby allowing each athlete to compare their results to those of other athletes during their workout. For example, multiple athletes, each wearing a athletic performance measuring unit 1400 can be jumping rope at the same time. The unit 1400 can provide sensor data to the PPU 2915, which can calculate the rate (in jumps per minute) that each athlete is jumping rope. The PPU 2915 can then transmit an identifier for each athlete and the calculated jump rate for each athlete for display on the television screen 2920. In addition, the prior workout data either stored in the unit 1400 or the PPU 2915 or non-personal computing device can be retrieved for each of the athletes. This prior workout data that includes the athletic performance parameter can also be transmitted to the television 2920 for display on the screen near or adjacent to the current athletic performance parameter. In this way, each athlete can compare the metrics of their current workout against prior workouts in real-time or near real-time and can determine any improvement over prior workouts. While jumps per minute have been shown as the athletic performance parameter, any other parameters may be measured by the unit 1400 and presented for display on the television screen 2920.

While the above has been described with reference to a coach or other member of the team making the selections and desiring to monitor the athletes, in another example embodiment, other people including, but not limited to, a fan or another person associated with the team may also desire to monitor the athletic performance parameters, as well as time of play and positioning of the athletes during the athletic event.

One benefit of the props feature provided on the example website is that it allows a fan to have the ability to give "props" to someone (similar to "like" on FACEBOOK®). Another benefit of the props feature is that the person receiving props feels the enjoyment of support by fans, friends, parents, etc. Yet another benefit of the props feature is that it provides a mechanism to let the receiving athlete know what if feels like to be endorsed or associated with an advertiser. For example the receiving athlete can be presented alongside or associated with advertising/advertisers of varied size and scope on the website based on the number of props the particular athlete receives.

Figure 30:
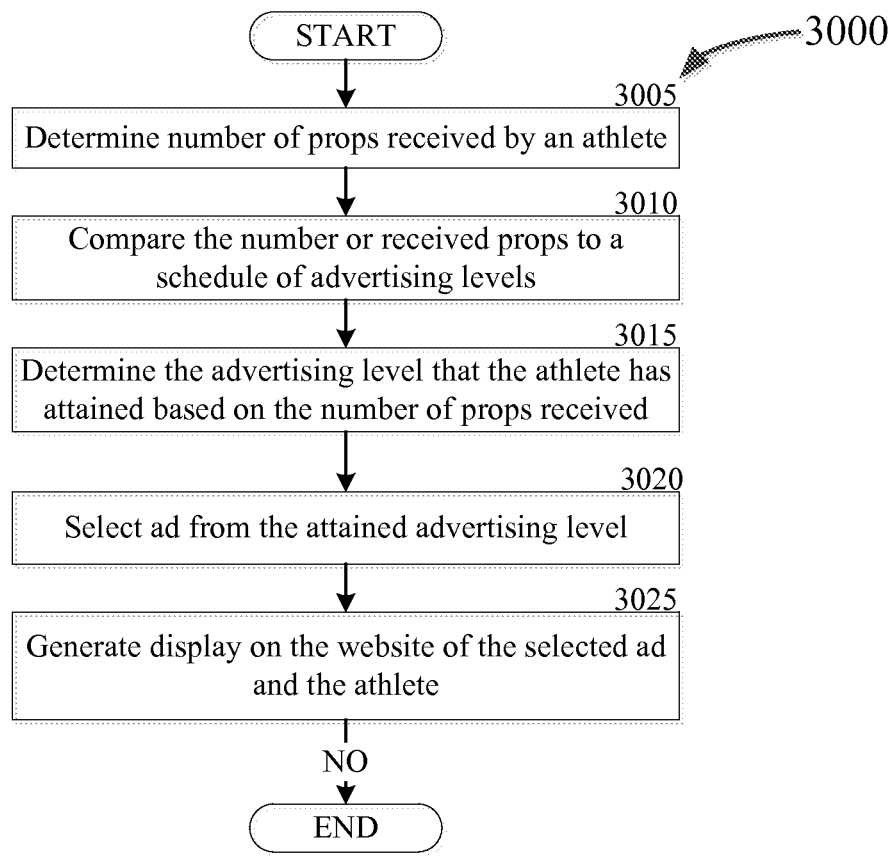
FIG. 30 is a flow chart of a method for associating advertising to athletes based on props rankings in accordance with one exemplary embodiment of the disclosure.

FIG. 30 is a flow chart of a method 3000 for associating advertising to athletes based on props rankings in accordance with one exemplary embodiment of the disclosure. Referring now to FIG. 30, the exemplary method 3000 begins at the start step and proceeds to step 3005 where a determination is made as to the number of props received by an athlete. In one example, the number of received props are associated with a single athletic performance parameter or video. In alternative embodiments, the number of received props are calculated over a predetermined period of time, such as one day, one week, one month, or any other amount between 1-1000 days. In one example embodiment, the determination is made by the web server.

In step 3010, the number of received props determined in step 3005 is compared to a schedule of advertising levels. In one exemplary embodiment, the comparison is made by the web server. For example, as the athlete receives a higher number of props, the scope of the advertising can be increased, such as 100 props gets the athlete an endorsement from an advertiser/advertisement limited to the athlete's local area, 500 props gets the athlete an endorsement from an advertiser/advertisement limited to the athlete's state, 1500 props gets the athlete an endorsement from an advertiser/advertisement limited to a region of the United States, and 2500 props gets the athlete an endorsement from an national advertiser/advertisement. For example, Bill Loni is a star basketball player in Plantation, Fla. Bill received 2,500 props from his performance on Friday night's game which elevated his props number from 100 and an endorsement from a Plantation-area bagel shop, BORGER'S BAGELS™, to a national endorsement from RED BULL®. The number of levels and the number of props needed to attain each level can be stored in memory of or communicably coupled to the web server along with advertisements for each of those levels. Further, the number of levels and the number of props needed to attain each level presented above is for example only as the number of levels and the number of props needed to attain each level is configurable based on the particular market.

In step 3015, the web server can determine the advertising level that the athlete has attained based on then number of props received. In the example above, Bill Loni has attached a national advertising level based on his receipt of 2500 props. The web server can select an ad from the attached advertising level in step 3020. In the example above, the web server selects from the national advertising level. In step 3025, the web server generates a display of the selected ad and the athlete. In one example embodiment, the name and a picture of the athlete can be presented in proximity the selected advertisement. Further, the athletic performance parameter that generated the props can also be displayed with the athlete's name. Additionally, location information and other information about the athlete can be displayed in proximity to the selected advertisement.

In addition, the web server can provide the generated advertisement and athlete information to other social networking websites. For example, Bill Loni's endorsement can be shared on all his current social networks such as TWITTER®, FACEBOOK®, and YOUTUBE® and all his fans that supported him to get to a national level of endorsement can view the generated display. Further, Bill knows what it feels like to be endorsed by a sponsor similar to a professional athlete with social currency as his high number of props is similar to a social currency system that recognizes a user based on social influence The process then continues to the END step.

Accordingly, example embodiments disclosed herein can provide the technical effects of creating an apparatus, system, and method for measuring athletic performance characteristics of an athlete. In this regard, athletes and those who like to follow them can be provided with real-time data related to a multitude of a potential athletic performance parameters associated with a particular sport. In addition, the athlete and post this athletic performance parameter data on a web server, such as a social website uniquely designed to present and compare those performance parameters to peers and to track the change of those parameters over time for an athlete, group of athletes, and even an entire team.

Although example embodiments of the disclosure have been described, one of ordinary skill in the art will recognize that numerous other modifications and alternative embodiments are within the scope of the disclosure. For example, any of the functionality and/or processing capabilities described with respect to a particular device or component may be performed by any other device or component. Furthermore, while various example implementations and architectures have been described in accordance with example embodiments of the disclosure, one of ordinary skill in the art will appreciate that numerous other modifications to the example implementations and architectures described herein are also within the scope of this disclosure.

Certain aspects of the disclosure are described above with reference to block and flow diagrams of systems, methods, apparatuses, and/or computer program products according to example embodiments. It will be understood that one or more blocks of the block diagrams and steps of the flow diagrams, and combinations of blocks in the block diagrams and steps of the flow diagrams, respectively, may be implemented by execution of computer-executable program instructions. Likewise, some blocks of the block diagrams and steps of the flow diagrams may not necessarily need to be performed in the order presented, or may not necessarily need to be performed at all, according to some embodiments. Further, additional components and/or operations beyond those depicted in blocks of the block and/or steps of the flow diagrams may be present in certain embodiments.

Accordingly, blocks of the block diagrams and steps of the flow diagrams support combinations of means for performing the specified functions, combinations of elements or steps for performing the specified functions and program instruction means for performing the specified functions. It will also be understood that each block of the block diagrams and step of the flow diagrams, and combinations of blocks in the block diagrams and steps of the flow diagrams, may be implemented by special-purpose, hardware-based computer systems that perform the specified functions, elements or steps, or combinations of special-purpose hardware and computer instructions.

Computer-executable program instructions may be loaded onto a special-purpose computer or other particular machine, a processor, or other programmable data processing apparatus to produce a particular machine, such that execution of the instructions on the computer, processor, or other programmable data processing apparatus causes one or more functions or steps specified in the flow diagrams to be performed. These computer program instructions may also be stored in a computer-readable storage medium (CRSM) that upon execution may direct a computer or other programmable data processing apparatus to function in a particular manner, such that the instructions stored in the computer-readable storage medium produce an article of manufacture including instruction means that implement one or more functions or steps specified in the flow diagrams. The computer program instructions may also be loaded onto a computer or other programmable data processing apparatus to cause a series of operational elements or steps to be performed on the computer or other programmable apparatus to produce a computer-implemented process.

Additional types of CRSM that may be present in any of the devices described herein may include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile disc (DVD) or other optical storage, magnetic cassettes, magnetic tape, magnetic disk storage or other magnetic storage devices, or any other medium which can be used to store the information and which can be accessed. Combinations of any of the above are also included within the scope of CRSM. Alternatively, computer-readable communication media (CRCM) may include computer-readable instructions, program modules, or other data transmitted within a data signal, such as a carrier wave, or other transmission. However, as used herein, CRSM does not include CRCM.

Although example embodiments have been described in language specific to structural features and/or methodological acts, it is to be understood that the disclosure is not necessarily limited to the specific features or acts described. Rather, the specific features and acts are disclosed as illustrative forms of implementing the example embodiments. Conditional language, such as, among others, "can," "could," "might," or "may," unless specifically stated otherwise, or otherwise understood within the context as used, is generally intended to convey that certain example embodiments could include, while other example embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

What is claimed is:

1. A system for monitoring activities of one or more athletes during an athletic event on a field of play, the system comprising:
   one or more athletic performance measuring units that are each associated with one of the one or more athletes, wherein, during the athletic event, each of the one or more athletic performance measuring units is configured to:
      collect sensor data in real-time corresponding to an athletic performance characteristic;
      calculate an athletic performance parameter substantially in real-time based on the collected sensor data; and
      transmit the athletic performance parameter to at least one other electronic device;
   a plurality of transceivers placed within or around the field of play and configured to receive signals from the one or more athletic performance measuring units during the athletic event; and
   a computing device communicably coupled with the plurality of transceivers and configured to:
      receive, from the plurality of transceivers, data representing the signals received by the plurality of transceivers from the one or more athletic performance measuring units; and
      monitor, during the athletic event, a respective position of each athletic performance measuring unit within the one or more athletic performance measuring units based on the data representing the signals from the one or more athletic performance measuring units.

2. The system of claim 1, wherein each of the one or more athletic performance measuring units are associated with an identifier corresponding to one of the one or more athletes.

3. The system of claim 1, wherein the computing device is further configured to:
   determine, based on the received data representing the signals received by the plurality of transceivers from the one or more athletic performance measuring units, that a particular athletic performance measuring unit from among the one or more athletic performance measuring units has entered the field of play; and
   record a time of entrance to the field of play for a particular athlete associated with the particular athletic performance measuring unit based on determining that the particular athletic performance measuring unit has entered the field of play.

4. The system of claim 3, wherein the computing device is further configured to:
   determine, based on the received data representing the signals received by the plurality of transceivers from the one or more athletic performance measuring units, that the particular athletic performance measuring unit has exited the field of play;
   record a time of exit from the field of play for the particular athlete associated with the particular athletic performance measuring unit based on determining that the particular athletic performance measuring unit has exited the field of play; and
   compute, based on times of entrance to the field of play and exit from the field of play for the particular athlete, an amount of time that the particular athlete has spent on the field of play during the athletic event.

5. The system of claim 4, wherein:
   recording the time of entrance to the field of play for the particular athlete associated with the particular athletic performance measuring unit comprises initiating a timer for the particular athlete; and
   recording the time of exit from the field of play for the particular athlete associated with the particular athletic performance measuring unit comprises terminating the timer for the particular athlete.

6. The system of claim 5, wherein the data indicating the athletic performance parameter for the particular athlete is provided for output in response to determining, based on received data representing the signals received by the plurality of transceivers from the one or more athletic performance measuring units, that the particular athletic performance measuring unit has exited the field of play.

7. The system of claim 4, wherein the computing device is further configured to provide times of entrance to the field of play and exit from the field of play for the particular athlete to a web server.

8. The system of claim 1, wherein the computing device is further configured to:
   provide, for output to a display associated with the field of play, data indicating an athletic performance parameter for a particular athlete computed by a particular athletic performance measuring unit from among the one or more athletic performance measuring units.

9. The system of claim 1, wherein:
   the computing device is further configured to receive, from a computing device of an individual associated with the one or more athletes, data indicating respective pre-planned positions on the field of play for the one or more athletic performance measuring units on the field of play during the athletic event; and
   monitoring the respective position of each athletic performance measuring unit within the one or more athletic performance measuring units comprises:
      determining a respective detected location for each athletic performance measuring unit within the one or more athletic performance measuring units, and
      comparing the detected and pre-planned locations of each particular athletic performance measuring unit.

10. The system of claim 9, wherein the pre-planned positions on the field of play for the one or more athletic performance measuring units is specified by a strategic play associated with the athletic event.

11. A method performed by one or more computers, the method comprising:
   determining that an athletic event on a field of play has started; and
   during the athletic event:
      obtaining, from a plurality of transceivers placed within or around the field of play, data representing signals received from one or more athletic performance measuring units during an athletic event on the field of play, wherein each of the one or more athletic performance measuring units is associated with one of one or more athletes and configured to:
  collect sensor data in real-time corresponding to an athletic performance characteristic,
  calculate an athletic performance parameter substantially in real-time based on the collected sensor data, and
  transmit the athletic performance parameter to at least one other electronic device;
monitoring a respective position of each of the one or more athletic performance measuring units based on obtained data representing the signals received from the plurality of transceivers;
determining that the athletic event on the field of play has ended; and
providing, for output, data representing the monitored positions for the one or more athletic performance measuring units during the athletic event.

12. The method of claim 11, wherein each of the one or more athletic performance measuring units is associated with an identifier corresponding to one of the one or more athletes.

13. The method of claim 11, wherein during the athletic event, the method further comprises:
determining, based on the received data representing the signals received by the plurality of transceivers from the one or more athletic performance measuring units, that a particular athletic performance measuring unit from among the one or more athletic performance measuring units has entered the field of play; and
recording a time of entrance to the field of play for a particular athlete associated with the particular athletic performance measuring unit based on determining that the particular athletic performance measuring unit has entered the field of play.

14. The method of claim 13, wherein during the athletic event, the method further comprises:
determining, based on the received data representing the signals received by the plurality of transceivers from the one or more athletic performance measuring units, that the particular athletic performance measuring unit has exited the field of play;
recording a time of exit from the field of play for the particular athlete associated with the particular athletic performance measuring unit based on determining that the particular athletic performance measuring unit has exited the field of play; and
computing, based on times of entrance to the field of play and exit from the field of play for the particular athlete, an amount of time that the particular athlete has spent on the field of play during the athletic event.

15. The method of claim 11, wherein during the athletic event, the method further comprises:
providing, for output to a display associated with the field of play, data indicating an athletic performance parameter for a particular athlete computed by a particular athletic performance measuring unit from among the one or more athletic performance measuring units.

16. The device of claim 15, wherein during the athletic event, wherein the operations further comprise:
determining, based on the obtained data representing the signals received by the plurality of transceivers from the one or more athletic performance measuring units, that a particular athletic performance measuring unit from among the one or more athletic performance measuring units has entered the field of play; and
recording a time of entrance to the field of play for a particular athlete associated with the particular athletic performance measuring unit based on determining that the particular athletic performance measuring unit has entered the field of play.

17. The method of claim 11, wherein:
during the athletic event, the method further comprises receiving, from a computing device of an individual associated with the one or more athletes, data indicating respective pre-planned positions on the field of play for the one or more athletic performance measuring units on the field of play during the athletic event; and
monitoring a respective position of each athletic performance measuring unit within the one or more athletic performance measuring units comprises:
  determining a respective detected location for each athletic performance measuring unit within the one or more athletic performance measuring units, and
  comparing the detected and pre-planned locations of each particular athletic performance measuring unit.

18. The device of claim 16, wherein, during the athletic event, wherein the operations further comprise:
determining, based on the obtained data representing the signals received by the plurality of transceivers from the one or more athletic performance measuring units, that the particular athletic performance measuring unit has exited the field of play;
recording a time of exit from the field of play for the particular athlete associated with the particular athletic performance measuring unit based on determining that the particular athletic performance measuring unit has exited the field of play; and
computing, based on times of entrance to the field of play and exit from the field of play for the particular athlete, an amount of time that the particular athlete has spent on the field of play during the athletic event.

19. The method of claim 11, wherein:
the data representing signals received from the one or more athletic performance measuring units during an athletic event on the field of play comprises:
  data representing a first signal collected by a first transceiver from among the plurality of transceivers, the first signal having a signal strength representing a proximity of a particular athletic performance measuring unit from among the one or more athletic performance measuring units and the first transceiver, and
  data representing a second signal collected by a second transceiver from among the plurality of transceivers, the second signal having a signal strength representing a proximity of the particular athletic performance measuring unit and the second transceiver; and
monitoring the respective position of each of the one or more athletic performance measuring units comprises:
  obtaining data indicating a relative arrangement of the first and second transceivers on the field of play, and
  determining a position of the particular athletic performance measuring unit on the field of play based on (i) the signal strength of the first signal, (ii) the signal strength of the second signal, and (iii) the data indicating the relative arrangement of the first and second transceivers on the field of play.

20. A non-transitory computer-readable storage device encoded with computer program instructions that, when executed by one or more computers, cause the one or more computers to perform operations comprising:

determining that an athletic event on a field of play has started;

during the athletic event:

obtaining, from a plurality of transceivers placed within or around the field of play, data representing signals received from one or more athletic performance measuring units during an athletic event on the field of play, wherein each of the one or more athletic performance measuring units is associated with one of one or more athletes and configured to:

collect sensor data in real-time corresponding to an athletic performance characteristic, calculate an athletic performance parameter substantially in real-time based on the collected sensor data, and transmit the athletic performance parameter to at least one other electronic device;

monitoring a respective position of each of the one or more athletic performance measuring units based on the obtained data representing the signals received from the one or more athletic performance measuring units;

determining that the athletic event on the field of play has ended; and providing, for output, data representing the monitored positions for the one or more athletic performance measuring units during the athletic event.

* * * * *